(12) United States Patent
Player et al.

(10) Patent No.: US 7,728,003 B2
(45) Date of Patent: Jun. 1, 2010

(54) 5-OXO-5,8-DIHYDRO-PYRIDO-PYRIMIDINES AS INHIBITORS OF C-FMS KINASE

(75) Inventors: Mark R. Player, Phoenixville, PA (US); Hui Huang, Monroe Township, NJ (US); Hu Huaping, Pennington, NJ (US); Renee L. DesJarlais, Saint Davids, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 568 days.

(21) Appl. No.: 11/519,662

(22) Filed: Sep. 12, 2006

(65) Prior Publication Data

US 2007/0060578 A1 Mar. 15, 2007

Related U.S. Application Data

(60) Provisional application No. 60/799,605, filed on May 10, 2006, provisional application No. 60/714,526, filed on Sep. 14, 2005.

(51) Int. Cl.
*A61K 31/44* (2006.01)
*C07D 471/04* (2006.01)

(52) U.S. Cl. .................. 514/303; 544/279
(58) Field of Classification Search ............... 544/279; 514/303

See application file for complete search history.

(56) References Cited

U.S. PATENT DOCUMENTS 4,556,709 A * 12/1985 Grohe et al. ............... 544/117
2005/0049274 A1    3/2005  Wall et al.

FOREIGN PATENT DOCUMENTS

| EP | 0014390 | 8/1980 |
|---|---|---|
| EP | 0787726 | 8/1997 |
| JP | 09221424 | 8/1997 |
| WO | WO 96/34867 | 11/1996 |
| WO | WO 99/09030 | 2/1999 |
| WO | WO 01/70741 | 9/2001 |
| WO | WO 2005/009967 | 2/2005 |
| WO | WO 2007/033232 | 3/2007 |

OTHER PUBLICATIONS

Huff, Joel R., "HIV Protease: A Novel Chemotherapeutic Target for AIDS," Journal of Medicinal Chemistry, vol. 34, No. 8, Aug. 1991, pp. 2305-2314.*
Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th Edition (1996), vol. 2, pp. 1992-1996.*
FDA mulls drug to slow late-stage Alzheimer's [online], [retrieved on Sep. 23, 2003]. Retrived from the internet, URL<http://www.cnn.com/2003/HEALTH/conditions/09/24/alzheimers.drug.ap/index.html>.*
Byrn et al., Solid-State Chemistry of Drugs, Second Edition, 1999, pp. 233-247.*
PCT International Search Report, dated Feb. 2, 2007, for PCT Int'l. Appln. No. PCT/US2006/035421.
Abstract, "Anti-neoplastic agent effective against solid tumours and leukaemia—comprising 7-substituted 1-thiazolyl-1,8-naphthyridine derivative, showing high safety", Database WPI Week 199747, Derwent Publications Ltd., London, GB, AN 1997-506304, Appln. No. JP19960351948, filed Dec. 10, 1996.

* cited by examiner

*Primary Examiner*—Rebecca L Anderson

(57) ABSTRACT

The invention addresses the current need for selective and potent protein tyrosine kinase inhibitors by providing potent inhibitors of c-fms kinase. The invention is directed to the novel compounds of Formula I:

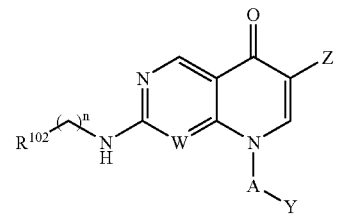

or a solvate, hydrate, tautomer or pharmaceutically acceptable salt thereof, wherein: W, A, Y, n, Z, and $R^{102}$ are described in the specification.

8 Claims, No Drawings

5-OXO-5,8-DIHYDRO-PYRIDO-PYRIMIDINES AS INHIBITORS OF C-FMS KINASE

CROSS REFERENCE TO RELATED APPLICATIONS

This present application claims benefit of U.S. Provisional Patent Application Ser. No. 60/714,526, filed Sep. 14, 2005 and U.S. Provisional Patent Application Ser. No. 60/799,605, filed May 10, 2006, which are incorporated herein by reference in their entirety and for all purposes.

BACKGROUND OF THE INVENTION

The invention relates to novel compounds that function as protein tyrosine kinase inhibitors. The family of 5-oxo-5,8-dihydro-pyrido-pyrimidines has exhibited promising pharmaceutical properties in the past; U.S. Pat. No. 4,556,709, JP 09221424 and DE 19532235 are indicative of recent investigations. More particularly, the invention relates to novel compounds that function as inhibitors of c-fms kinase.

c-Fms is a type III receptor tyrosine kinase selectively expressed on macrophages and their progenitors. The extracellular Ig domain of c-fms binds macrophage colony stimulating factor (M-CSF), also known as colony stimulating factor-1 (CSF-1). Binding of CSF-1 induces receptor dimerization and trans-phosphorylation of the intracellular c-fms kinase domain on Y723 and other tyrosine residues. Once phosphorylated, c-fms efficiently phosphorylates several cytoplasmic signaling molecules that lead to de novo gene expression and proliferation. Small molecule inhibitors of the kinase catalytic site of c-fms are expected to prevent CSF-1 induced cellular responses.

Macrophages are a predominant source of tumor necrosis factor (TNF) and interleukin-1 (IL-1) in the destructive pannus of rheumatoid arthritis. TNF and IL-1 activate stromal expression of hematopoietic factors including CSF-1. In turn, CSF-1 recruits monocytes and promotes macrophage survival, functional activation, and in some settings, proliferation. Thus, TNF and CSF-1 interact in a perpetuating cycle that leads to inflammation and joint destruction. The exclusive receptor for CSF-1 is c-fms, and the disclosed invention is a c-fms inhibitor designed to interrupt this cycle.

Macrophages are abundant at sites of chronic inflammation where they are are often the most important source of TNF, IL-1, and other cytokines. Moreover, macrophages can be an important source of factors that function in tissue remodeling such as plasminogen activators, matrix metalloproteases, vascular endothelial growth factor, and transforming growth factor-β. The numbers of macrophages present within target tissues have strongly correlated with disease severity in rheumatoid arthritis (Ann Rheum Dis 53 (1994) pp 39-44), immune nephritis (Kidney Int 54 (1998) pp 143-151), and graft rejection (Transpl Int 7 Suppl 1 (1994) pp 577-579). Macrophage numbers are also elevated in atherosclerotic plaque (Arch Pathol Lab Med 109 (1985) pp 445-449), adipose tissue in obesity (J Clin Invest 112 (2003) pp 1796-1898), diabetic nephropathy (Kidney Int 65 (2004) pp 116-128), cardiac hypertrophy (Hypertension 25 (1999) pp 132-138), and in many solid tumors (Trends in Immunology 23 (2002) pp 549-555), particularly breast cancer (J. Experimental Medicine 193 (2001) pp 727-739), where they are thought to contribute to disease progression. Modulation of macrophage function through inhibition of c-fms thus is expected to be useful in treating inflammatory mediated diseases and conditions.

Another example of the invention is the use of any of the compounds described herein in the preparation of a medicament for treating: rheumatoid arthritis, graft rejection, atherosclerosis, obesity, diabetic nephropathy, cardiac hypertrophy and solid tumor diseases, especially breast cancer, in a subject in need of such treatment.

Preclinical data suggest CSF-1/FMS is a particularly viable therapeutic target for rheumatoid arthritis. Recent work has shown that neutralizing antibodies to CSF-1 reduce substantially the severity of collagen-induced arthritis in mice (J Leukoc Biol 68 (2000) pp 144-150). The authors additionally demonstrated that recombinant CSF-1 exacerbated the disease progress in this model. Therefore, a preferred use for the invention is the treatment of rheumatoid arthritis.

SUMMARY OF THE INVENTION

The invention addresses the current need for selective and potent protein tyrosine kinase inhibitors by providing potent inhibitors of c-fms kinase.

The invention is directed to the novel compounds of Formula I:

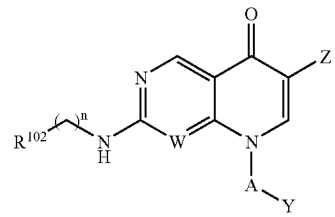

or a solvate, hydrate, tautomer or pharmaceutically acceptable salt thereof, wherein W, A, Y, n, Z and $R^{102}$ are as defined herein.

The invention is also directed to a method of using a compound of Formula I for inhibiting protein tyrosine kinase activity comprising administering an effective amount of at least one compound of Formula I.

The invention is directed to a method of inhibiting c-fms kinase activity in a subject in need thereof comprising administering to the subject an effective amount of at least one compound of Formula I.

The invention is also directed to a method of treating or ameliorating a c-fms kinase mediated disorder in a subject in need thereof comprising administering to the subject an effective amount of at least one compound of Formula I.

DETAILED DESCRIPTION OF THE INVENTION

This invention is directed to a compound of Formula I:

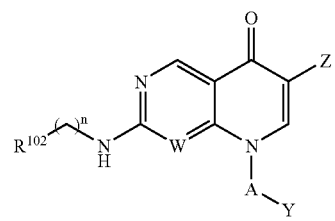

or a form thereof, wherein:
W is N or CH;
A is absent or alkyl;
Y is a ring selected from cycloalkyl, bicycloalkyl, aryl, alkylaryl, cycloalkylaryl, arylcycloalkyl, or heteroaryl provided that Y is not thiazole;

n is selected from 1, 2, 3 or 4;

$R^{102}$ is $NR^{103}R^{104}$, heteroaryl, alkoxy or phenyl optionally substituted with $R^{101}$;

$R^{101}$ is one, two or three substituents selected from hydroxyl, methyl, halogen, —$CF_3$, or methoxy;

$R^{103}$ and $R^{104}$ are independently hydrogen, alkyl, or $R^{103}$ and $R^{104}$ may be taken together to form a ring selected from the following:

[structures]

wherein $R^a$ is hydrogen or alkyl, $R^c$ is hydrogen, alkyl, alkoxyalkyl, —C(O)alkyl, or —$CH_2$C(O)alkyl and $R^d$ is hydrogen, alkyl, or Cl; and Z is $CO_2R^1$, or $CONR^1R^2$; wherein $R^1$ is hydrogen or alkyl; and $R^2$ is hydrogen, alkyl, cycloalkyl, or alkoxy; alternatively, $R^1$ and $R^2$ may be taken together to form a pyrrolidine or piperidine ring.

An example of the present invention is a compound of Formula I or a form thereof, wherein:

W is N or CH;

A is absent or alkyl;

Y is a ring selected from cycloalkyl, bicycloalkyl, aryl, alkylaryl, cycloalkylaryl, arylcycloalkyl, or heteroaryl provided that Y is not thiazole;

n is selected from 1, 2, 3 or 4;

$R^{102}$ is $NR^{103}R^{104}$, heteroaryl, alkoxy or phenyl optionally substituted with $R^{101}$;

$R^{101}$ is one, two or three substituents selected from hydroxyl, methyl, halogen, —$CF_3$, or methoxy;

$R^{103}$ and $R^{104}$ are independently hydrogen, alkyl, or $R^{103}$ and $R^{104}$ may be taken together to form a ring selected from the following:

[structures]

wherein $R^a$ is hydrogen or alkyl, $R^c$ is hydrogen, alkyl, alkoxyalkyl, —C(O)alkyl, or —$CH_2$C(O)alkyl and $R^d$ is hydrogen, alkyl, or Cl; and Z is $CO_2R^1$, or $CONR^1R^2$; wherein $R^1$ is hydrogen or alkyl; and $R^2$ is hydrogen, alkyl, cycloalkyl, or alkoxy; alternatively, $R^1$ and $R^2$ may be taken together to form a pyrrolidine or piperidine ring.

An example of the present invention is a compound of Formula I or a form thereof, wherein:

W is N or CH;

A is absent;

Y is a ring selected from cycloalkyl, bicycloalkyl, phenyl, alkylaryl, cycloalkylaryl, arylcycloalkyl, or heteroaryl provided that Y is not thiazole;

n is selected from 1, 2, 3 or 4;

$R^{102}$ is $NR^{103}R^{104}$, heteroaryl, alkoxy or phenyl optionally substituted with $R^{101}$;

$R^{101}$ is one, two or three substituents selected from hydroxyl, methyl, halogen, —$CF_3$, or methoxy;

$R^{103}$ and $R^{104}$ are independently hydrogen, $C_{(1-4)}$alkyl, or $R^{103}$ and $R^{104}$ may be taken together to form a ring selected from the following:

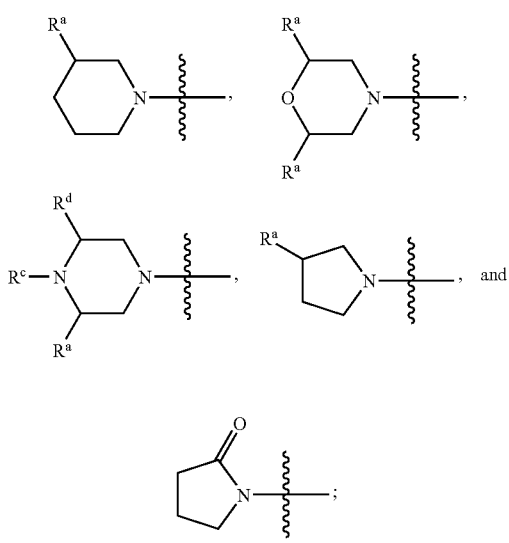

wherein
R$^a$ is hydrogen or C$_{(1-4)}$alkyl, R$^c$ is hydrogen, C$_{(1-4)}$alkyl, —C(O)—C$_{(1-4)}$alkyl, or —CH$_2$C(O)—C$_{(1-4)}$alkyl and R$^d$ is hydrogen, C$_{(1-4)}$alkyl, or Cl; and Z is CO$_2$R$^1$, or CONR$^1$R$^2$; wherein R$^1$ is hydrogen or C$_{(1-4)}$ alkyl; and R$^2$ is hydrogen, C$_{(1-4)}$alkyl, cycloalkyl, or C$_{(1-4)}$ alkoxy; alternatively, R$^1$ and R$^2$ may be taken together to form a pyrrolidine or piperidine ring.

An example of the present invention is a compound of Formula I or a form thereof, wherein: W is N;

A is absent;

Y is a ring selected from cyclohexyl, cyclopentyl, bicyclo[2.2.1]heptyl, phenyl, adamantanyl, indanyl, or 1,2,3,4-tetrahydro-naphthalenyl;

n is selected from 1, 2 or 3;

R$^{102}$ is NR$^{103}$R$^{104}$, heteroaryl, alkoxy or phenyl optionally substituted with R$^{101}$;

R$^{101}$ is one, two or three substituents selected from hydroxyl, methyl, halogen, —CF$_3$, or methoxy;

R$^{103}$ and R$^{104}$ are taken together to form a ring selected from the following:

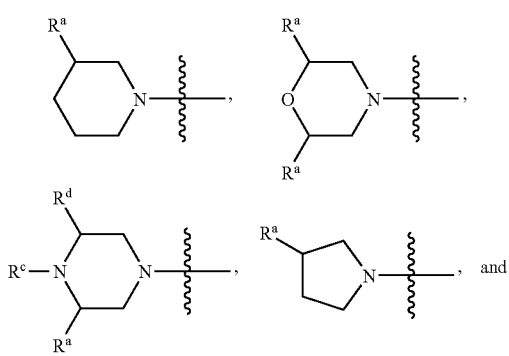

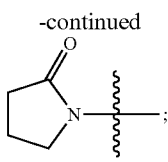

wherein

R$^a$ is hydrogen or C$_{(1-4)}$alkyl, R$^c$ is hydrogen, C$_{(1-4)}$alkyl, —C(O)—C$_{(1-4)}$alkyl, or —CH$_2$C(O)—C$_{(1-4)}$alkyl and R$^d$ is hydrogen, C$_{(1-4)}$alkyl, or Cl; and Z is CO$_2$R$^1$, or CONR$^1$R$^2$; wherein R$^1$ is hydrogen or C$_{(1-4)}$ alkyl; and R$^2$ is hydrogen, C$_{(1-4)}$alkyl, cycloalkyl, or C$_{(1-4)}$ alkoxy.

An example of the present invention is a compound of Formula I or a form thereof, wherein: W is N or CH;

A is absent or alkyl;

Y is a ring selected from indan-5-yl, phenyl, cyclohexyl, cyclopentyl, or adamantan-2-yl;

n is selected from 1, 2 or 3;

R$^{102}$ is 4-methyl-piperazin-1-yl, morpholinyl, piperidinyl, 2-oxo-pyrrolidin-1-yl, pyrrolidinyl, dimethylamino, alkoxy, imidazolyl, or phenyl optionally substituted with one or two methoxy substituents; and Z is CONR$^1$R$^2$; wherein R$^1$ is hydrogen or alkyl; and R$^2$ is hydrogen, alkyl, cycloalkyl, or alkoxy.

An example of the present invention is a compound of Formula I or a form thereof, selected from the group consisting of:

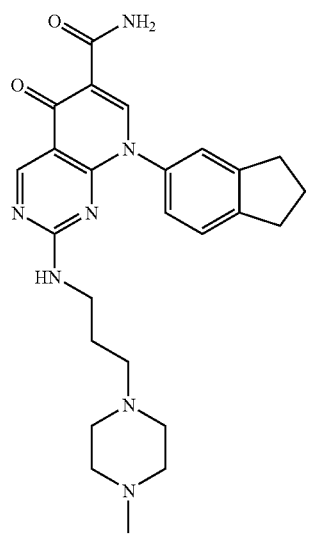

Cpd 1

-continued
Cpd 2
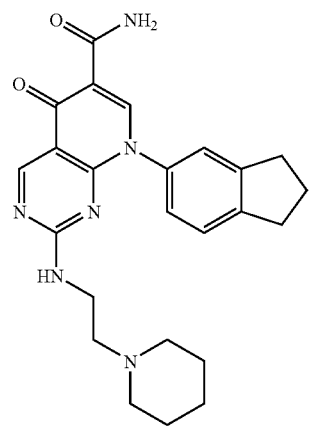
Cpd 3
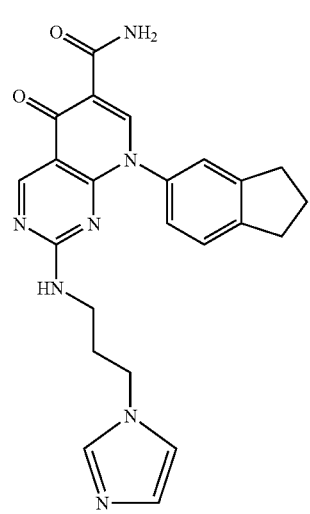
Cpd 4
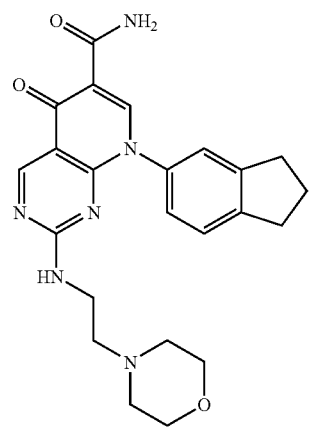
-continued
Cpd 5
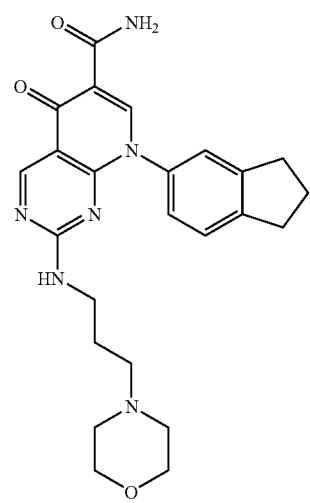
Cpd 6
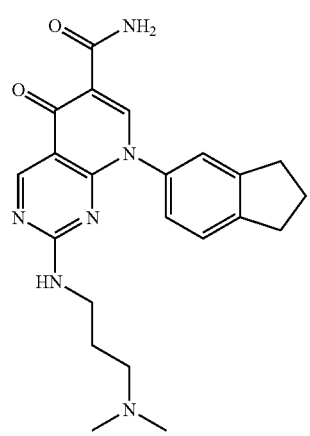
Cpd 7
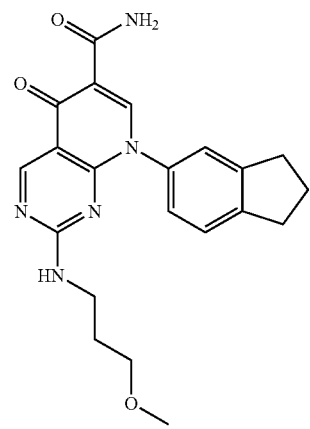

-continued
Cpd 8
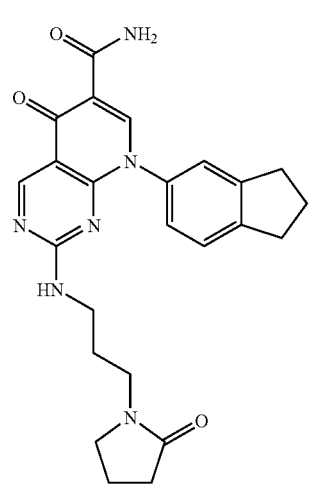
Cpd 9
Cpd 10
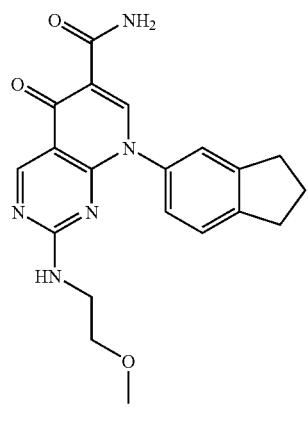
-continued
Cpd 11
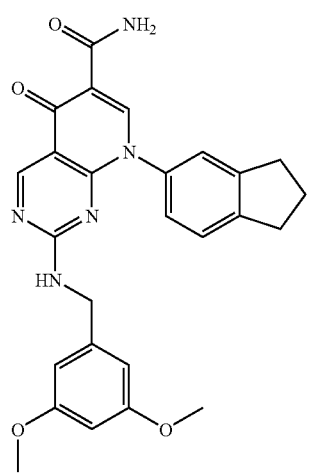
Cpd 12
Cpd 13

-continued
Cpd 14
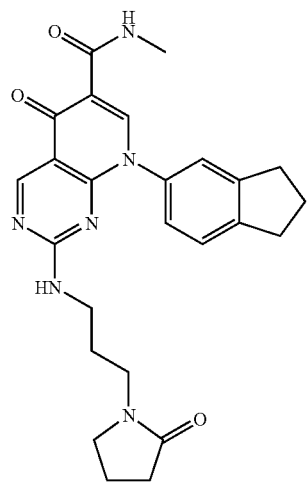
Cpd 15
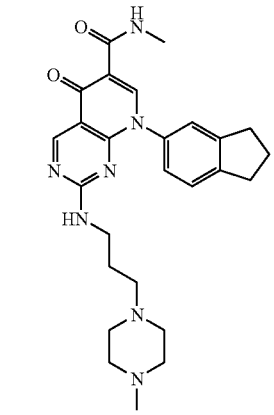
Cpd 16
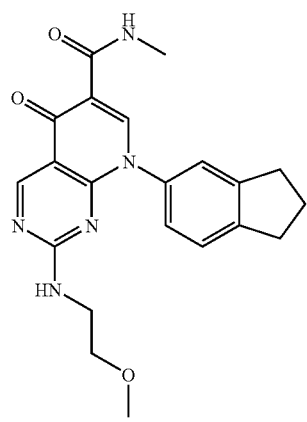
-continued
Cpd 17
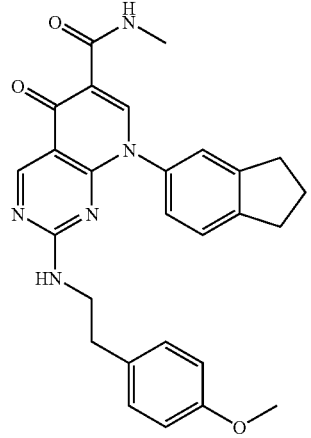
Cpd 18
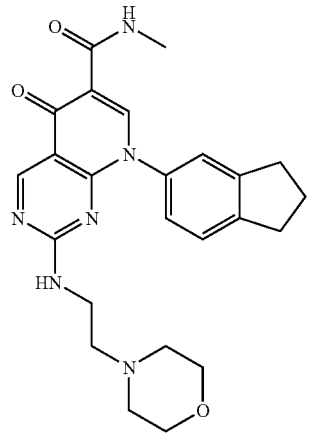
Cpd 19
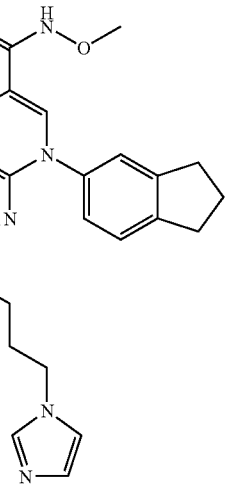

-continued
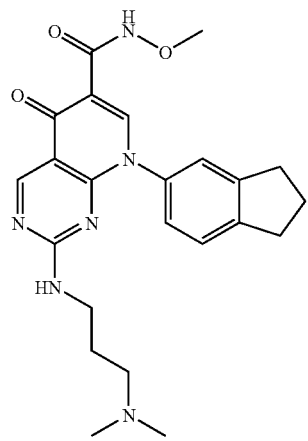
Cpd 20
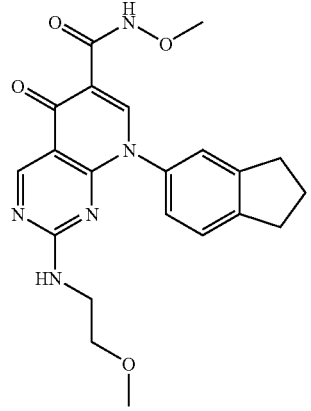
Cpd 23
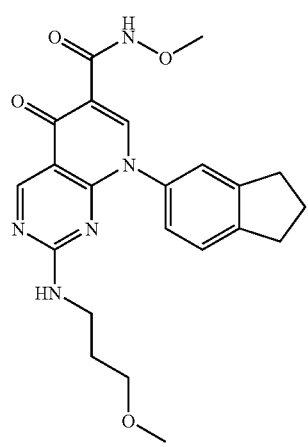
Cpd 21
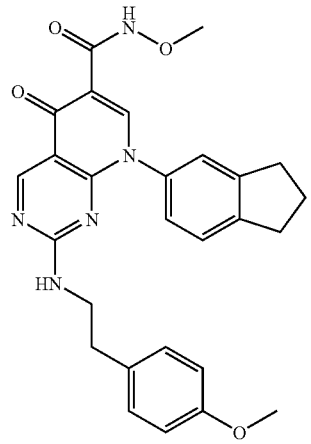
Cpd 24
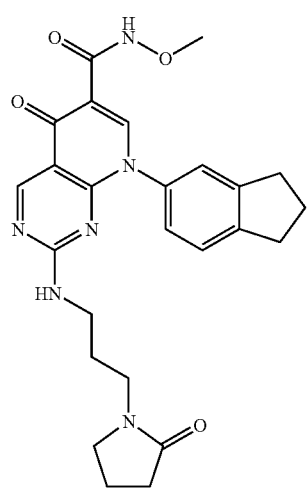
Cpd 22
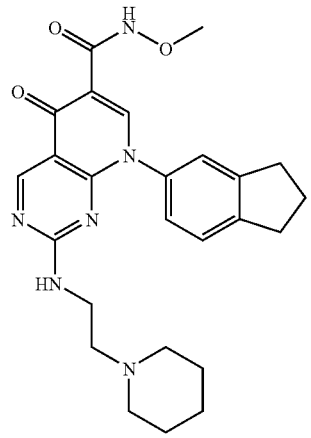
Cpd 25

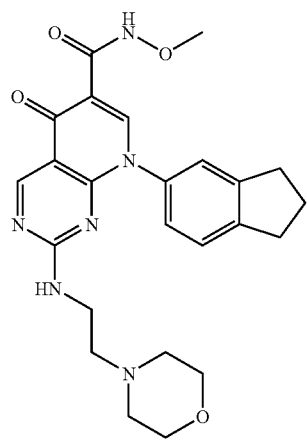
Cpd 26
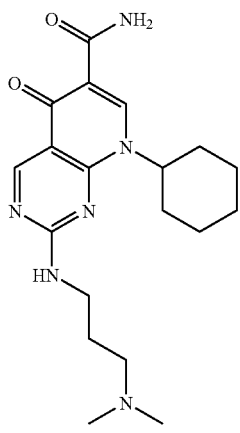
Cpd 29
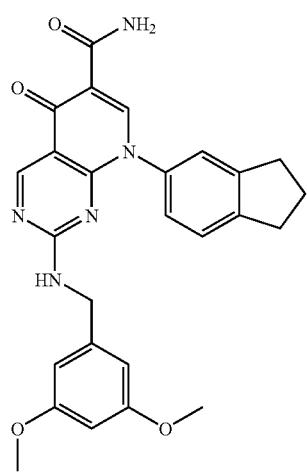
Cpd 27
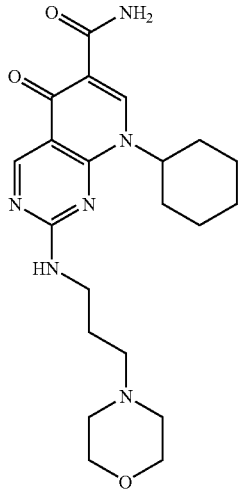
Cpd 30
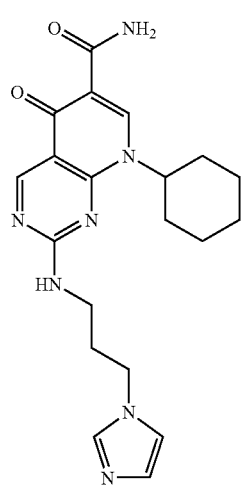
Cpd 28
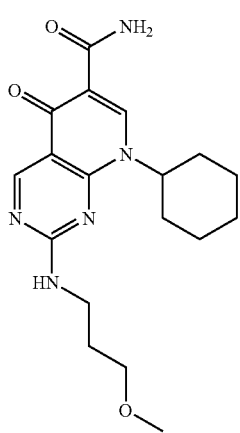
Cpd 31

Cpd 32
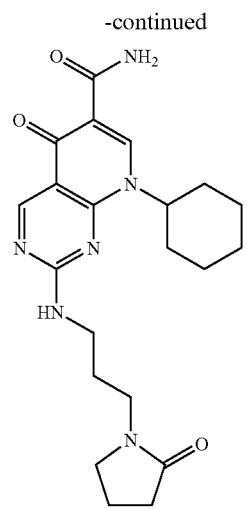
Cpd 33
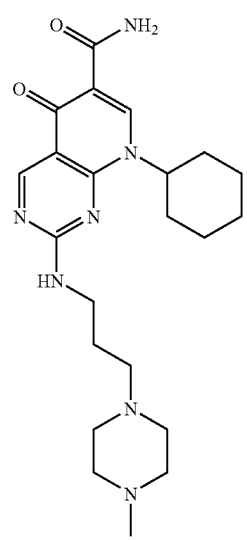
Cpd 34
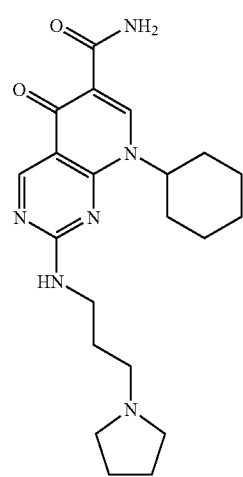
Cpd 35
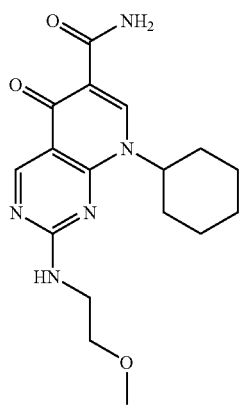
Cpd 36
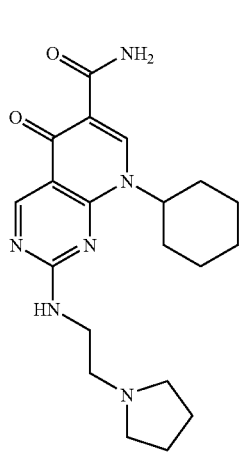
Cpd 37
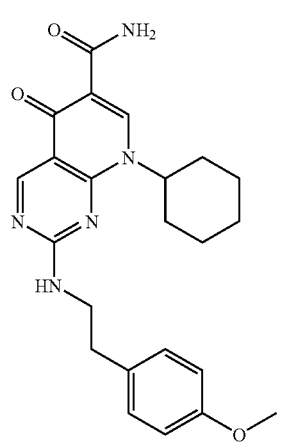

-continued
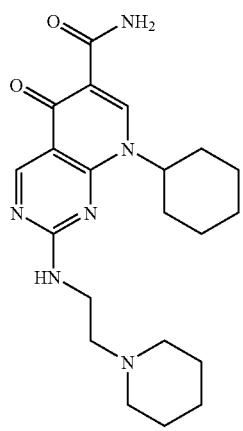
Cpd 38
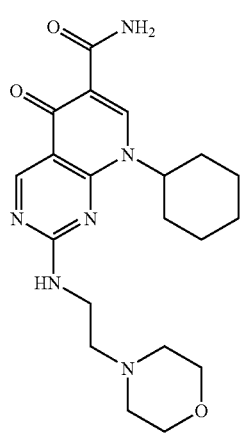
Cpd 39
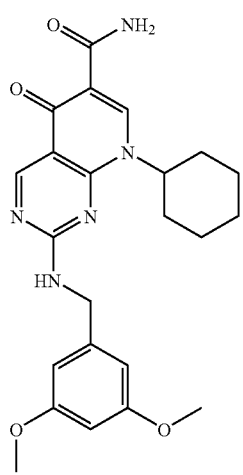
Cpd 40
-continued
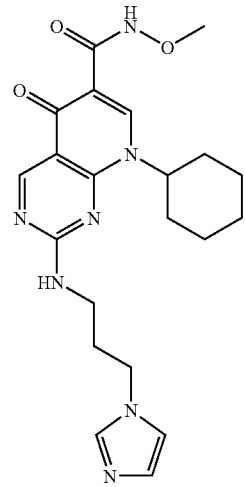
Cpd 41
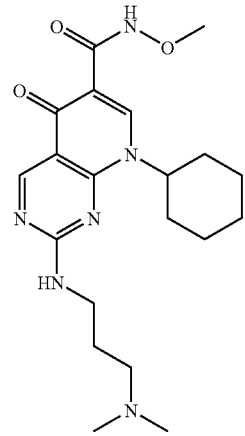
Cpd 42
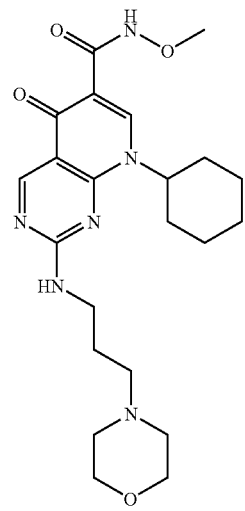
Cpd 43

Cpd 44
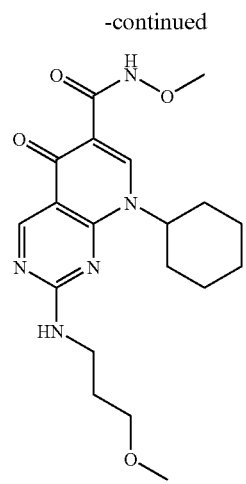
Cpd 45
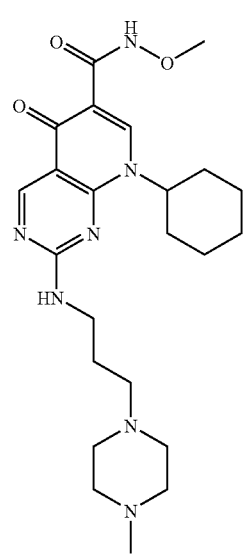
Cpd 46
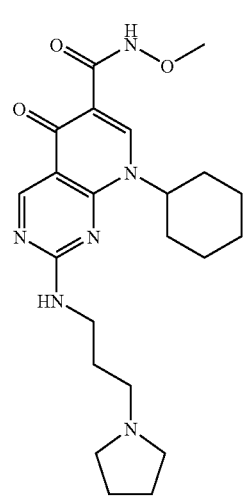
Cpd 47
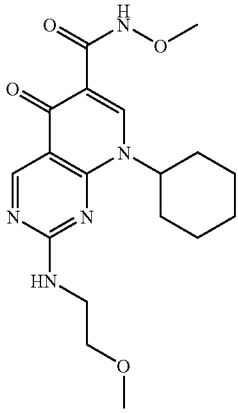
Cpd 48
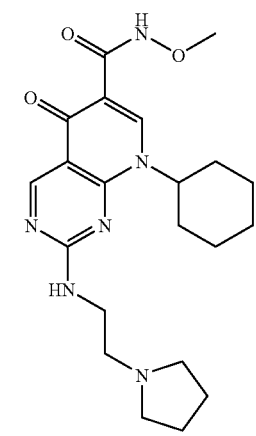
Cpd 49
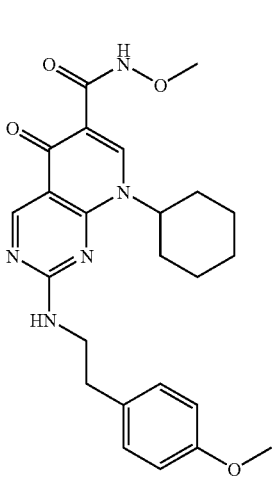

Cpd 50
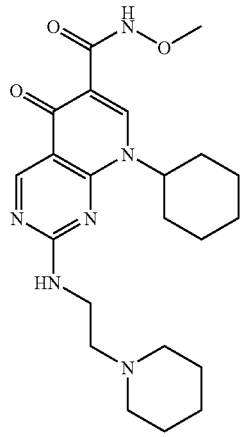
Cpd 53
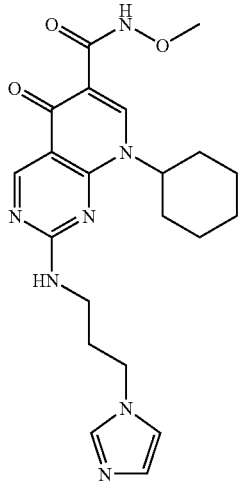
Cpd 51
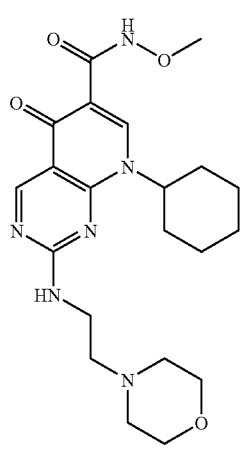
Cpd 54
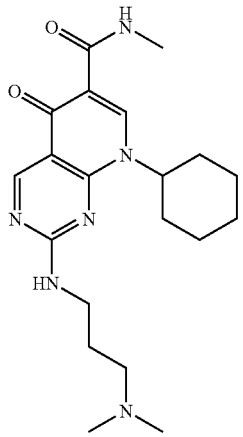
Cpd 52
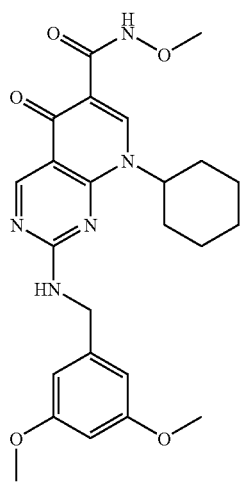
Cpd 55

-continued
Cpd 56
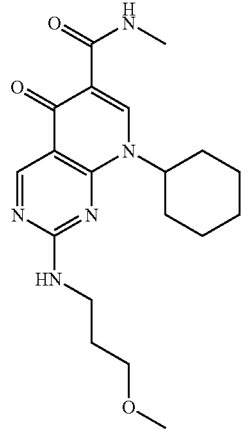
Cpd 57
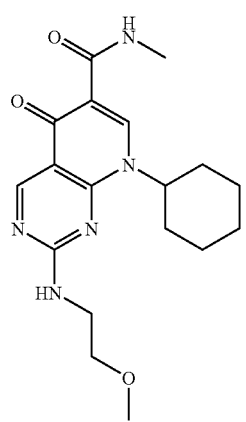
Cpd 58
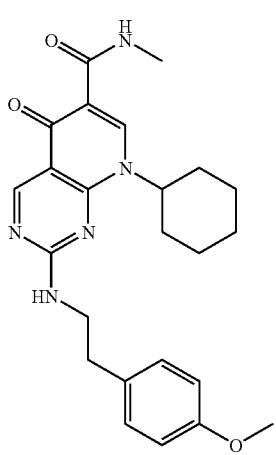
-continued
Cpd 59
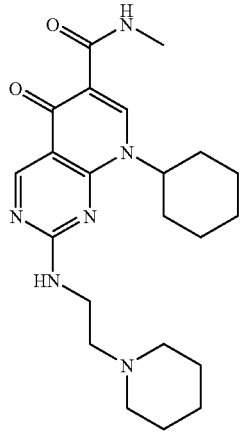
Cpd 60
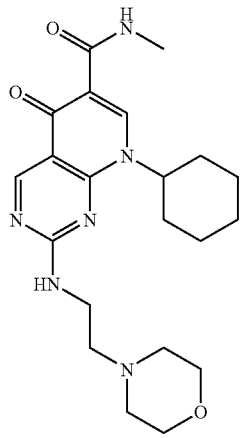
Cpd 61
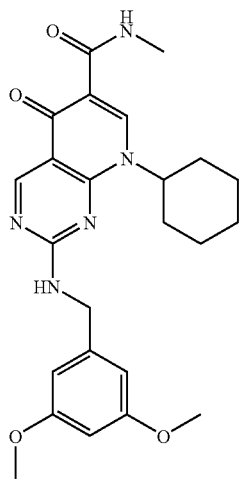
An example of the present invention is a compound of Formula I or a form thereof, selected from the group consisting of:
1  8-Indan-5-yl-2-[4-(4-methyl-piperazin-1-yl)-propylamino]-5-oxo-5,8-dihydro-pyrido[2,3-d]pyrimidine-6-carboxylic acid amide,
2  8-Indan-5-yl-5-oxo-2-(2-piperidin-1-yl-ethylamino)-5,8-dihydro-pyrido[2,3-d]pyrimidine-6-carboxylic acid amide, 3 2-(3-Imidazol-1-yl-propylamino)-8-indan-5-yl-5-oxo-5,8-dihydro-pyrido[2,3-d]pyrimidine-6-carboxylic acid amide, 4 8-Indan-5-yl-2-(2-morpholin-4-yl-ethylamino)-5-oxo-5,8-dihydro-pyrido[2,3-d]pyrimidine-6-carboxylic acid amide, 5 8-Indan-5-yl-2-(2-morpholin-4-yl-propylamino)-5-oxo-5,8-dihydro-pyrido[2,3-d]pyrimidine-6-carboxylic acid amide, 6 2-(3-Dimethylamino-propylamino)-8-indan-5-yl-5-oxo-5,8-dihydro-pyrido[2,3-d]pyrimidine-6-carboxylic acid amide, 7 8-Indan-5-yl-2-(3-methoxy-propylamino)-5-oxo-5,8-dihydro-pyrido[2,3-d]pyrimidine-6-carboxylic acid amide, 8 8-Indan-5-yl-5-oxo-2-[3-(2-oxo-pyrrolidin-1-yl)-propylamino]-5,8-dihydro-pyrido[2,3-d]pyrimidine-6-carboxylic acid amide, 9 8-Indan-5-yl-5-oxo-2-(3-pyrrolidin-1-yl-propylamino)-5,8-dihydro-pyrido[2,3-d]pyrimidine-6-carboxylic acid amide, 10 8-Indan-5-yl-2-(2-methoxy-ethylamino)-5-oxo-5,8-dihydro-pyrido[2,3-d]pyrimidine-6-carboxylic acid amide, 11 2-(3,5-Dimethoxy-benzylamino)-8-indan-5-yl-5-oxo-5,8-dihydro-pyrido[2,3-d]pyrimidine-6-carboxylic acid amide, 12 2-(3-Dimethylamino-propylamino)-8-indan-5-yl-5-oxo-5,8-dihydro-pyrido[2,3-d]pyrimidine-6-carboxylic acid methylamide, 13 8-Indan-5-yl-2-(3-morpholin-4-yl-propylamino)-5-oxo-5,8-dihydro-pyrido[2,3-d]pyrimidine-6-carboxylic acid methylamide, 14 8-Indan-5-yl-5-oxo-2-[3-(2-oxo-pyrrolidin-1-yl)-propylamino]-5,8-dihydro-pyrido[2,3-d]pyrimidine-6-carboxylic acid methylamide, 15 8-Indan-5-yl-2-[3-(4-methyl-piperazin-1-yl)-propylamino]-5-oxo-5,8-dihydro-pyrido[2,3-d]pyrimidine-6-carboxylic acid methylamide, 16 8-Indan-5-yl-2-(2-methoxy-ethylamino)-5-oxo-5,8-dihydro-pyrido[2,3-d]pyrimidine-6-carboxylic acid methylamide, 17 8-Indan-5-yl-2-[2-(4-methoxy-phenyl)-ethylamino]-5-oxo-5,8-dihydro-pyrido[2,3-d]pyrimidine-6-carboxylic acid methylamide, 18 8-Indan-5-yl-2-(2-morpholin-4-yl-ethylamino)-5-oxo-5,8-dihydro-pyrido[2,3-d]pyrimidine-6-carboxylic acid methylamide, 19 2-(3-Imidazol-1-yl-propylamino)-8-indan-5-yl-5-oxo-5,8-dihydro-pyrido[2,3-d]pyrimidine-6-carboxylic acid methoxy-amide, 20 2-(3-Dimethylamino-propylamino)-8-indan-5-yl-5-oxo-5,8-dihydro-pyrido[2,3-d]pyrimidine-6-carboxylic acid methoxy-amide, 21 8-Indan-5-yl-2-(3-methoxy-propylamino)-5-oxo-5,8-dihydro-pyrido[2,3-d]pyrimidine-6-carboxylic acid methoxy-amide, 22 8-Indan-5-yl-5-oxo-2-[3-(2-oxo-pyrrolidin-1-yl)-propylamino]-5,8-dihydro-pyrido[2,3-d]pyrimidine-6-carboxylic acid methoxy-amide, 23 8-Indan-5-yl-2-(2-methoxy-ethylamino)-5-oxo-5,8-dihydro-pyrido[2,3-d]pyrimidine-6-carboxylic acid methoxy-amide, 24 8-Indan-5-yl-2-[2-(4-methoxy-phenyl)-ethylamino]-5-oxo-5,8-dihydro-pyrido[2,3-d]pyrimidine-6-carboxylic acid methoxy-amide, 25 8-Indan-5-yl-5-oxo-2-(2-piperidin-1-yl-ethylamino)-5,8-dihydro-pyrido[2,3-d]pyrimidine-6-carboxylic acid methoxy-amide, 26 8-Indan-5-yl-2-(2-morpholin-4-yl-ethylamino)-5-oxo-5,8-dihydro-pyrido[2,3-d]pyrimidine-6-carboxylic acid methoxy-amide, 27 2-(3,5-Dimethoxy-benzylamino)-8-indan-5-yl-5-oxo-5,8-dihydro-pyrido[2,3-d]pyrimidine-6-carboxylic acid methoxy-amide, 28 8-Cyclohexyl-2-(3-imidazol-1-yl-propylamino)-5-oxo-5,8-dihydro-pyrido[2,3-d]pyrimidine-6-carboxylic acid amide, 29 8-Cyclohexyl-2-(3-dimethylamino-propylamino)-5-oxo-5,8-dihydro-pyrido[2,3-d]pyrimidine-6-carboxylic acid amide, 30 8-Cyclohexyl-2-(3-morpholin-4-yl-propylamino)-5-oxo-5,8-dihydro-pyrido[2,3-d]pyrimidine-6-carboxylic acid amide, 31 8-Cyclohexyl-2-(3-methoxy-propylamino)-5-oxo-5,8-dihydro-pyrido[2,3-d]pyrimidine-6-carboxylic acid amide, 32 8-Cyclohexyl-5-oxo-2-[3-(2-oxo-pyrrolidin-1-yl)-propylamino]-5,8-dihydro-pyrido[2,3-d]pyrimidine-6-carboxylic acid amide, 33 8-Cyclohexyl-2-[3-(4-methyl-piperazin-1-yl)-propylamino]-5-oxo-5,8-dihydro-pyrido[2,3-d]pyrimidine-6-carboxylic acid amide, 34 8-Cyclohexyl-5-oxo-2-(3-pyrrolidin-1-yl-propylamino)-5,8-dihydro-pyrido[2,3-d]pyrimidine-6-carboxylic acid amide, 35 8-Cyclohexyl-2-(2-methoxy-ethylamino)-5-oxo-5,8-dihydro-pyrido[2,3-d]pyrimidine-6-carboxylic acid amide, 36 8-Cyclohexyl-5-oxo-2-(2-pyrrolidin-1-yl-ethylamino)-5,8-dihydro-pyrido[2,3-d]pyrimidine-6-carboxylic acid amide, 37 8-Cyclohexyl-2-[2-(4-methoxy-phenyl)-ethylamino]-5-oxo-5,8-dihydro-pyrido[2,3-d]pyrimidine-6-carboxylic acid amide, 38 8-Cyclohexyl-5-oxo-2-(2-piperidin-1-yl-ethylamino)-5,8-dihydro-pyrido[2,3-d]pyrimidine-6-carboxylic acid amide, 39 8-Cyclohexyl-2-(2-morpholin-4-yl-ethylamino)-5-oxo-5,8-dihydro-pyrido[2,3-d]pyrimidine-6-carboxylic acid amide, 40 8-Cyclohexyl-2-(3,5-dimethoxy-benzylamino)-5-oxo-5,8-dihydro-pyrido[2,3-d]pyrimidine-6-carboxylic acid amide, 41 8-Cyclohexyl-2-(3-imidazol-1-yl-propylamino)-5-oxo-5,8-dihydro-pyrido[2,3-d]pyrimidine-6-carboxylic acid methoxy-amide, 42 8-Cyclohexyl-2-(3-dimethylamino-propylamino)-5-oxo-5,8-dihydro-pyrido[2,3-d]pyrimidine-6-carboxylic acid methoxy-amide, 43 8-Cyclohexyl-2-(3-morpholin-4-yl-propylamino)-5-oxo-5,8-dihydro-pyrido[2,3-d]pyrimidine-6-carboxylic acid methoxy-amide, 44 8-Cyclohexyl-2-(3-methoxy-propylamino)-5-oxo-5,8-dihydro-pyrido[2,3-d]pyrimidine-6-carboxylic acid methoxy-amide, 45 8-Cyclohexyl-2-[3-(4-methyl-piperazin-1-yl)-propylamino]-5-oxo-5,8-dihydro-pyrido[2,3-d]pyrimidine-6-carboxylic acid methoxy-amide, 46 8-Cyclohexyl-5-oxo-2-(3-pyrrolidin-1-yl-propylamino)-5,8-dihydro-pyrido[2,3-d]pyrimidine-6-carboxylic acid methoxy-amide, 47 8-Cyclohexyl-2-(2-methoxy-ethylamino)-5-oxo-5,8-dihydro-pyrido[2,3-d]pyrimidine-6-carboxylic acid methoxy-amide, 48 8-Cyclohexyl-5-oxo-2-(2-pyrrolidin-1-yl-ethylamino)-5,8-dihydro-pyrido[2,3-d]pyrimidine-6-carboxylic acid methoxy-amide, 49 8-Cyclohexyl-2-[2-(4-methoxy-phenyl)-ethylamino]-5-oxo-5,8-dihydro-pyrido[2,3-d]pyrimidine-6-carboxylic acid methoxy-amide, 50 8-Cyclohexyl-5-oxo-2-(2-piperidin-1-yl-ethylamino)-5,8-dihydro-pyrido[2,3-d]pyrimidine-6-carboxylic acid methoxy-amide, 51 8-Cyclohexyl-2-(2-morpholin-4-yl-ethylamino)-5-oxo-5,8-dihydro-pyrido[2,3-d]pyrimidine-6-carboxylic acid methoxy-amide, 52 8-Cyclohexyl-2-(3,5-dimethoxy-benzylamino)-5-oxo-5,8-dihydro-pyrido[2,3-d]pyrimidine-6-carboxylic acid methoxy-amide, 53 8-Cyclohexyl-2-(3-imidazol-1-yl-propylamino)-5-oxo-5,8-dihydro-pyrido[2,3-d]pyrimidine-6-carboxylic acid methylamide, 54 8-Cyclohexyl-2-(3-dimethylamino-propylamino)-5-oxo-5,8-dihydro-pyrido[2,3-d]pyrimidine-6-carboxylic acid methylamide, 55 8-Cyclohexyl-2-(3-morpholin-4-yl-propylamino)-5-oxo-5,8-dihydro-pyrido[2,3-d]pyrimidine-6-carboxylic acid methylamide, 56 8-Cyclohexyl-2-(3-methoxy-propylamino)-5-oxo-5,8-dihydro-pyrido[2,3-d]pyrimidine-6-carboxylic acid methylamide, 57 8-Cyclohexyl-2-(2-methoxy-ethylamino)-5-oxo-5,8-dihydro-pyrido[2,3-d]pyrimidine-6-carboxylic acid methylamide, 58 8-Cyclohexyl-2-[2-(4-methoxy-phenyl)-ethylamino]-5-oxo-5,8-dihydro-pyrido[2,3-d]pyrimidine-6-carboxylic acid methylamide, 59 8-Cyclohexyl-5-oxo-2-(2-piperidin-1-yl-ethylamino)-5,8-dihydro-pyrido[2,3-d]pyrimidine-6-carboxylic acid methylamide, 60 8-Cyclohexyl-2-(2-morpholin-4-yl-ethylamino)-5-oxo-5,8-dihydro-pyrido[2,3-d]pyrimidine-6-carboxylic acid methylamide, and 61 8-Cyclohexyl-2-(3,5-dimethoxy-benzylamino)-5-oxo-5,8-dihydro-pyrido[2,3-d]pyrimidine-6-carboxylic acid methylamide.

The invention also relates to methods of inhibiting protein tyrosine kinase activity in a mammal by administration of a therapeutically effective amount of at least one compound of Formula I. A preferred tyrosine kinase is c-fms.

The compounds of the present invention are further useful as markers for the c-fms receptor. Compounds of formula (I) when used as markers are for example radio-labeled by for example, substituting at least one hydrogen atom with a tritium atom. Other labeling techniques known in the arts can also be used.

An aspect of the use for a compound of Formula (I) includes use of an instant compound as a marker, wherein the compound is labeled with a ligand such as a radioligand (selected from deuterium, tritium and the like).

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The invention is considered to include the tautomeric forms of all compounds of Formula I. In addition, for chiral embodiments of the invention, the invention is considered to include pure enantiomers, racemic mixtures, as well as mixtures of enantiomers having 0.001% to 99.99% enantiomeric excess. In addition, some of the compounds represented by Formula I may be prodrugs, i.e., derivatives of a drug that possess superior delivery capabilities and therapeutic value as compared to the active drug. Prodrugs are transformed into active drugs by in vivo enzymatic or chemical processes.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(masslevorotatory)}{(massdextrotatory) + (masslevorotatory)} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrotatory} = \frac{(massdextrotatory)}{(massdextrotatory) + (masslevorotatory)} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

Chemical Nomenclature and Definitions

Bond lines drawn into a ring system from a substituent variable indicate that the substituent may be attached to any of the substitutable ring atoms.

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

DEFINITIONS

The term "alkyl" refers to both linear and branched chain radicals of up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, and isohexyl. The term "$C_{(x-y)}$alkyl" refers to an alkyl chain of length not less than x carbons and not more than y carbons. For example, the term $C_{(1-4)}$alkyl refers to both linear and branched chain radicals of up to 4 carbon atoms. Alkyl radicals or linking groups may be attached to a core molecule via a terminal carbon atom or via a carbon atom within the chain. Similarly, substituent variables may be attached to an alkyl linking group when allowed by available valences.

The term "amino" refers to an amine group of the formula: —$NH_2$.

The term "dialkylamino" refers to an amino with two alkyl substituents, wherein the amino group is the point of attachment to the rest of the molecule.

The term "alkoxyalkyl" refers to at least one alkoxy group bonded to any carbon atom along an alkyl chain. The term "alkoxyalkyl" has the same definition as "alkylether".

The term "aryl" refers to monocyclic or bicyclic aromatic ring systems containing from 6 to 12 carbons in the ring. Alkyl substituents may optionally be present on the ring. Examples include benzene, biphenyl and naphthalene (also referred to as naphthalenyl), azulenyl, anthracenyl and the like. Aryl radicals may be attached to a core molecule and further substituted on any atom when allowed by available valences.

The term "aromatic" refers to a cycloalkylic hydrocarbon ring system having an unsaturated, conjugated π electron system.

The term "alkoxy" refers to a saturated branched or straight chain monovalent hydrocarbon alcohol radical derived by the removal of the hydrogen atom from the hydroxide oxygen substituent on a parent alkane, as in the formula: —O—$C_{1-8}$alkyl. Examples include methoxy, ethoxy, propoxy, isopropoxy and butoxy. The term "$C_{(x-y)}$alkoxy" refers to an alkoxy chain of length not less than x carbons and not more than y carbons. For example, the term $C_{(1-4)}$alkoxy refers to both linear and branched alkoxy chain radicals of up to 4 carbon atoms. An alkoxy radical may be attached to a core molecule and further substituted when allowed by available valences.

The term "arylcycloalkyl" refers to a $C_{8-10}$ fused bicyclic ring system comprising an aryl group and a cycloalkyl group in which the point of attachment is the aryl group, as in a benzofused $C_{3-14}$cycloalkyl ring system defined below. Examples include, but are not limited to, 1H-indenyl, indanyl, and 1,2,3,4-tetrahydro-naphthalenyl.

The term "cycloalkyl" refers to a saturated or partially unsaturated ring composed of from 3 to 14 carbon atoms. Up to four alkyl substituents may optionally be present on the ring. The term also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{8-10}$cycloalkyl, $C_{9-13}$cycloalkyl, $C_{3-14}$cycloalkyl or benzofused $C_{3-14}$cycloalkyl ring system. Examples include 1,1-dimethyl-cyclobutyl, 1,2,3-trimethylcyclopentyl, cyclopropyl, cyclobutyl, cyclopentyl, cyclohexyl, cyclohexyl and cyclohexenyl, cycloheptyl, cyclooctyl, 1H-indenyl, indanyl, 9H-fluorenyl, 1,2,3,4-tetrahydro-naphthalenyl, acenaphthenyl, bicyclo[2.2.1]heptenyl and the like. $C_{3-14}$cycloalkyl radicals may be attached to a core molecule and further substituted on any atom when allowed by available valences.

The term "cycloalkylaryl" refers to a $C_{8-10}$ fused bicyclic ring system comprising an aryl group and a cycloalkyl group in which the point of attachment is the cycloalkyl group, as in a benzofused $C_{3-14}$cycloalkyl ring system defined above, such as 1H-indenyl, indanyl, 1,2,3,4-tetrahydro-naphthalenyl and the like.

The term "bicycloalkyl" refers to a saturated or partially unsaturated fused ring pair composed of from 8 to 10 carbon atoms. Up to four alkyl substituents may optionally be present on the ring. Examples include adamantanyl, bicyclo[2.2.1]heptyl, decahydro-naphthalenyl and 1,2,3,4-tetrahydro-pentalenyl and the like. Bicycloalkyl radicals may be attached to a core molecule and further substituted on any atom when allowed by available valences.

The term "hetero" used as a prefix for a ring system refers to the replacement of at least one ring carbon atom with one or more heteroatoms independently selected from N, S, or O. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein one heteroatom is nitrogen and the other is one heteroatom selected from N, S or O.

The term "heterocyclyl" refers to a nonaromatic (i.e. saturated or partially unsaturated) ring composed of from 3 to 7 carbon atoms and at least one heteroatom selected from N, O or S. Alkyl substituents and/or carbonyl substituents may optionally be present on the ring. Examples include tetrahydrofuranyl, dihydropyranyl, piperidinyl, 2,5-dimethypiperidinyl, morpholinyl, piperazinyl, thiomorpholinyl, 2H-pyrrole, pyrrolidinyl, pyrrolinyl, pyrazolidinyl, pyrazolinyl, oxazolidinyl, pyrrolidinyl, imidazolidinyl, imidazolinyl (also referred to as 4,5-dihydro-1H-imidazolyl), 1,3-dioxolanyl, tetrazolinyl, tetrazolidinyl, 1,4-dioxanyl, 1,4-dithianyl, azetidinyl, azepanyl, hexahydro-1,4-diazepinyl, hexahydro-1,4-oxazepanyl, tetrahydro-thienyl, tetrahydro-pyranyl, tetrahydro-pyridazinyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like. Heterocyclyl radicals may be attached to a core molecule and further substituted on any atom when allowed by available valences.

The term "heteroaryl" refers to 5- to 7-membered mono- or 8- to 10-membered bicyclic aromatic ring systems, any ring of which may consist of from one to four heteroatoms selected from N, O, S, S(O) or $SO_2$ where the nitrogen and sulfur atoms can exist in any allowed oxidation state. Examples include benzoimidazolyl, benzothiazolyl, benzothienyl, benzoxazolyl, furanyl, imidazolyl, isothiazolyl, isoxazolyl, oxazolyl, pyrazinyl, pyrazolyl, pyridinyl, pyrimidinyl, pyrrolyl, quiilolinyl, thiazolyl, thienyl, oxadiazolyl, triazolyl, thiadiazolyl, pyridazinyl, indolizinyl, indolyl, azaindolyl, isoindolyl, benzofuranyl, indazolyl, azaindazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Heteroaryl radicals may be attached to a core molecule and further substituted on any atom when allowed by available valences.

The term "heteroatom" refers to a nitrogen atom, an oxygen atom or a sulfur atom wherein the nitrogen and sulfur atoms can exist in any allowed oxidation states.

The term "halogen" or "halo" means the group fluoro, chloro, bromo or iodo.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, ovarian cancer, uterine cancer, breast cancer, colon cancer, stomach cancer, hairy cell leukemia and non-small lung carcinoma. In one embodiment of the invention, an effective amount of at least one compound of Formula I is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I. Examples of diseases that may be effectively treated include atherosclerosis, cardiac hypertrophy, glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. A preferred dosage is 5 mg/kg, delivered orally. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

A representative compound of Formula (I) or a form thereof for use in the therapeutic methods and pharmaceutical compositions, medicines or medicaments described herein includes a compound selected from the group consisting of:

1  8-Indan-5-yl-2-[4-(4-methyl-piperazin-1-yl)-propylamino]-5-oxo-5,8-dihydro-pyrido[2,3-d]pyrimidine-6-carboxylic acid amide,
3  2-(3-Imidazol-1-yl-propylamino)-8-indan-5-yl-5-oxo-5,8-dihydro-pyrido[2,3-d]pyrimidine-6-carboxylic acid amide,
4  8-Indan-5-yl-2-(2-morpholin-4-yl-ethylamino)-5-oxo-5,8-dihydro-pyrido[2,3-d]pyrimidine-6-carboxylic acid amide,
5  8-Indan-5-yl-2-(2-morpholin-4-yl-propylamino)-5-oxo-5,8-dihydro-pyrido[2,3-d]pyrimidine-6-carboxylic acid amide,
6  2-(3-Dimethylamino-propylamino)-8-indan-5-yl-5-oxo-5,8-dihydro-pyrido[2,3-d]pyrimidine-6-carboxylic acid amide,
7  8-Indan-5-yl-2-(3-methoxy-propylamino)-5-oxo-5,8-dihydro-pyrido[2,3-d]pyrimidine-6-carboxylic acid amide,
8  8-Indan-5-yl-5-oxo-2-[3-(2-oxo-pyrrolidin-1-yl)-propylamino]-5,8-dihydro-pyrido[2,3-d]pyrimidine-6-carboxylic acid amide,
9  8-Indan-5-yl-5-oxo-2-(3-pyrrolidin-1-yl-propylamino)-5,8-dihydro-pyrido[2,3-d]pyrimidine-6-carboxylic acid amide,
10  8-Indan-5-yl-2-(2-methoxy-ethylamino)-5-oxo-5,8-dihydro-pyrido[2,3-d]pyrimidine-6-carboxylic acid amide,
11  2-(3,5-Dimethoxy-benzylamino)-8-indan-5-yl-5-oxo-5,8-dihydro-pyrido[2,3-d]pyrimidine-6-carboxylic acid amide,
19  2-(3-Imidazol-1-yl-propylamino)-8-indan-5-yl-5-oxo-5,8-dihydro-pyrido[2,3-d]pyrimidine-6-carboxylic acid methoxy-amide,
20  2-(3-Dimethylamino-propylamino)-8-indan-5-yl-5-oxo-5,8-dihydro-pyrido[2,3-d]pyrimidine-6-carboxylic acid methoxy-amide,
21  8-Indan-5-yl-2-(3-methoxy-propylamino)-5-oxo-5,8-dihydro-pyrido[2,3-d]pyrimidine-6-carboxylic acid methoxy-amide,
22  8-Indan-5-yl-5-oxo-2-[3-(2-oxo-pyrrolidin-1-yl)-propylamino]-5,8-dihydro-pyrido[2,3-d]pyrimidine-6-carboxylic acid methoxy-amide,
23  8-Indan-5-yl-2-(2-methoxy-ethylamino)-5-oxo-5,8-dihydro-pyrido[2,3-d]pyrimidine-6-carboxylic acid methoxy-amide,
24  8-Indan-5-yl-2-[2-(4-methoxy-phenyl)-ethylamino]-5-oxo-5,8-dihydro-pyrido[2,3-d]pyrimidine-6-carboxylic acid methoxy-amide,
26  8-Indan-5-yl-2-(2-morpholin-4-yl-ethylamino)-5-oxo-5,8-dihydro-pyrido[2,3-d]pyrimidine-6-carboxylic acid methoxy-amide,
27  2-(3,5-Dimethoxy-benzylamino)-8-indan-5-yl-5-oxo-5,8-dihydro-pyrido[2,3-d]pyrimidine-6-carboxylic acid methoxy-amide,
28  8-Cyclohexyl-2-(3-imidazol-1-yl-propylamino)-5-oxo-5,8-dihydro-pyrido[2,3-d]pyrimidine-6-carboxylic acid amide,
29  8-Cyclohexyl-2-(3-dimethylamino-propylamino)-5-oxo-5,8-dihydro-pyrido[2,3-d]pyrimidine-6-carboxylic acid amide,
30  8-Cyclohexyl-2-(3-morpholin-4-yl-propylamino)-5-oxo-5,8-dihydro-pyrido[2,3-d]pyrimidine-6-carboxylic acid amide,
31  8-Cyclohexyl-2-(3-methoxy-propylamino)-5-oxo-5,8-dihydro-pyrido[2,3-d]pyrimidine-6-carboxylic acid amide,
32  8-Cyclohexyl-5-oxo-2-[3-(2-oxo-pyrrolidin-1-yl)-propylamino]-5,8-dihydro-pyrido[2,3-d]pyrimidine-6-carboxylic acid amide,
33  8-Cyclohexyl-2-[3-(4-methyl-piperazin-1-yl)-propylamino]-5-oxo-5,8-dihydro-pyrido[2,3-d]pyrimidine-6-carboxylic acid amide,
34  8-Cyclohexyl-5-oxo-2-(3-pyrrolidin-1-yl-propylamino)-5,8-dihydro-pyrido[2,3-d]pyrimidine-6-carboxylic acid amide,
35  8-Cyclohexyl-2-(2-methoxy-ethylamino)-5-oxo-5,8-dihydro-pyrido[2,3-d]pyrimidine-6-carboxylic acid amide,
36  8-Cyclohexyl-5-oxo-2-(2-pyrrolidin-1-yl-ethylamino)-5,8-dihydro-pyrido[2,3-d]pyrimidine-6-carboxylic acid amide,
37  8-Cyclohexyl-2-[2-(4-methoxy-phenyl)-ethylamino]-5-oxo-5,8-dihydro-pyrido[2,3-d]pyrimidine-6-carboxylic acid amide,
38  8-Cyclohexyl-5-oxo-2-(2-piperidin-1-yl-ethylamino)-5,8-dihydro-pyrido[2,3-d]pyrimidine-6-carboxylic acid amide,
39  8-Cyclohexyl-2-(2-morpholin-4-yl-ethylamino)-5-oxo-5,8-dihydro-pyrido[2,3-d]pyrimidine-6-carboxylic acid amide,
40  8-Cyclohexyl-2-(3,5-dimethoxy-benzylamino)-5-oxo-5,8-dihydro-pyrido[2,3-d]pyrimidine-6-carboxylic acid amide,
41  8-Cyclohexyl-2-(3-imidazol-1-yl-propylamino)-5-oxo-5,8-dihydro-pyrido[2,3-d]pyrimidine-6-carboxylic acid methoxy-amide,
42  8-Cyclohexyl-2-(3-dimethylamino-propylamino)-5-oxo-5,8-dihydro-pyrido[2,3-d]pyrimidine-6-carboxylic acid methoxy-amide,
43  8-Cyclohexyl-2-(3-morpholin-4-yl-propylamino)-5-oxo-5,8-dihydro-pyrido[2,3-d]pyrimidine-6-carboxylic acid methoxy-amide,
44  8-Cyclohexyl-2-(3-methoxy-propylamino)-5-oxo-5,8-dihydro-pyrido[2,3-d]pyrimidine-6-carboxylic acid methoxy-amide,
45  8-Cyclohexyl-2-[3-(4-methyl-piperazin-1-yl)-propylamino]-5-oxo-5,8-dihydro-pyrido[2,3-d]pyrimidine-6-carboxylic acid methoxy-amide, 46 8-Cyclohexyl-5-oxo-2-(3-pyrrolidin-1-yl-propylamino)-5,8-dihydro-pyrido[2,3-d]pyrimidine-6-carboxylic acid methoxy-amide, 47 8-Cyclohexyl-2-(2-methoxy-ethylamino)-5-oxo-5,8-dihydro-pyrido[2,3-d]pyrimidine-6-carboxylic acid methoxy-amide, 49 8-Cyclohexyl-2-[2-(4-methoxy-phenyl)-ethylamino]-5-oxo-5,8-dihydro-pyrido[2,3-d]pyrimidine-6-carboxylic acid methoxy-amide, 51 8-Cyclohexyl-2-(2-morpholin-4-yl-ethylamino)-5-oxo-5,8-dihydro-pyrido[2,3-d]pyrimidine-6-carboxylic acid methoxy-amide, and 52 8-Cyclohexyl-2-(3,5-dimethoxy-benzylamino)-5-oxo-5,8-dihydro-pyrido[2,3-d]pyrimidine-6-carboxylic acid methoxy-amide.

General Synthetic Methods

The compounds of Formula I can be prepared by methods known to those skilled in the art. The following reaction schemes are only meant to represent general, illustrative examples of the invention and are in no way meant to limit the invention.

The following general reaction schemes display various methods of preparing the compounds of Formula I. It is recognized by those skilled in the art that some compounds of Formula I may be further derivatized to provide additional embodiments of the invention. Representative compounds prepared by such derivatizations appear in schemes I and II.

A typical preparation of compounds of the present invention is shown in Scheme I. An amine is reacted with ethyl 3-chloropropionate at elevated temperature in the presence of an inorganic base and a catalytic amount of tetrabutylammonium bromide to afford the aminopropionate ester 1-1. The amine is reacted with ethyl 4-chloro-2-methylthio-5-pyrimidinecarboxylate to produce the corresponding 4-substituted aminopyrimidine 1-2. Cyclization of this diester under Dieckmann conditions affords the bicyclic compound 1-3. Subsequent halogenation with bromine followed by dehydrohalogenation gives the unsaturated 1-4 (Eur J Med Chem 9 (2000) pp 585-590). The methylthio group is oxidized to the sulfone 1-5, which is subsequently replaced with an amine by nucleophilic substitution. The resulting carboxylic ester 1-6 is converted to the carboxylic acid 1-7 via basic hydrolysis. The carboxylic acid 1-7 is reacted with an amine under normal coupling conditions to form the corresponding amide 1-8. The amide 1-8 may also be prepared directly from the ester 1-6 when the amine $R_1$—$NH_2$ is ammonia, or an alkylamine.

Scheme I

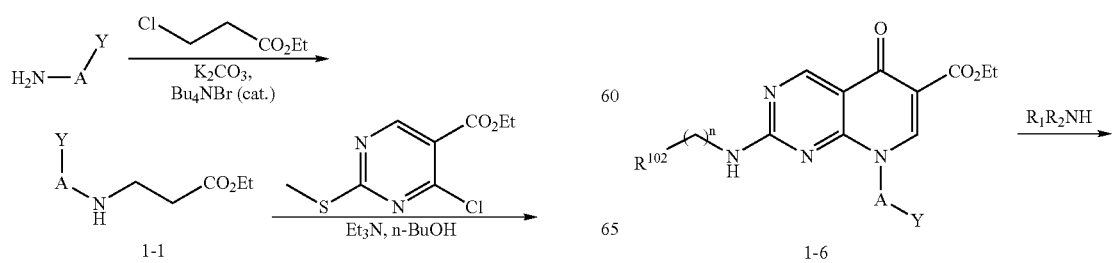

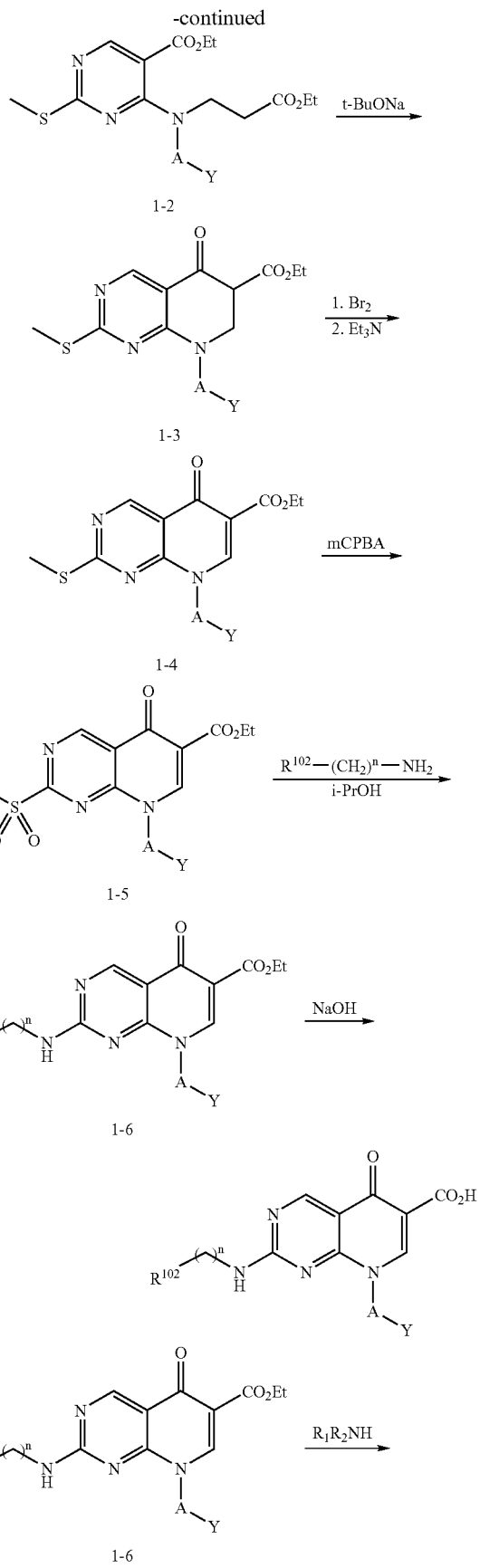

-continued

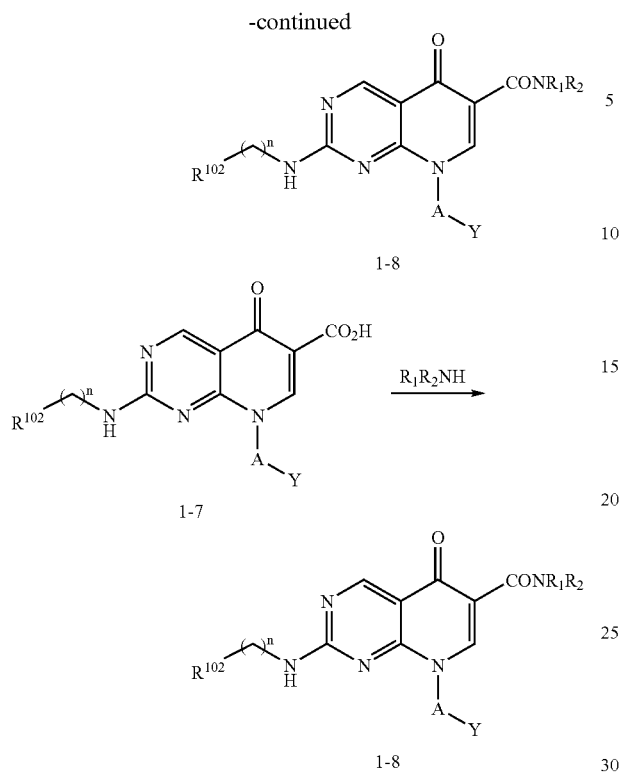

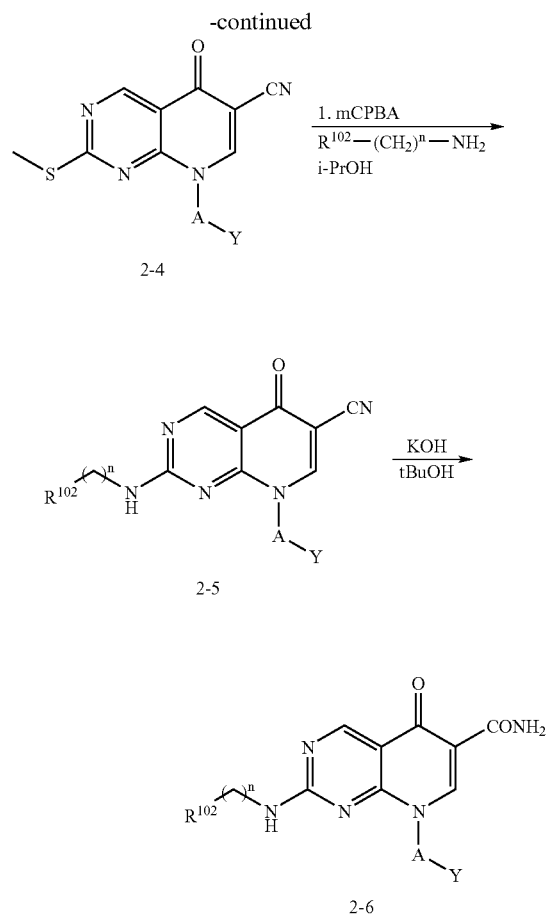

The synthesis is further extended to include the preparation of 5,8-dihydro-pyrido[2,3-d]pyrimidines with a carbonitrile functional group at the $C_6$ position. The method of preparation is identical with that used for preparing the esters (Scheme I) except that suitably 3-substituted aminopropionitriles 2-1 are used in the first step (Scheme II). Hydrolysis of 2-5 under basic conditions provides the corresponding primary amide 2-6.

When the 6-amide is the desired product, the intermediate 1-3 is converted to the primary amide 3-1 using liquid ammonia in a pressure bottle (Scheme III). Subsequent oxidation to methyl sulfone and nuclear substitution by an amine provides the desired 6-amide analogs 2-6.

Scheme II

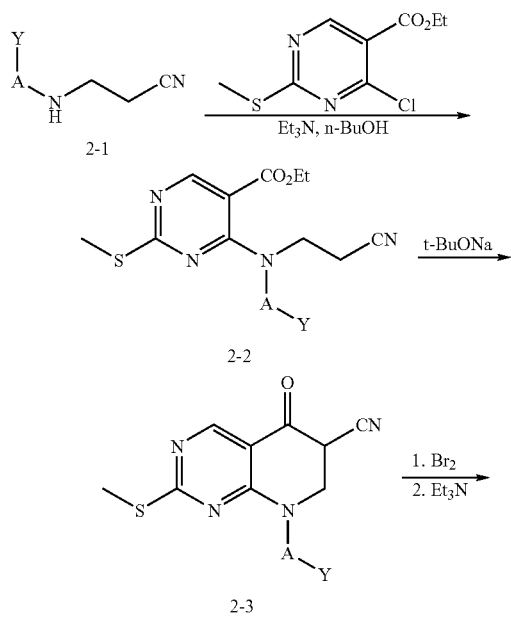

Scheme III

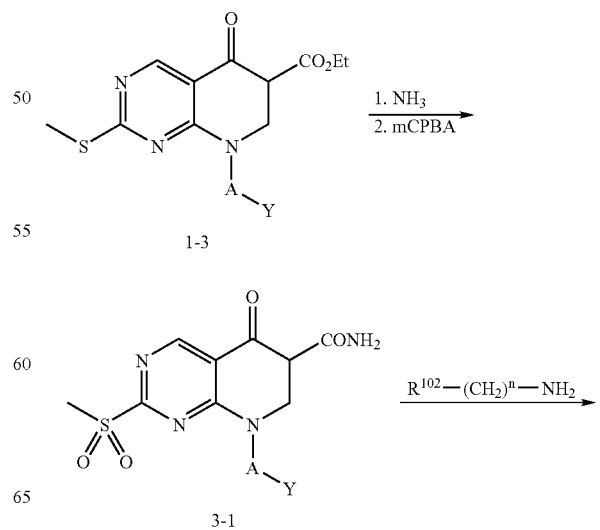

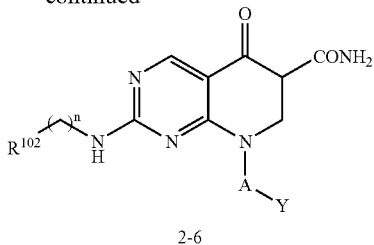

2-6

Example 1

8-Indan-5-yl-2-[4-(4-methyl-piperazin-1-yl)-propylamino]-5-oxo-5,8-dihydro-pyrido[2,3-d]pyrimidine-6-carboxylic acid amide (Cpd 1)

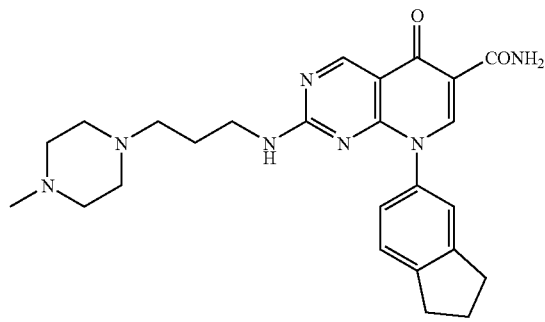

Step A. 3-(Indan-5-ylamino)-propionic acid ethyl ester

To a mixture of 5-aminoindane (5 g, 37.6 mmol), ethyl 3-chloropropionate (4.7 mL, 37.6 mmol) and potassium carbonate (5.2 g, 37.6 mmol) was added tetrabutylammonium bromide (200 mg). The mixture was stirred at 100° C. for 16 hours. After cooling to room temperature (rt), the mixture was extracted into ethyl acetate (EtOAc), washed with water, brine and then dried with sodium sulfate ($Na_2SO_4$). Removal of the solvent and chromatography on silica, eluting with EtOAc/hexanes (1:20-1:10, v/v), gave 6.2 g (71%) of the title compound. $^1$H NMR (300 MHz, $CDCl_3$) δ (ppm): 7.03 (d, J=7.6 Hz, 1H), 6.55 (s, 1H), 6.43 (d, J=7.6 Hz, 1H), 4.15 (q, 2H), 3.86 (br, 1H), 3.43 (t, 2H), 2.82 (m, 4H), 2.60 (t, 2H), 2.06 (m, 2H), 1.27 (t, 3H).

Step B. 4-[(2-Ethoxycarbonyl-ethyl)-indan-5-ylamino]-2-methylsulfanyl-pyrimidine-5-carboxylic acid ethyl ester To a solution of 3-(indan-5-ylamino)-propionic acid ethyl ester (5 g, 21.4 mmol) and ethyl 4-chloro-2-methylthio-5-pyrimidinecarboxylate (5 g, 21.4 mmol) in 40 mL of n-butanol was added triethylamine (3 mL, 21.4 mmol). The solution was stirred at rt for 2 days. The solvent was removed under vacuum. The residue was extracted into EtOAc, washed with water, brine and then dried with $Na_2SO_4$. Removal of the solvent and chromatography on silica, eluting with EtOAc/hexanes (1:10-1:6, v/v), gave 8.2 g (90%) of the titled compound as a white solid. $^1$H NMR (300 MHz, $CDCl_3$) δ (ppm): 8.22 (s, 1H), 7.16 (d, J=7.6 Hz, 1H), 6.95 (s, 1H), 6.87 (d, J=7.6 Hz, 1H), 4.35 (t, 2H), 3.55 (q, 2H), 2.82 (m, 4H), 2.69 (t, 2H), 2.58 (s, 3H), 2.06 (m, 2H), 1.20 (t, 3H), 1.02 (t, 3H).

Step C. 8-Indan-5-yl-2-methylsulfanyl-5-oxo-5,6,7,8-tetrahydro-pyrido[2,3-d]pyrimidine-6-carboxylic acid ethyl ester To sodium (25 wt % dispersion in paraffin wax, 1.6 g, 16.9 mmol) was added t-butanol (30 mL) under stirring and $N_2$. After 10 minutes, a solution of 4-[(2-ethoxycarbonyl-ethyl)-indan-5-yl-amino]-2-methylsulfanyl-pyrimidine-5-carboxylic acid ethyl ester (6.6 g, 15.4 mmol) in 40 mL of toluene was added to the sodium t-butoxide solution. The mixture was then heated at 90° C. for 30 minutes. The solution was cooled and poured into crushed ice. The solution was adjusted to pH 7 using HCl solution. The precipitates were extracted into EtOAc twice. The solvent was evaporated under vacuum and the product (bright yellow solid, 4 g, 62%) was recrystallized from isopropanol. $^1$H NMR (300 MHz, $CDCl_3$) indicated that the presence of both enol and keto forms in a 4:1 ratio.

Step D. 8-Indan-5-yl-2-methylsulfanyl-5-oxo-5,8-dihydro-pyrido[2,3-d]pyrimidine-6-carboxylic acid ethyl ester To a solution of 8-indan-5-yl-2-methylsulfanyl-5-oxo-5,6,7,8-tetrahydro-pyrido[2,3-d]pyrimidine-6-carboxylic acid ethyl ester (0.32 g, 0.84 mmol) in 5 mL of methylene chloride ($CH_2Cl_2$) was added bromine (43 µL, 0.84 mmol) slowly under $N_2$. The solution was stirred at room temperature for 2 hours (or to completion). The solvent was removed under vacuum without heating. The residue was redissolved in 2 mL of $CH_2Cl_2$, and was added triethylamine (234 µL, 1.68 mmol) in 1 mL of $CH_2Cl_2$. The solution was stirred at rt for 4 hours. The progress of the reaction was monitored by LC-MS. The solvent was evaporated and the residue was applied onto a silica gel column. The product was eluted with EtOAc/hexanes (1:5-1:2.5, v/v) and obtained as a white solid (0.30 g, 94%). $^1$H NMR (300 MHz, $CDCl_3$) δ (ppm): 9.42 (s, 1H), 8.59 (s, 1H), 7.37 (d, J=7.8 Hz, 1H), 7.24 (s, 1H), 7.16 (d, J=7.8 Hz, 1H), 4.40 (q, 2H), 3.00 (m, 4H), 2.35 (s, 3H), 2.10 (m, 2H), 1.40 (t, 3H).

Step E. 8-Indan-5-yl-2-methanesulfonyl-5-oxo-5,8-dihydro-pyrido[2,3-d]pyrimidine-6-carboxylic acid ethyl ester To a solution of 8-indan-5-yl-2-methylsulfanyl-5-oxo-5,8-dihydro-pyrido[2,3-d]pyrimidine-6-carboxylic acid ethyl ester (0.3 g, 0.79 mmol) in 5 mL of $CH_2Cl_2$, was added 3-chloroperoxybenzoic acid (m-CPBA, 69.5%, 431 mg, 1.73 mmol) portionwise. The solution was stirred at room temperature for 3 hours. An aqueous solution of 10% sodium thiosulfate was added to quench the reaction. After 30 minutes saturated sodium bicarbonate solution was added, and the aqueous solution was extracted with $CH_2Cl_2$. The combined $CH_2Cl_2$ fractions were washed with brine and dried over $Na_2SO_4$. Removal of the solvent and chromatography on silica, eluting with EtOAc/hexanes (1:3-1:1.6, v/v) gave 0.22 g (67%) of the title compound as an off-white solid. $^1$H NMR (300 MHz, $CDCl_3$) δ (ppm): 9.75 (s, 1H), 8.70 (s, 1H), 7.39 (d, J=7.8 Hz, 1H), 7.24 (s, 1H), 7.16 (d, J=7.8 Hz, 1H), 4.38 (q, 2H), 3.19 (s, 3H), 3.00 (m, 4H), 2.10 (m, 2H), 1.40 (t, 3H).

Step F. 8-Indan-5-yl-2-[4-(4-methyl-piperazin-1-yl)-propylamino]-5-oxo-5,8-dihydro-pyrido[2,3-d]pyrimidine-6-carboxylic acid ethyl ester The title compound was prepared from a solution of 4-(4-methyl-piperazin-1-yl)-propylamine (6 µL, 0.036 mmol) and 8-indan-5-yl-2-methanesulfonyl-5-oxo-5,8-dihydro-pyrido[2,3-d]pyrimidine-6-carboxylic acid ethyl ester (from Example 1 Step E, 15 mg, 0.036 mmol). in 1 mL of isopropanol heated to 90° C. for 1 hour. The solvent was evaporated and the residue was re-dissolved in a mixture of methanol and $CH_2Cl_2$ (1:1, v/v) and applied onto a prep-TLC plate (2000 micro). The plate was developed in $NH_4OH/MeOH/CH_2Cl_2$ (1:9:90, v/v). 15.9 mg of 8-indan-5-yl-2-[4-(4-methyl-piperazin-1-yl)-propylamino]-5-oxo-5,8-dihydro-pyrido[2,3-d]pyrimidine-6-carboxylic acid ethyl ester was obtained as a white solid. $^1$H NMR (300 MHz, $CDCl_3$) δ (ppm): 9.22 (s, 1H), 8.45 (s, 1H), 7.32 (d, 1H), 7.15 (m, 3H), 6.66 (br, 1H), 4.38 (q, 2H), 3.20 (m, 2H), 3.00 (m, 4H), 2.20-2.52 (m, 15H), 1.62 (m, 2H), 1.40 (t, 3H). Mass Spectrum (LCMS, ESI pos.) Calcd. For $C_{27}H_{34}N_6O_3$: 491.27 (M+H). Found: 491.4.

Step G. 8-Indan-5-yl-2-[4-(4-methyl-piperazin-1-yl)-propylamino]-5-oxo-5,8-dihydro-pyrido[2,3-d]pyrimidine-6-carboxylic acid amide To a solution of 8-indan-5-yl-2-[4-(4-methyl-piperazin-1-yl)-propylamino]-5-oxo-5,8-dihydro-pyrido[2,3-d]pyrimidine-6-carboxylic acid ethyl ester (7.1 mg, 0.013 mmol) in 1 mL of methanol was bubbled ammonia at −78° C. for 5 minutes in a pressure bottle (10 mL). The bottle was capped and warmed to room temperature and stirred for 16 hours. The solvent was evaporated to leave a white solid of 8-indan-5-yl-2-[4-(4-methyl-piperazin-1-yl)-propylamino]-5-oxo-5,8-dihydro-pyrido[2,3-d]pyrimidine-6-carboxylic acid amide (4.3 mg, 75%). $^1$H NMR (400 MHz, $CD_2Cl_2$) δ (ppm): 9.45 (br, 1H), 9.21 (s, 1H), 8.73 (s, 1H), 7.38 (d, J=7.8 Hz, 1H), 7.19 (m, 2H), 6.00 (br, 1H), 3.25 (br, 2H), 2.40-3.20 (m, 16H), 2.18 (m, 2H). Mass Spectrum (LCMS, ESI pos.) Calcd. For $C_{25}H_{31}N_7O_2$: 462.25 (M+H). Found: 462.2.

Example 2

8-Indan-5-yl-5-oxo-2-(2-piperidin-1-yl-ethylamino)-5,8-dihydro-pyrido[2,3-d]pyrimidine-6-carboxylic acid amide (Cpd 2)

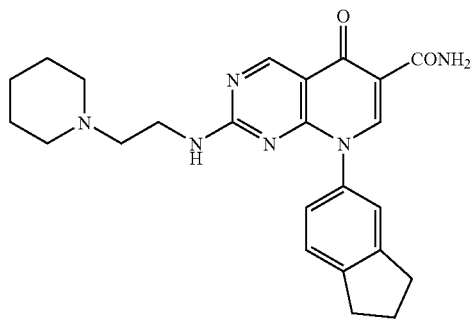

Step A. 8-Indan-5-yl-5-oxo-2-(2-piperidin-1-yl-ethylamino)-5,8-dihydro-pyrido[2,3-d]pyrimidine-6-carboxylic acid ethyl ester Using the procedure outlined in Example 1(Step F) the title compound was prepared from 2-piperidin-1-yl-ethylamine (5.2 µL, 0.036 mmol) and 8-indan-5-yl-2-methanesulfonyl-5-oxo-5,8-dihydro-pyrido[2,3-d]pyrimidine-6-carboxylic acid ethyl ester (from Example 1(Step E), 15 mg, 0.036 mmol). 6.6 mg of 8-indan-5-yl-5-oxo-2-(2-piperidin-1-yl-ethylamino)-5,8-dihydro-pyrido[2,3-d]pyrimidine-6-carboxylic acid ethyl ester was obtained as a white solid. $^1$H NMR (300 MHz, $CDCl_3$) δ (ppm): 9.22 (s, 1H), 8.45 (s, 1H), 7.32 (d, 1H), 7.22 (s, 1H), 7.15 (d, 1H), 6.22 (br, 1H), 4.36 (q, 2H), 3.22 (m, 2H), 3.00 (m, 4H), 2.10-2.60 (m, 8H), 1.60 (m, 6H), 1.40 (t, 3H). Mass Spectrum (LCMS, ESI pos.) Calcd. For $C_{26}H_{31}N_5O_3$: 462.24 (M+H). Found: 462.4.

Step B. 8-Indan-5-yl-5-oxo-2-(2-piperidin-1-yl-ethylamino)-5,8-dihydro-pyrido[2,3-d]pyrimidine-6-carboxylic acid amide Using the procedure described in Example 1, Step G, the title compound was prepared from 8-indan-5-yl-5-oxo-2-(2-piperidin-1-yl-ethylamino)-5,8-dihydro-pyrido[2,3-d]pyrimidine-6-carboxylic acid ethyl ester (4 mg, 0.009 mmol). 8-Indan-5-yl-5-oxo-2-(2-piperidin-1-yl-ethylamino)-5,8-dihydro-pyrido[2,3-d]pyrimidine-6-carboxylic acid amide was obtained as a white solid (3.6 mg, 90%). $^1$H NMR (300 MHz, $CD_2Cl_2$) δ (ppm): 9.51 (br, 1H), 9.22 (s, 1H), 8.71 (s, 1H), 7.37 (d, J=7.7 Hz, 1H), 7.26 (s, 1H), 7.18 (d, J=7.7 Hz, 1H), 6.03 (br, 1H), 3.26 (m, 2H), 2.99 (m, 4H), 2.10-2.60 (m, 8H), 1.55 (m, 6H). Mass Spectrum (LCMS, ESI pos.) Calcd. For $C_{24}H_{28}N_6O_2$: 433.23 (M+H). Found: 433.2.

Example 3

2-(3-Imidazol-1-yl-propylamino)-8-indan-5-yl-5-oxo-5,8-dihydro-pyrido[2,3-d]pyrimidine-6-carboxylic acid amide (Cpd 3)

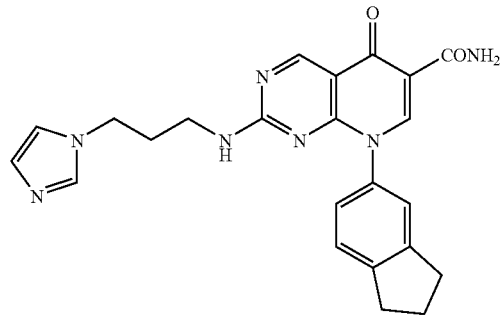

Step A. 2-(3-Imidazol-1-yl-propylamino)-8-indan-5-yl-5-oxo-5,8-dihydro-pyrido[2,3-d]pyrimidine-6-carboxylic acid ethyl ester Using the procedure outlined in Example 1(Step F) the title compound was prepared from 3-imidazol-1-yl-propylamine (4.4 µL, 0.036 mmol) and 8-indan-5-yl-2-methanesulfonyl-5-oxo-5,8-dihydro-pyrido[2,3-d]pyrimidine-6-carboxylic acid ethyl ester (from Example 1(Step E), 15 mg, 0.036 mmol). 19.2 mg of 2-(3-imidazol-1-yl-propylamino)-8-indan-5-yl-5-oxo-5,8-dihydro-pyrido[2,3-d]pyrimidine-6-carboxylic acid ethyl ester was obtained as a white solid. $^1$H NMR (300 MHz, $CDCl_3$) δ (ppm): 9.22 (s, 1H), 8.45 (s, 1H), 7.50 (br, 1H), 7.32 (d, 1H), 7.22 (s, 1H), 7.15 (d, 1H), 7.03 (br, 1H), 6.78 (br, 1H), 6.10 (br, 1H), 4.36 (q, 2H), 3.75 (m, 2H), 3.10 (m, 2H), 2.97 (m, 4H), 2.14 (m, 2H), 1.92 (m, 2H), 1.40

(t, 3H). Mass Spectrum (LCMS, ESI pos.) Calcd. For $C_{25}H_{26}N_6O_3$: 459.21 (M+H). Found: 459.4.

Step B. 2-(3-Imidazol-1-yl-propylamino)-8-indan-5-yl-5-oxo-5,8-dihydro-pyrido[2,3-d]pyrimidine-6-carboxylic acid amide Using the procedure described in Example 1, Step G, the title compound was prepared from 2-(3-imidazol-1-yl-propylamino)-8-indan-5-yl-5-oxo-5,8-dihydro-pyrido[2,3-d]pyrimidine-6-carboxylic acid ethyl ester (Example 3, 13 mg, 0.028 mmol). 2-(3-Imidazol-1-yl-propylamino)-8-indan-5-yl-5-oxo-5,8-dihydro-pyrido[2,3-d]pyrimidine-6-carboxylic acid amide was obtained as a white solid (10.9 mg, 91%). $^1$H NMR (400 MHz, $CD_2Cl_2/CD_3OD$ (20:1 v/v)) δ (ppm): 9.14 (s, 1H), 8.65 (s, 1H), 7.28 (br, 2H), 7.16 (s, 1H), 7.07 (d, 1H), 6.88 (br, 1H), 6.71 (s, 1H), 3.68 (m, 2H), 3.07 (m, 2H), 2.88 (m, 4H), 2.06 (m, 2H), 1.82 (m, 2H). Mass Spectrum (LCMS, ESI pos.) Calcd. For $C_{23}H_{23}N_7O_2$: 430.19 (M+H). Found: 430.2.

Example 4

8-Indan-5-yl-2-(2-morpholin-4-yl-ethylamino)-5-oxo-5,8-dihydro-pyrido[2,3-d]pyrimidine-6-carboxylic acid amide (Cpd 4)

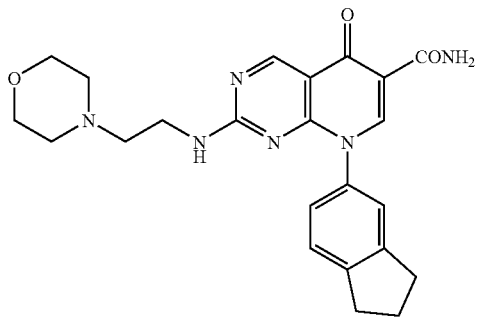

Step A. 8-Indan-5-yl-2-(2-morpholin-4-yl-ethylamino)-5-oxo-5,8-dihydro-pyrido[2,3-d]pyrimidine-6-carboxylic acid ethyl ester Using the procedure outlined in Example 1(Step F) the title compound was prepared from 2-morpholin-4-yl-ethylamine (4.8 μL, 0.036 mmol) and 8-indan-5-yl-2-methanesulfonyl-5-oxo-5,8-dihydro-pyrido[2,3-d]pyrimidine-6-carboxylic acid ethyl ester (from Example 1(Step E), 15 mg, 0.036 mmol). 15.5 mg of 8-indan-5-yl-2-(2-morpholin-4-yl-ethylamino)-5-oxo-5,8-dihydro-pyrido[2,3-d]pyrimidine-6-carboxylic acid ethyl ester was obtained as a white solid. $^1$H NMR (400 MHz, $CDCl_3$) δ (ppm): 9.24 (s, 1H), 8.45 (s, 1H), 7.34 (d, 1H), 7.22 (s, 1H), 7.15 (d, 1H), 6.19 (br, 1H), 4.36 (q, 2H), 3.65 (m, 4H), 3.24 (m, 2H), 2.99 (m, 4H), 2.30-2.60 (m, 6H), 2.17 (m, 2H), 1.37 (t, 3H). Mass Spectrum (LCMS, ESI pos.) Calcd. For $C_{25}H_{29}N_5O_4$: 464.22 (M+H). Found: 464.4.

Step B. 8-Indan-5-yl-2-(2-morpholin-4-yl-ethylamino)-5-oxo-5,8-dihydro-pyrido[2,3-d]pyrimidine-6-carboxylic acid amide Using the procedure described in Example 1, Step G, the title compound was prepared from 8-indan-5-yl-2-(2-morpholin-4-yl-ethylamino)-5-oxo-5,8-dihydro-pyrido[2,3-d]pyrimidine-6-carboxylic acid ethyl ester (Example 4, 11 mg, 0.024 mmol). 8-Indan-5-yl-2-(2-morpholin-4-yl-ethylamino)-5-oxo-5,8-dihydro-pyrido[2,3-d]pyrimidine-6-carboxylic acid amide was obtained as a white solid (9.9 mg, 95%). $^1$H NMR (400 MHz, $CD_2Cl_2/CD_3OD$ (20:1 v/v)) δ (ppm): 9.22 (s, 1H), 8.71 (s, 1H), 7.34 (d, J=7.8 Hz, 1H), 7.25 (s, 1H), 7.18 (d, J=7.8 Hz, 1H), 3.62 (m, 4H), 3.28 (m, 2H), 2.99 (m, 4H), 2.42 (m, 4H), 2.32 (br, 4H), 2.17 (m, 2H). Mass Spectrum (LCMS, ESI pos.) Calcd. For $C_{23}H_{26}N_6O_3$: 435.21 (M+H). Found: 435.2.

Example 5

8-Indan-5-yl-2-(2-morpholin-4-yl-propylamino)-5-oxo-5,8-dihydro-pyrido[2,3-d]pyrimidine-6-carboxylic acid amide (Cpd 5)

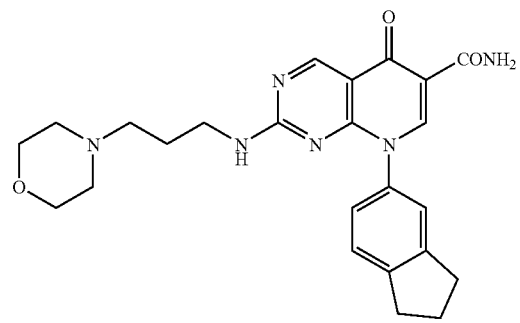

Step A. 8-Indan-5-yl-2-(2-morpholin-4-yl-propylamino)-5-oxo-5,8-dihydro-pyrido[2,3-d]pyrimidine-6-carboxylic acid ethyl ester Using the procedure outlined in Example 1(Step F) the title compound was prepared from 2-morpholin-4-yl-propylamine (5.3 μL, 0.036 mmol) and 8-indan-5-yl-2-methanesulfonyl-5-oxo-5,8-dihydro-pyrido[2,3-d]pyrimidine-6-carboxylic acid ethyl ester (from Example 1(Step E), 15 mg, 0.036 mmol). 17.2 mg of 8-indan-5-yl-2-(2-morpholin-4-yl-propylamino)-5-oxo-5,8-dihydro-pyrido[2,3-d]pyrimidine-6-carboxylic acid ethyl ester was obtained as a white solid. $^1$H NMR (400 MHz, $CDCl_3$) δ (ppm): 9.26 (s, 1H), 8.46 (s, 1H), 7.02-7.40 (m, 3H), 6.64 (br, 1H), 4.35 (q, 2H), 3.71 (m, 4H), 3.22 (m, 2H), 2.98 (m, 4H), 2.38 (m, 6H), 2.17 (m, 2H), 1.67 (m, 2H), 1.37 (t, 3H). Mass Spectrum (LCMS, ESI pos.) Calcd. For $C_{26}H_{31}N_5O_4$: 478.24 (M+H). Found: 478.4.

Step B. 8-Indan-5-yl-2-(2-morpholin-4-yl-propylamino)-5-oxo-5,8-dihydro-pyrido[2,3-d]pyrimidine-6-carboxylic acid amide Using the procedure described in Example 1, Step G, the title compound was prepared from 8-indan-5-yl-2-(2-morpholin-4-yl-propylamino)-5-oxo-5,8-dihydro-pyrido[2,3-d]pyrimidine-6-carboxylic acid ethyl ester (Example 5, 10.6 mg, 0.022 mmol). 8-Indan-5-yl-2-(2-morpholin-4-yl-propylamino)-5-oxo-5,8-dihydro-pyrido[2,3-d]pyrimidine-6-carboxylic acid amide was obtained as a white solid (10 mg, 100%). $^1$H NMR (400 MHz, $CD_2Cl_2/CD_3OD$ (20:1 v/v)) δ (ppm): 9.20 (s, 1H), 8.72 (s, 1H), 7.37 (d, J=7.9 Hz, 1H), 7.26 (s, 1H), 7.18 (d, J=7.9 Hz, 1H), 3.66 (m, 4H), 3.21 (m, 4H), 2.88 (m, 4H), 2.38 (m, 2H), 2.17 (m, 2H), 1.61 (m, 2H). Mass Spectrum (LCMS, ESI pos.) Calcd. For $C_{24}H_{28}N_6O_3$: 449.22 (M+H). Found: 449.2.

Example 6

2-(3-Dimethylamino-propylamino)-8-indan-5-yl-5-oxo-5,8-dihydro-pyrido[2,3-d]pyrimidine-6-carboxylic acid amide (Cpd 6)

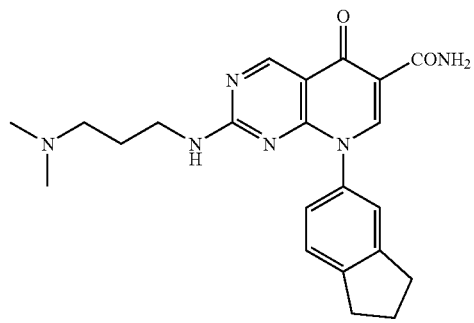

Step A. 2-(3-Dimethylamino-propylamino)-8-indan-5-yl-5-oxo-5,8-dihydro-pyrido[2,3-d]pyrimidine-6-carboxylic acid ethyl ester Using the procedure outlined in Example 1(Step F) the title compound was prepared from N1,N1-dimethyl-propane-1,3-diamine (4.6 µL, 0.036 mmol) and 8-indan-5-yl-2-methanesulfonyl-5-oxo-5,8-dihydro-pyrido[2,3-d]pyrimidine-6-carboxylic acid ethyl ester (from Example 1(Step E), 15 mg, 0.036 mmol). 9.7 mg of 2-(3-dimethylamino-propylamino)-8-indan-5-yl-5-oxo-5,8-dihydro-pyrido[2,3-d]pyrimidine-6-carboxylic acid ethyl ester was obtained as a white solid. $^1$H NMR (400 MHz, CDCl$_3$) δ (ppm): 9.23 (s, 1H), 8.46 (s, 1H), 7.34 (d, 1H), 7.23 (s, 1H), 7.13 (d, 1H), 6.77 (br, 1H), (m, 2H), 2.99 (m, 4H), 2.19 (m, 10H), 1.60 (m, 2H), 1.37 (t, 3H). Mass Spectrum (LCMS, ESI pos.) Calcd. For C$_{24}$H$_{29}$N$_5$O$_3$: 436.23 (M+H). Found: 436.4.

Step B. 2-(3-Dimethylamino-propylamino)-8-indan-5-yl-5-oxo-5,8-dihydro-pyrido[2,3-d]pyrimidine-6-carboxylic acid amide Using the procedure described in Example 1, Step G, the title compound was prepared from 2-(3-dimethylamino-propylamino)-8-indan-5-yl-5-oxo-5,8-dihydro-pyrido[2,3-d]pyrimidine-6-carboxylic acid ethyl ester (Example 6, 6 mg, 0.014 mmol). 2-(3-Dimethylamino-propylamino)-8-indan-5-yl-5-oxo-5,8-dihydro-pyrido[2,3-d]pyrimidine-6-carboxylic acid amide was obtained as a white solid (5.2 mg, 92%). $^1$H NMR (400 MHz, CD$_2$Cl$_2$/CD$_3$OD (20:1 v/v)) δ (ppm): 9.21 (s, 1H), 8.72 (s, 1H), 7.35 (d, J=7.8 Hz, 1H), 7.27 (s, 1H), 7.16 (d, J=7.8 Hz, 1H), 3.20 (m, 2H), 3.00 (m, 10H), 1.61 (m, 2H). Mass Spectrum (LCMS, ESI pos.) Calcd. For C$_{22}$H$_{26}$N$_6$O$_2$: 407.21 (M+H). Found: 407.2.

Example 7

8-Indan-5-yl-2-(3-methoxy-propylamino)-5-oxo-5,8-dihydro-pyrido[2,3-d]pyrimidine-6-carboxylic acid amide (Cpd 7)

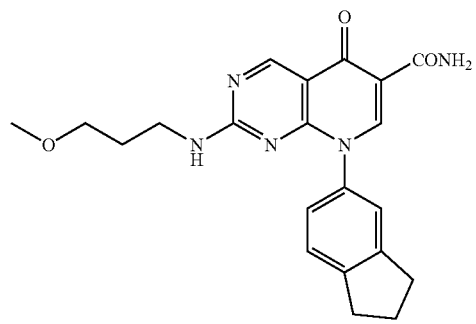

Step A. 8-Indan-5-yl-2-(3-methoxy-propylamino)-5-oxo-5,8-dihydro-pyrido[2,3-d]pyrimidine-6-carboxylic acid ethyl ester Using the procedure outlined in Example 1 Step F, the title compound was prepared from 3-methoxy-propylamine and 8-indan-5-yl-2-methanesulfonyl-5-oxo-5,8-dihydro-pyrido[2,3-d]pyrimidine-6-carboxylic acid ethyl ester (from Example 1(Step E), 20 mg, 0.040 mmol). 11 mg of 8-Indan-5-yl-2-(3-methoxy-propylamino)-5-oxo-5,8-dihydro-pyrido[2,3-d]pyrimidine-6-carboxylic acid ethyl ester was obtained as a white solid. $^1$H NMR (400 MHz, CDCl$_3$) δ (ppm): 9.24 (s, 1H), 8.47 (s, 1H), 7.34 (d, J=8.0 Hz, 1H), 7.23 (s, 1H), 7.15 (d, J=8.0 Hz, 1H), 6.01 (br, 1H), 4.37 (q, J=7.1 Hz, 2H), 3.34 (t, J=5.7 Hz, 2H), 3.29 (s, 3H), 3.24 (q, J=6.1 Hz, 2H), 2.99 (m, 4H), 2.18 (m, 2H), 1.71 (m, 2H), 1.38 (t, J=7.1 Hz, 3H).

Step B. 8-Indan-5-yl-2-(3-methoxy-propylamino)-5-oxo-5,8-dihydro-pyrido[2,3-d]pyrimidine-6-carboxylic acid amide Using the procedure outlined in Example 1 Step G, the title compound was prepared from 8-indan-5-yl-2-(3-methoxy-propylamino)-5-oxo-5,8-dihydro-pyrido[2,3-d]pyrimidine-6-carboxylic acid ethyl ester (4.0 mg, 0.08 mmol). 8-Indan-5-yl-2-(3-methoxy-propylamino)-5-oxo-5,8-dihydro-pyrido[2,3-d]pyrimidine-6-carboxylic acid amide was obtained as a white solid (2.8 mg, 70%). $^1$H NMR (400 MHz, CDCl$_3$) δ (ppm): 9.55 (br, 1H), 9.28 (s, 1H), 8.78 (s, 1H), 7.32 (d, J=7.8 Hz, 1H), 7.23 (s, 1H), 7.16 (d, J=7.8 Hz, 1H), 6.13 (br, 1H), 5.71 (br, 1H), 3.37 (t, J=5.9 Hz, 2H), 3.30 (s, 3H), 3.27 (m, 2H), 2.98 (m, 4H), 2.18 (m, 2H), 1.74 (m, 2H). Mass Spectrum (LCMS, ESI pos.) Calcd. For C$_{21}$H$_{23}$N$_5$O$_3$: 394.18 (M+H). Found: 394.1.

Example 8

8-Indan-5-yl-5-oxo-2-[3-(2-oxo-pyrrolidin-1-yl)-propylamino]-5,8-dihydro-pyrido[2,3-d]pyrimidine-6-carboxylic acid amide (Cpd 8)

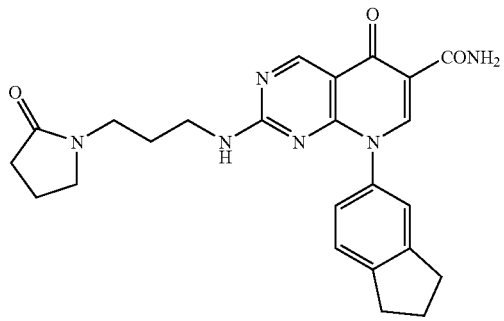

Step A. 8-Indan-5-yl-5-oxo-2-[3-(2-oxo-pyrrolidin-1-yl)-propylamino]-5,8-dihydro-pyrido[2,3-d]pyrimidine-6-carboxylic acid ethyl ester Using the procedure outlined in Example 1 Step F, the title compound was prepared from 1-(3-amino-propyl)-pyrrolidin-2-one and 8-indan-5-yl-2-methanesulfonyl-5-oxo-5,8-dihydro-pyrido[2,3-d]pyrimidine-6-carboxylic acid ethyl ester (from Example 1(Step E) 25 mg, 0.052 mmol). 17 mg of 8-Indan-5-yl-5-oxo-2-[3-(2-oxo-pyrrolidin-1-yl)-propylamino]-5,8-dihydro-pyrido[2,3-d]pyrimidine-6-carboxylic acid ethyl ester was obtained as a white solid. $^1$H NMR (400 MHz, CDCl$_3$) δ (ppm): 9.25 (s, 1H), 8.46 (s, 1H), 7.33 (d, J=7.7 Hz, 1H), 7.23 (s, 1H), 7.16 (d, J=7.7 Hz, 1H), 6.26 (br, 1H), 4.37 (q, J=7.3 Hz, 2H), 3.36 (m, 2H), 3.27 (m, 2H), 3.00 (m, 4H), 2.37 (t, J=7.9 Hz, 2H), 2.18 (m, 2H), 2.00 (m, 2H), 1.60 (m, 4H), 1.38 (t, J=7.3 Hz).

Step B. 8-Indan-5-yl-5-oxo-2-[3-(2-oxo-pyrrolidin-1-yl)-propylamino]-5,8-dihydro-pyrido[2,3-d]pyrimidine-6-carboxylic acid amide Using the procedure described in Example 1 Step G, the title compound was prepared from 8-indan-5-yl-5-oxo-2-[3-(2-oxo-pyrrolidin-1-yl)-propylamino]-5,8-dihydro-pyrido[2,3-d]pyrimidine-6-carboxylic acid ethyl ester (2.0 mg, 0.004 mmol). 8-Indan-5-yl-2-(3-methoxy-propylamino)-5-oxo-5,8-dihydro-pyrido[2,3-d]pyrimidine-6-carboxylic acid amide was obtained as a white solid (1.5 mg, 77%). $^1$H NMR (400 MHz, CDCl$_3$) δ (ppm): 9.54 (br, 1H), 9.27 (s, 1H), 8.76 (s, 1H), 7.30 (d, J=7.7 Hz, 1H), 7.21 (s, 1H), 7.14, (d, J=7.7 Hz, 1H), 6.43 (br, 1H), 5.70 (br, 1H), 3.36 (m, 2H), 3.27 (m, 2H), 2.98 (m, 4H), 2.34 (t, J=7.9 Hz, 2H), 2.16 (m, 2H), 2.00 (m, 2H), 1.60 (m, 4H). Mass Spectrum (LCMS, ESI pos.) Calcd. For C$_{24}$H$_{26}$N$_6$O$_3$: 447.21 (M+H). Found: 447.2.

Example 9

8-Indan-5-yl-5-oxo-2-(3-pyrrolidin-1-yl-propylamino)-5,8-dihydro-pyrido[2,3-d]pyrimidine-6-carboxylic acid amide (Cpd 9)

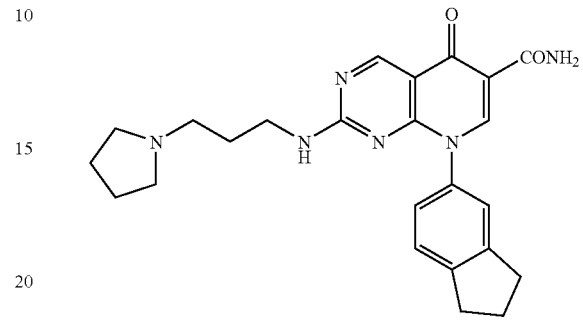

Step A. 8-Indan-5-yl-5-oxo-2-(3-pyrrolidin-1-yl-propylamino)-5,8-dihydro-pyrido[2,3-d]pyrimidine-6-carboxylic acid ethyl ester Using the procedure described in Example 1 Step F, the title compound was prepared from 3-pyrrolidin-1-yl-propylamine and 8-indan-5-yl-2-methanesulfonyl-5-oxo-5,8-dihydro-pyrido[2,3-d]pyrimidine-6-carboxylic acid ethyl ester (from Example 1(Step E), 10 mg, 0.022 mmol). 7 mg of 8-Indan-5-yl-5-oxo-2-(3-pyrrolidin-1-yl-propylamino)-5,8-dihydro-pyrido[2,3-d]pyrimidine-6-carboxylic acid ethyl ester was obtained as a white solid. $^1$H NMR (400 MHz, CDCl$_3$) δ (ppm): 9.24 (s, 1H), 8.76 (s, 1H), 7.30 (d, J=7.7 Hz, 1H), 7.21 (s, 1H), 7.14 (d, J=7.7 Hz, 1H), 5.72 (br, 1H), 4.36 (q, J=7.1 Hz, 2H), 3.27 (m, 2H), 2.98 (m, 4H), 2.50 (m, 6H), 2.17 (m, 2H), 1.80 (m, 4H), 1.68 (m, 2H), 1.38 (t, J=7.1 Hz, 3H).

Step B. 8-Indan-5-yl-5-oxo-2-(3-pyrrolidin-1-yl-propylamino)-5,8-dihydro-pyrido[2,3-d]pyrimidine-6-carboxylic acid amide Using the procedure outlined in Example 1 Step G, the title compound was prepared from 8-indan-5-yl-5-oxo-2-(3-pyrrolidin-1-yl-propylamino)-5,8-dihydro-pyrido[2,3-d]pyrimidine-6-carboxylic acid ethyl ester (6.0 mg, 0.012 mmol). 8-Indan-5-yl-2-(3-methoxy-propylamino)-5-oxo-5,8-dihydro-pyrido[2,3-d]pyrimidine-6-carboxylic acid amide was obtained as a white solid (4.2 mg, 70%). $^1$H NMR (400 MHz, CDCl$_3$) δ (ppm): 9.55 (br, 1H), 9.26 (s, 1H), 8.76 (s, 1H), 7.30 (d, J=7.7 Hz, 1H), 7.21 (s, 1H), 7.14 (d, J=7.7 Hz, 1H), 6.83 (br, 1H), 5.72 (br, 1H), 3.27 (m, 2H), 2.98 (m, 4H), 2.50 (m, 6H), 2.17 (m, 2H), 1.80 (m, 4H), 1.68 (m, 2H). Mass Spectrum (LCMS, ESI pos.) Calcd. For C$_{24}$H$_{28}$N$_6$O$_2$: 433.23 (M+H). Found: 433.2.

Example 10

8-Indan-5-yl-2-(2-methoxy-ethylamino)-5-oxo-5,8-dihydro-pyrido[2,3-d]pyrimidine-6-carboxylic acid amide (Cpd 10)

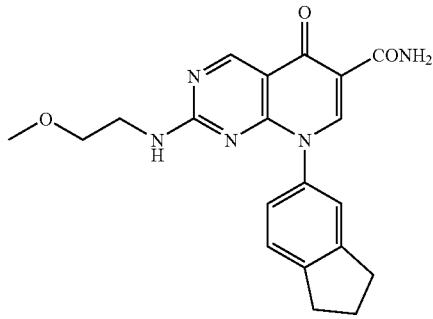

Step A. 8-Indan-5-yl-2-(2-methoxy-ethylamino)-5-oxo-5,8-dihydro-pyrido[2,3-d]pyrimidine-6-carboxylic acid ethyl ester Using the procedure outlined in Example 1 Step F, the title compound was prepared from 2-methoxy-ethylamine and 8-indan-5-yl-2-methanesulfonyl-5-oxo-5,8-dihydro-pyrido[2,3-d]pyrimidine-6-carboxylic acid ethyl ester (Example 1, Step E, 10 mg, 0.022 mmol). 7 mg of 8-indan-5-yl-2-(2-methoxy-ethylamino)-5-oxo-5,8-dihydro-pyrido[2,3-d]pyrimidine-6-carboxylic acid ethyl ester was obtained as a white solid. $^1$H NMR (400 MHz, CDCl$_3$) δ (ppm): 9.25 (s, 1H), 8.47 (s, 1H), 7.35 (d, J=7.8 Hz, 1H), 7.22 (s, 1H), 7.14 (d, J=7.8 Hz, 1H), 5.99 (br, 2H), 4.37 (q, J=7.1 Hz, 2H), 3.45-3.35 (m, 2H), 3.29 (s, 3H), 3.00 (m, 4H), 2.18 (m, 2H), 1.38 (t, J=7.1 Hz, 3H).

Step B. 8-Indan-5-yl-2-(2-methoxy-ethylamino)-5-oxo-5,8-dihydro-pyrido[2,3-d]pyrimidine-6-carboxylic acid amide Using the procedure outlined in Example 1 Step G, the title compound was prepared from 8-indan-5-yl-2-(2-methoxy-ethylamino)-5-oxo-5,8-dihydro-pyrido[2,3-d]pyrimidine-6-carboxylic acid ethyl ester (3.0 mg, 0.008 mmol). 8-Indan-5-yl-2-(2-methoxy-ethylamino)-5-oxo-5,8-dihydro-pyrido[2,3-d]pyrimidine-6-carboxylic acid amide was obtained as a white solid (2.3 mg, 80%). $^1$H NMR (400 MHz, CDCl$_3$) δ (ppm): 9.55 (br, 1H), 9.29 (s, 1H), 8.77 (s, 1H), 7.32 (d, J=7.8 Hz, 1H), 7.23 (s, 1H), 7.16 (d, J=7.8 Hz, 1H), 5.74 (br, 2H), 3.45-3.35 (m, 2H), 3.30 (s, 3H), 2.99 (m, 4H), 2.17 (m, 2H). Mass Spectrum (LCMS, ESI pos.) Calcd. For C$_{20}$H$_{22}$N$_5$O$_3$: 380.16 (M+H). Found: 380.1.

Example 11

2-(3,5-Dimethoxy-benzylamino)-8-indan-5-yl-5-oxo-5,8-dihydro-pyrido[2,3-d]pyrimidine-6-carboxylic acid amide (Cpd 11)

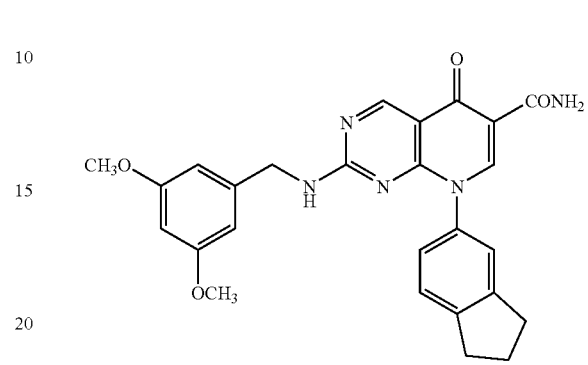

Step A. 2-(3,5-Dimethoxy-benzylamino)-8-indan-5-yl-5-oxo-5,8-dihydro-pyrido[2,3-d]pyrimidine-6-carboxylic acid ethyl ester Using the procedure outlined in Example 1 Step F, the title compound was prepared from 3,5-dimethoxybenzylamine and 8-indan-5-yl-2-methanesulfonyl-5-oxo-5,8-dihydro-pyrido[2,3-d]pyrimidine-6-carboxylic acid ethyl ester (10 mg, 0.02 mmol). 10 mg of 2-(3,5-Dimethoxy-benzylamino)-8-indan-5-yl-5-oxo-5,8-dihydro-pyrido[2,3-d]pyrimidine-6-carboxylic acid ethyl ester was obtained as a white solid. $^1$H NMR (400 MHz, CDCl$_3$) δ (ppm): 9.27 (s, 1H), 8.47 (s, 1H), 7.30 (d, J=7.8 Hz, 1H), 7.19 (s, 1H), 7.09 (d, J=7.8 Hz, 1H), 6.44 (s, 1H), 6.26 (s, 2H), 5.99 (br, 1H), 4.37 (q, J=7.1 Hz, 2H), 4.28 (d, J=6.2 Hz, 2H), 3.74 (s, 6H), 2.98 (m, 4H), 2.16 (m, 2H), 1.38 (t, J=7.1 Hz, 3H).

Step B. 2-(3,5-Dimethoxy-benzylamino)-8-indan-5-yl-5-oxo-5,8-dihydro-pyrido[2,3-d]pyrimidine-6-carboxylic acid amide Using the procedure outlined in Example 1 Step G, the title compound was prepared from 2-(3,5-dimethoxy-benzylamino)-8-indan-5-yl-5-oxo-5,8-dihydro-pyrido[2,3-d]pyrimidine-6-carboxylic acid ethyl ester (1.5 mg, 0.003 mmol). 2-(3,5-Dimethoxy-benzylamino)-8-indan-5-yl-5-oxo-5,8-dihydro-pyrido[2,3-d]pyrimidine-6-carboxylic acid amide was obtained as a white solid (0.9 mg, 60%). $^1$H NMR (400 MHz, CDCl$_3$) δ (ppm): 9.54 (br, 1H), 9.31 (s, 1H), 8.79 (s, 1H), 7.32 (d, J=7.8 Hz 1H), 7.19 (s, 1H), 7.16 (d, J=7.8 Hz, 1H), 6.35 (s, 1H), 6.28 (s, 2H), 6.04 (br, 1H), 5.72 (br, 1H), 4.31 (d, J=6.3 Hz, 2H), 3.76 (s, 6H), 2.99 (m, 4H), 2.17 (m, 2H). Mass Spectrum (LCMS, ESI pos.) Calcd. For C$_{26}$H$_{25}$N$_5$O$_4$: 472.19 (M+H). Found: 472.2.

Example 12

2-(3-Dimethylamino-propylamino)-8-indan-5-yl-5-oxo-5,8-dihydro-pyrido[2,3-d]pyrimidine-6-carboxylic acid methylamide (Cpd 12)

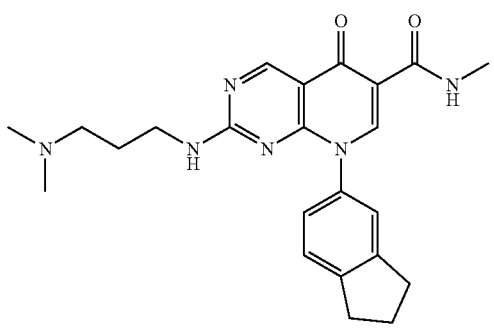

A solution of methylamine (1N, 1 mL in methanol) was added to 2-(3-dimethylamino-propylamino)-8-indan-5-yl-5-oxo-5,8-dihydro-pyrido[2,3-d]pyrimidine-6-carboxylic acid ethyl ester (Example 6 Step A, 6 mg, 0.015 mmol). The mixture was kept in a sealed tube at 110° C. with stirring for 2 days. The solution, after cooling down to room temperature, was loaded to HPLC for purification (32 mL/min 5-100% MeCN/H$_2$O gradient over 10 min). 2-(3-Dimethylamino-propylamino)-8-indan-5-yl-5-oxo-5,8-dihydro-pyrido[2,3-d]pyrimidine-6-carboxylic acid methylamide was obtained as a white solid (4.5 mg, 77%). $^1$H NMR (400 MHz, CDCl$_3$) δ (ppm): 9.70 (br, 1H), 9.26 (s, 1H), 8.75 (s, 1H), 7.31 (d, J=7.8 Hz, 1H), 7.22 (s, 1H), 7.15 (d, J=7.8 Hz, 1H), 6.86 (br, 1H), 2.99 (m, 9H), 2.25-2.10 (m, 10H), 1.62 (m, 2H). Mass Spectrum (LCMS, ESI pos.) Calcd. For C$_{23}$H$_{28}$N$_6$O$_2$: 421.23 (M+H). Found. 421.1

Example 13

8-Indan-5-yl-2-(3-morpholin-4-yl-propylamino)-5-oxo-5,8-dihydro-pyrido[2,3-d]pyrimidine-6-carboxylic acid methylamide (Cpd 13)

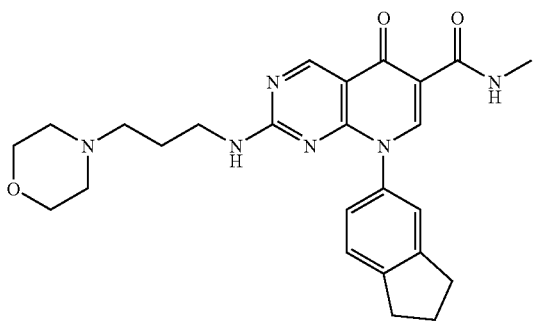

Using the procedure outlined in Example 12, the title compound was prepared from 8-indan-5-yl-2-(3-morpholin-4-yl-propylamino)-5-oxo-5,8-dihydro-pyrido[2,3-d]pyrimidine-6-carboxylic acid ethyl ester (Example 5 Step A, 2.0 mg, 0.004 mmol). 8-Indan-5-yl-2-(3-morpholin-4-yl-propylamino)-5-oxo-5,8-dihydro-pyrido[2,3-d]pyrimidine-6-carboxylic acid methylamide was obtained as a white solid (1.7 mg, 85%). $^1$H NMR (400 MHz, CDCl$_3$) δ (ppm): 9.69 (br, 1H), 9.26 (s, 1H), 8.75 (s, 1H), 7.31 (d, J=7.8 Hz, 1H), 7.22 (s, 1H), 7.16 (d, J=7.8 Hz, 1H), 6.68 (br, 1H), 3.71 (m, 4H), 3.50 (m, 4H), 2.99 (m, 9H), 2.40 (m, 4H), 2.17 (m, 2H), 1.64 (m, 2H). Mass Spectrum (LCMS, ESI pos.) Calcd. For C$_{25}$H$_{30}$N$_6$O$_3$: 463.24 (M+H). Found. 463.2.

Example 14

8-Indan-5-yl-5-oxo-2-[3-(2-oxo-pyrrolidin-1-yl)-propylamino]-5,8-dihydro-pyrido[2,3-d]pyrimidine-6-carboxylic acid methylamide (Cpd 14)

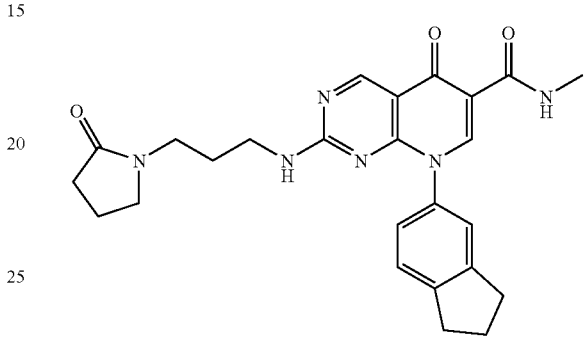

Using the procedure outlined in Example 12, the title compound was prepared from 8-indan-5-yl-5-oxo-2-[3-(2-oxo-pyrrolidin-1-yl)-propylamino]-5,8-dihydro-pyrido[2,3-d]pyrimidine-6-carboxylic acid ethyl ester (Example 8 Step A, 2.0 mg, 0.004 mmol). 8-Indan-5-yl-5-oxo-2-[3-(2-oxo-pyrrolidin-1-yl)-propylamino]-5,8-dihydro-pyrido[2,3-d]pyrimidine-6-carboxylic acid methylamide was obtained as a white solid (1.8 mg, 85%). $^1$H NMR (400 MHz, CDCl$_3$) δ (ppm): 9.70 (br, 1H), 9.27 (s, 1H), 8.76 (s, 1H), 7.31 (d, J=7.8 Hz, 1H), 7.22 (s, 1H), 7.15 (d, J=7.8 Hz, 1H), 6.37 (br, 1H), 3.23 (m, 4H), 2.99 (m, 9H), 2.38 (m, 2H), 2.17 (m, 2H), 2.01 (m, 2H), 1.55 (m, 2H). Mass Spectrum (LCMS, ESI pos.) Calcd. For C$_{25}$H$_{28}$N$_6$O$_3$: 461.22 (M+H). Found. 461.2.

Example 15

8-Indan-5-yl-2-[3-(4-methyl-piperazin-1-yl)-propylamino]-5-oxo-5,8-dihydro-pyrido[2,3-d]pyrimidine-6-carboxylic acid methylamide (Cpd 15)

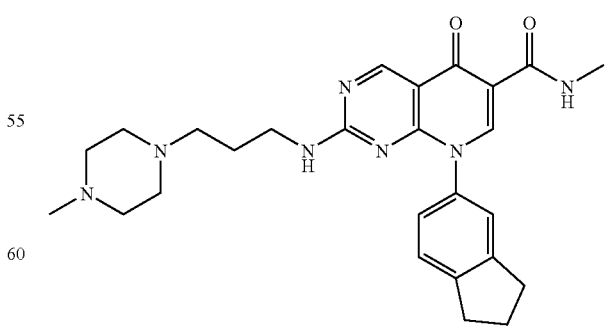

Using the procedure outlined in Example 12, the title compound was prepared from 8-Indan-5-yl-2-[3-(4-methyl-piperazin-1-yl)-propylamino]-5-oxo-5,8-dihydro-pyrido[2,3-d]

pyrimidine-6-carboxylic acid ethyl ester (Example 1 Step F, 2.0 mg, 0.004 mmol). 8-Indan-5-yl-2-[3-(4-methyl-piperazin-1-yl)-propylamino]-5-oxo-5,8-dihydro-pyrido[2,3-d]pyrimidine-6-carboxylic acid methylamide was obtained as a white solid (1.2 mg, 60%). $^1$H NMR (400 MHz, CDCl$_3$) δ (ppm): 9.70 (br, 1H), 9.27 (s, 1H), 8.76 (s, 1H), 7.31 (d, J=7.8 Hz, 1H), 7.22 (s, 1H), 7.15 (d, J=7.8 Hz, 1H), 6.80 (br, 1H), 2.99 (m, 9H), 2.48 (m, 8H), 2.36 (m, 2H), 2.32 (s, 3H), 2.19 (m, 2H), 1.55 (m, 2H). Mass Spectrum (LCMS, ESI pos.) Calcd. For C$_{26}$H$_{33}$N$_7$O$_2$: 476.27 (M+H). Found. 476.2.

Example 16

8-Indan-5-yl-2-(2-methoxy-ethylamino)-5-oxo-5,8-dihydro-pyrido[2,3-d]pyrimidine-6-carboxylic acid methylamide (Cpd 16)

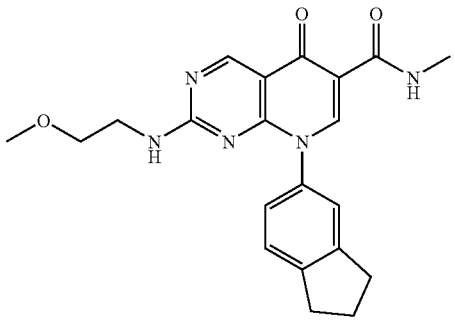

Using the procedure outlined in Example 12, the title compound was prepared from 8-indan-5-yl-2-(2-methoxy-ethylamino)-5-oxo-5,8-dihydro-pyrido[2,3-d]pyrimidine-6-carboxylic acid ethyl ester (Example 10 Step A, 3.0 mg, 0.007 mmol). 8-Indan-5-yl-2-(2-methoxy-ethylamino)-5-oxo-5,8-dihydro-pyrido[2,3-d]pyrimidine-6-carboxylic acid methylamide was obtained as a white solid (2.4 mg, 80%). $^1$H NMR (400 MHz, CDCl$_3$) δ (ppm): 9.67 (br, 1H), 9.28 (s, 1H), 8.76 (s, 1H), 7.33 (d, J=7.8 Hz, 1H), 7.21 (s, 1H), 7.15 (d, J=7.8 Hz, 1H), 5.94 (br, 1H), 3.45-3.35 (m, 4H), 3.30 (s, 3H), 2.99 (m, 7H), 2.17 (m, 2H). Mass Spectrum (LCMS, ESI pos.) Calcd. For C$_{21}$H$_{23}$N$_5$O$_3$: 394.18 (M+H). Found. 394.1.

Example 17

8-Indan-5-yl-2-[2-(4-methoxy-phenyl)-ethylamino]-5-oxo-5,8-dihydro-pyrido[2,3-d]pyrimidine-6-carboxylic acid methylamide (Cpd 17)

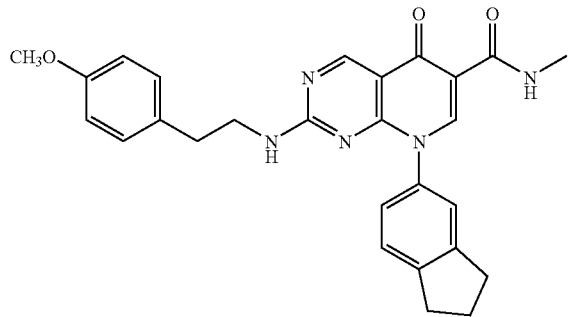

Step A. 8-Indan-5-yl-2-[2-(4-methoxy-phenyl)-ethylamino]-5-oxo-5,8-dihydro-pyrido[2,3-d]pyrimidine-6-carboxylic acid ethyl ester Using the procedure outlined in Example 1 Step F, the title compound was prepared 2-(4-methoxyphenyl)-ethylamine and 8-indan-5-yl-2-methanesulfonyl-5-oxo-5,8-dihydro-pyrido[2,3-d]pyrimidine-6-carboxylic acid ethyl ester (from Example 1 Step E, 20 mg, 0.04 mmol). 19 mg of 8-Indan-5-yl-2-[2-(4-methoxy-phenyl)-ethylamino]-5-oxo-5,8-dihydro-pyrido[2,3-d]pyrimidine-6-carboxylic acid ethyl ester was obtained as a white solid. $^1$H NMR (400 MHz, CDCl$_3$) δ (ppm): 9.23 (s, 1H), 8.47 (s, 1H), 7.37 (d, J=7.8 Hz, 1H), 7.26 (s, 1H), 7.18 (d, J=7.8 Hz, 1H), 6.81 (d, J=8.6 Hz, 2H), 6.77 (d, J=8.6 Hz, 2H), 5.84 (br, 1H), 4.37 (q, J=7.1 Hz, 2H), 3.78 (s, 3H), 3.34 (m, 2H), 3.00 (m, 7H), 2.64 (t, J=7.2 Hz, 2H), 2.18 (m, 2H), 1.38 (t, J=7.1 Hz, 3H).

Step B. 8-Indan-5-yl-2-[2-(4-methoxy-phenyl)-ethylamino]-5-oxo-5,8-dihydro-pyrido[2,3-d]pyrimidine-6-carboxylic acid methylamide Using the procedure outlined in Example 12, the title compound was prepared from 8-indan-5-yl-2-[2-(4-methoxy-phenyl)-ethylamino]-5-oxo-5,8-dihydro-pyrido[2,3-d]pyrimidine-6-carboxylic acid ethyl ester (3.0 mg, 0.007 mmol). 8-Indan-5-yl-2-[2-(4-methoxy-phenyl)-ethylamino]-5-oxo-5,8-dihydro-pyrido[2,3-d]pyrimidine-6-carboxylic acid methylamide was obtained as a white solid (2.1 mg, 70%). $^1$H NMR (400 MHz, CDCl$_3$) δ (ppm): 9.68 (br, 1H), 9.26 (s, 1H), 8.77 (s, 1H), 7.36 (d, J=7.8 Hz, 1H), 7.25 (s, 1H), 7.17 (d, J=7.8 Hz, 1H), 6.82 (d, J=8.6 Hz, 2H), 6.78 (d, J=8.6 Hz, 2H), 5.77 (br, 1H), 3.79 (s, 3H), 3.35 (m, 2H), 3.00 (m, 7H), 2.66 (t, J=7.2 Hz, 2H), 2.17 (m, 2H). Mass Spectrum (LCMS, ESI pos.) Calcd. For C$_{27}$H$_{27}$N$_5$O$_3$: 470.21 (M+H). Found. 470.2.

Example 18

8-Indan-5-yl-2-(2-morpholin-4-yl-ethylamino)-5-oxo-5,8-dihydro-pyrido[2,3-d]pyrimidine-6-carboxylic acid methylamide (Cpd 18)

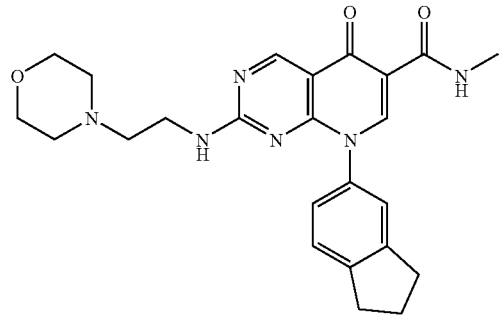

Using the procedure outlined in Example 12, the title compound was prepared from 8-indan-5-yl-2-(2-morpholin-4-yl-ethylamino)-5-oxo-5,8-dihydro-pyrido[2,3-d]pyrimidine-6-carboxylic acid ethyl ester (Example 4 Step A, 4 mg, 0.01 mmol). 8-Indan-5-yl-2-(2-morpholin-4-yl-ethylamino)-5-oxo-5,8-dihydro-pyrido[2,3-d]pyrimidine-6-carboxylic acid methylamide was obtained as a white solid (3.2 mg, 80%). $^1$H NMR (400 MHz, CDCl$_3$) δ (ppm): 9.67 (br, 1H), 9.28 (s, 1H), 8.75 (s, 1H), 7.32 (d, J=7.8 Hz, 1H), 7.21 (s, 1H), 7.15 (d, J=7.8 Hz, 1H), 6.18 (br, 1H), 3.66 (m, 4H), 2.99 (m, 7H), 2.45 (m, 2H), 2.36 (m, 2H), 2.18 (m, 2H). Mass Spectrum (LCMS, ESI pos.) Calcd. For $C_{24}H_{28}N_6O_3$: 449.22 (M+H). Found. 449.2.

Example 19

2-(3-Imidazol-1-yl-propylamino)-8-indan-5-yl-5-oxo-5,8-dihydro-pyrido[2,3-d]pyrimidine-6-carboxylic acid methoxy-amide (Cpd 19)

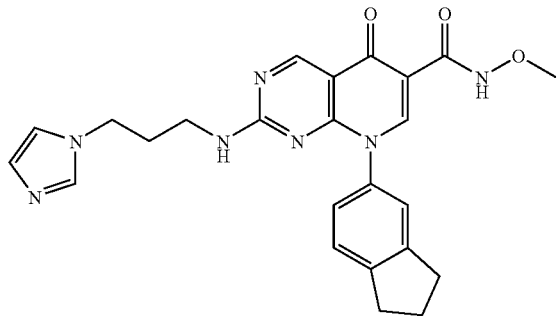

Triethylamine (0.5 mL) was added to a mixture of O-methylhydroxylamine hydrochloride (220 mg) and 2-(3-imidazol-1-yl-propylamino)-8-indan-5-yl-5-oxo-5,8-dihydro-pyrido[2,3-d]pyrimidine-6-carboxylic acid ethyl ester (Example 3 Step A, 3.0 mg, 0.006 mmol) in 0.5 mL of methanol. The reaction mixture was kept in a sealed tube at 110° C. for 2 days with stirring. After cooling to room temperature the solution was diluted with water and extracted with dichloromethane. The crude product, after concentration, was loaded to HPLC for purification (32 mL/min 5-100% MeCN/ $H_2O$ gradient over 10 min). 2-(3-Imidazol-1-yl-propylamino)-8-indan-5-yl-5-oxo-5,8-dihydro-pyrido[2,3-d]pyrimidine-6-carboxylic acid methoxy-amide was obtained as a white solid (1.9 mg, 65%). $^1$H NMR (400 MHz, $CDCl_3$) δ (ppm): 11.98 (br, 1H), 9.28 (s, 1H), 8.75 (s, 1H), 7.32 (d, J=7.8 Hz, 1H), 7.21 (s, 1H), 7.14 (d, J=7.8 Hz, 1H), 7.03 (br, 2), 6.74 (s, 1H), 5.80 (br, 1H), 3.89 (s, 3H), 3.00 (m, 8H), 2.17 (m, 2H), 1.92 (m, 2H). Mass Spectrum (LCMS, ESI pos.) Calcd. For $C_{24}H_{25}N_7O_3$: 460.20 (M+H). Found. 460.2.

Example 20

2-(3-Dimethylamino-propylamino)-8-indan-5-yl-5-oxo-5,8-dihydro-pyrido[2,3-d]pyrimidine-6-carboxylic acid methoxy-amide (Cpd 20)

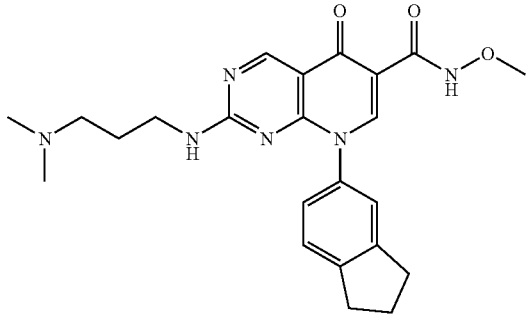

Using the procedure outlined in Example 19, the title compound was prepared from 2-(3-dimethylamino-propylamino)-8-indan-5-yl-5-oxo-5,8-dihydro-pyrido[2,3-d]pyrimidine-6-carboxylic acid ethyl ester (Example 6 Step A, 5.0 mg, 0.012 mmol). 2-(3-Dimethylamino-propylamino)-8-indan-5-yl-5-oxo-5,8-dihydro-pyrido[2,3-d]pyrimidine-6-carboxylic acid methoxy-amide was obtained as a white solid (3.9 mg, 80%). $^1$H NMR (400 MHz, $CDCl_3$) δ (ppm): 12.04 (br, 1H), 9.25 (s, 1H), 8.73 (s, 1H), 7.33 (d, J=7.8 Hz, 1H), 7.22 (s, 1H), 7.13 (d, J=7.8 Hz, 1H), 6.98 (br, 1H), 3.89 (s, 3H), 2.99 (m, 6H), 2.29 (t, J=6.7 Hz, 2H), 2.22 (m, 2H), 2.19 (s, 6H), 1.62 (m, 2H). Mass Spectrum (LCMS, ESI pos.) Calcd. For $C_{23}H_{28}N_6O_3$: 437.22 (M+H). Found. 437.2.

Example 21

8-Indan-5-yl-2-(3-methoxy-propylamino)-5-oxo-5,8-dihydro-pyrido[2,3-d]pyrimidine-6-carboxylic acid methoxy-amide (Cpd 21)

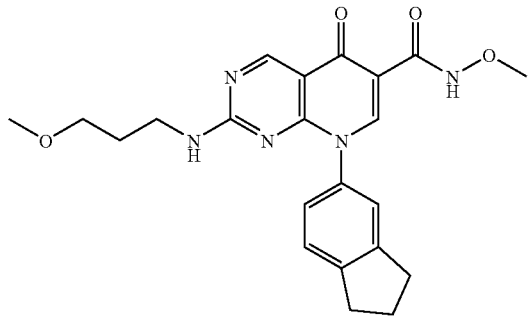

Using the procedure outlined in Example 19, the title compound was prepared from 8-indan-5-yl-2-(3-methoxy-propylamino)-5-oxo-5,8-dihydro-pyrido[2,3-d]pyrimidine-6-carboxylic acid ethyl ester (Example 7, Step A, 3.0 mg, 0.007 mmol). 8-Indan-5-yl-2-(3-methoxy-propylamino)-5-oxo-5,8-dihydro-pyrido[2,3-d]pyrimidine-6-carboxylic acid methoxyamide was obtained as a white solid (1.8 mg, 60%). $^1$H NMR (400 MHz, $CDCl_3$) δ (ppm): 12.03 (br, 1H), 9.25 (s, 1H), 8.74 (s, 1H), 7.33 (d, J=7.8 Hz, 1H), 7.22 (s, 1H), 7.12 (d, J=7.8 Hz, 1H), 6.15 (br, 1H), 3.89 (s, 3H), 3.36 (t, J=5.9 Hz, 2H), 3.29 (s, 2H), 3.26 (m, 2H), 2.99 (m, 4H), 2.18 (m, 2H), 1.72 (m, 2H). Mass Spectrum (LCMS, ESI pos.) Calcd. For $C_{22}H_{25}N_5O_4$: 424.19 (M+H). Found. 424.2.

Example 22

8-Indan-5-yl-5-oxo-2-[3-(2-oxo-pyrrolidin-1-yl)-propylamino]-5,8-dihydro-pyrido[2,3-d]pyrimidine-6-carboxylic acid methoxy-amide (Cpd 22)

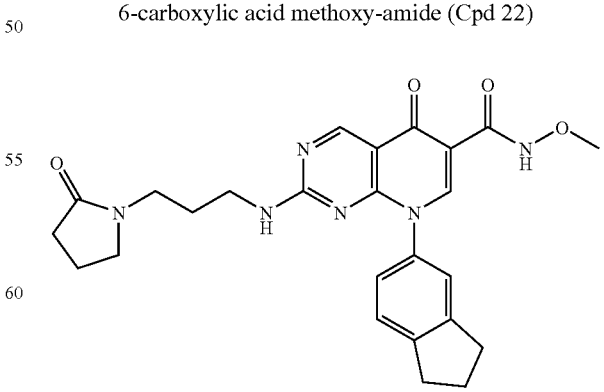

Using the procedure outlined in Example 19, the title compound was prepared from 8-indan-5-yl-5-oxo-2-[3-(2-oxo-pyrrolidin-1-yl)-propylamino]-5,8-dihydro-pyrido[2,3-d]

pyrimidine-6-carboxylic acid ethyl ester (Example 8 Step A, 5.0 mg, 0.01 mmol). 8-Indan-5-yl-5-oxo-2-[3-(2-oxo-pyrrolidin-1-yl)-propylamino]-5,8-dihydro-pyrido[2,3-d]pyrimidine-6-carboxylic acid methoxy-amide was obtained as a white solid (2.9 mg, 60%). $^1$H NMR (400 MHz, CDCl$_3$) δ (ppm): 12.04 (br, 1H), 9.26 (s, 1H), 8.73 (s, 1H), 7.32 (d, J=7.8 Hz, 1H), 7.21 (s, 1H), 7.14 (d, J=7.8 Hz, 1H), 6.50 (br, 1), 3.89 (s, 3H), 3.40-3.10 (m, 6H), 2.99 (m, 4H), 2.38 (m, 2H), 2.18 (s, 2H), 1.99 (m, 2H), 1.62 (m, 2H). Mass Spectrum (LCMS, ESI pos.) Calcd. For $C_{25}H_{28}N_6O_4$: 477.22 (M+H). Found. 477.1.

Example 23

8-Indan-5-yl-2-(2-methoxy-ethylamino)-5-oxo-5,8-dihydro-pyrido[2,3-d]pyrimidine-6-carboxylic acid methoxy-amide (Cpd 23)

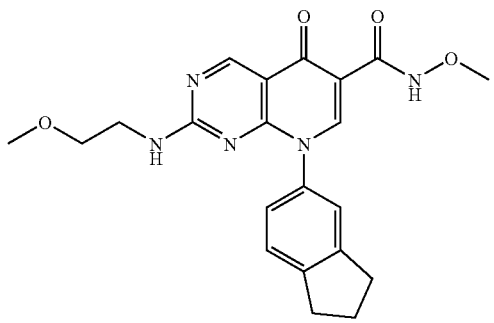

Using the procedure outlined in Example 19, the title compound was prepared from 8-indan-5-yl-2-(2-methoxy-ethylamino)-5-oxo-5,8-dihydro-pyrido[2,3-d]pyrimidine-6-carboxylic acid ethyl ester (Example 10 Step A, 5.0 mg, 0.012 mmol). 8-Indan-5-yl-2-(2-methoxy-ethylamino)-5-oxo-5,8-dihydro-pyrido[2,3-d]pyrimidine-6-carboxylic acid methoxy-amide was obtained as a white solid (4.2 mg, 85%). $^1$H NMR (400 MHz, CDCl$_3$) δ (ppm): 12.02 (br, 1H), 9.27 (s, 1H), 8.74 (s, 1H), 7.33 (d, J=7.8 Hz, 1H), 7.21 (s, 1H), 7.14 (d, J=7.8 Hz, 1H), 6.02 (br, 1H), 3.89 (s, 3H), 3.42-3.33 (m, 4H), 3.30 (s, 3H), 2.99 (m, 4H), 2.18 (m, 2H). Mass Spectrum (LCMS, ESI pos.) Calcd. For $C_{21}H_{23}N_5O_4$: 410.18 (M+H). Found. 410.1.

Example 24

8-Indan-5-yl-2-[2-(4-methoxy-phenyl)-ethylamino]-5-oxo-5,8-dihydro-pyrido[2,3-d]pyrimidine-6-carboxylic acid methoxy-amide (Cpd 24)

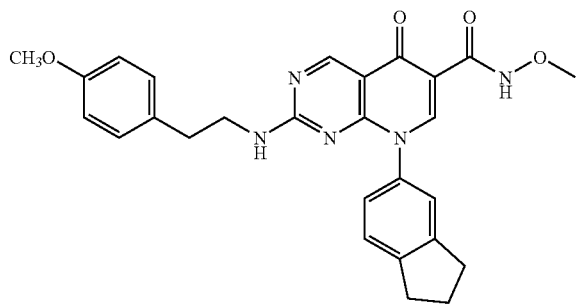

Step A. 8-Indan-5-yl-2-[2-(4-methoxy-phenyl)-ethylamino]-5-oxo-5,8-dihydro-pyrido[2,3-d]pyrimidine-6-carboxylic acid ethyl ester Using the procedure outlined in Example 1 Step F, the title compound was prepared from 2-(4-methoxy-phenyl)-ethylamine and 8-indan-5-yl-2-methanesulfonyl-5-oxo-5,8-dihydro-pyrido[2,3-d]pyrimidine-6-carboxylic acid ethyl ester (Example 1 Step E, 20 mg, 0.040 mmol). 16 mg of 8-Indan-5-yl-2-(2-(4-methoxy-phenyl)-ethylamino)-5-oxo-5,8-dihydro-pyrido[2,3-d]pyrimidine-6-carboxylic acid ethyl ester was obtained as a white solid.

Step B. 8-indan-5-yl-2-[2-(4-methoxy-phenyl)-ethylamino]-5-oxo-5,8-dihydro-pyrido[2,3-d]pyrimidine-6-carboxylic acid methoxy-amide Using the procedure outlined in Example 19, 8-indan-5-yl-2-[2-(4-methoxy-phenyl)-ethylamino]-5-oxo-5,8-dihydro-pyrido[2,3-d]pyrimidine-6-carboxylic acid methoxy-amide was obtained as a white solid (4.2 mg, 85%) from 8-indan-5-yl-2-[2-(4-methoxy-phenyl)-ethylamino]-5-oxo-5,8-dihydro-pyrido[2,3-d]pyrimidine-6-carboxylic acid ethyl ester (5.0 mg, 0.01 mmol). $^1$H NMR (400 MHz, CDCl$_3$) δ (ppm): 12.02 (br, 1H), 9.25 (s, 1H), 8.75 (s, 1H), 7.36 (d, J=7.8 Hz, 1H), 7.24 (s, 1H), 7.16 (d, J=7.8 Hz, 1H), 6.83 (d, J=Hz, 2H), 6.74 (d, J=Hz, 2H), 5.87 (br, 1H), 3.89 (s, 3H), 3.78 (s, 3H), 3.34 (m, 2H), 3.03 (m, 2H), 2.96 (m, 2H), 2.65 (m, 2H), 2.18 (m, 2H). Mass Spectrum (LCMS, ESI pos.) Calcd. For $C_{27}H_{27}N_5O_4$: 486.21 (M+H). Found. 486.1.

Example 25

8-Indan-5-yl-5-oxo-2-(2-piperidin-1-yl-ethylamino)-5,8-dihydro-pyrido[2,3-d]pyrimidine-6-carboxylic acid methoxy-amide (Cpd 25)

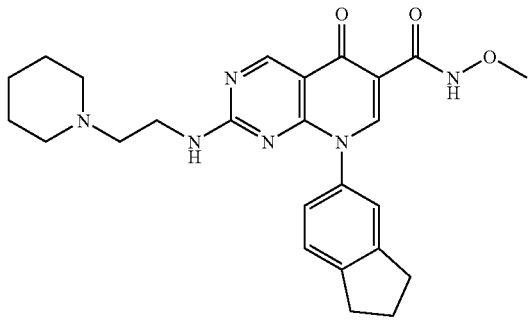

Using the procedure outlined in Example 19, the title compound was prepared from 8-indan-5-yl-5-oxo-2-(2-piperidin-1-yl-ethylamino)-5,8-dihydro-pyrido[2,3-d]pyrimidine-6-carboxylic acid ethyl ester (Example 2 Step A, 4.0 mg, 0.008 mmol). 8-Indan-5-yl-5-oxo-2-(2-piperidin-1-yl-ethylamino)-5,8-dihydro-pyrido[2,3-d]pyrimidine-6-carboxylic acid methoxy-amide was obtained as a white solid (2.9 mg, 75%). $^1$H NMR (400 MHz, CDCl$_3$) δ (ppm): 12.03 (br, 1H), 9.26 (s, 1H), 8.74 (s, 1H), 7.32 (d, J=7.8 Hz, 1H), 7.21 (s, 1H), 7.13 (d, J=7.8 Hz, 1H), 6.38 (br, 1H), 3.89 (s, 3H), 3.24 (m, 2H), 2.99 (m, 4H), 2.40-1.53 (m, 14H). Mass Spectrum (LCMS, ESI pos.) Calcd. For $C_{25}H_{30}N_6O_3$: 463.24 (M+H), Found. 463.2.

Example 26

8-Indan-5-yl-2-(2-morpholin-4-yl-ethylamino)-5-oxo-5,8-dihydro-pyrido[2,3-d]pyrimidine-6-carboxylic acid methoxy-amide (Cpd 26)

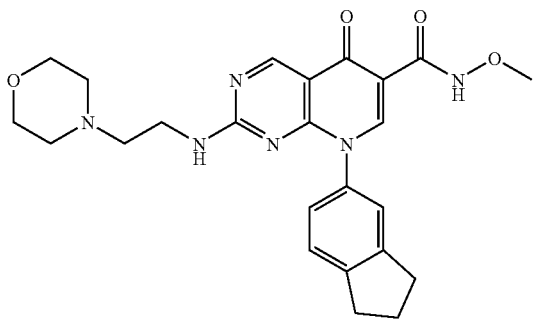

Using the procedure outlined in Example 19, the title compound was prepared from 8-indan-5-yl-2-(2-morpholin-4-yl-ethylamino)-5-oxo-5,8-dihydro-pyrido[2,3-d]pyrimidine-6-carboxylic acid ethyl ester (Example 4 Step A, 4.0 mg, 0.009 mmol). 8-Indan-5-yl-2-(2-morpholin-4-yl-ethylamino)-5-oxo-5,8-dihydro-pyrido[2,3-d]pyrimidine-6-carboxylic acid methoxy-amide was obtained as a white solid (2.7 mg, 70%). $^1$H NMR (400 MHz, CDCl$_3$) δ (ppm): 12.01 (br, 1H), 9.27 (s, 1H), 8.73 (s, 1H), 7.33 (d, J=7.8 Hz, 1H), 7.21 (s, 1H), 7.15 (d, J=7.8 Hz, 1H), 6.24 (br, 1H), 3.89 (s, 3H), 3.56 (m, 8H), 2.99 (m, 6H), 2.50-2.20 (m, 4H). Mass Spectrum (LCMS, ESI pos.) Calcd. For $C_{24}H_{28}N_6O_4$: 465.22 (M+H). Found. 465.2.

Example 27

2-(3,5-Dimethoxy-benzylamino)-8-indan-5-yl-5-oxo-5,8-dihydro-pyrido[2,3-d]pyrimidine-6-carboxylic acid methoxy-amide (Cpd 27)

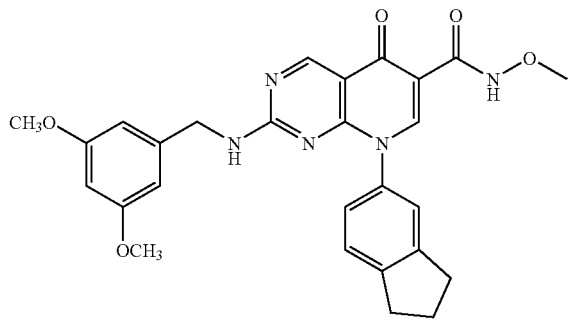

Using the procedure outlined in Example 19, the title compound was prepared from 2-(3,5-dimethoxy-benzylamino)-8-indan-5-yl-5-oxo-5,8-dihydro-pyrido[2,3-d]pyrimidine-6-carboxylic acid ethyl ester (Example 11 Step A, 3.0 mg, 0.006 mmol). 2-(3,5-Dimethoxy-benzylamino)-8-indan-5-yl-5-oxo-5,8-dihydro-pyrido[2,3-d]pyrimidine-6-carboxylic acid methoxy-amide was obtained as a white solid (1.9 mg, 60%). $^1$H NMR (400 MHz, CDCl$_3$) δ (ppm): 12.00 (br, 1H), 9.28 (s, 1H), 8.74 (s, 1H), 7.26 (d, J=7.8 Hz, 1H), 7.14 (s, 1H), 7.07 (d, J=7.8 Hz, 1H), 6.44 (s, 1H), 6.34 (br, 1H), 6.26 (s, 2H), 4.29 (d, J=6.3 Hz, 1H), 3.89 (s, 3H), 3.74 (s, 6H), 2.98 (m, 4H), 2.16 (m, 2H). Mass Spectrum (LCMS, ESI pos.) Calcd. For $C_{27}H_{27}N_5O_5$: 502.20 (M+H). Found. 502.1.

Example 28

8-Cyclohexyl-2-(3-imidazol-1-yl-propylamino)-5-oxo-5,8-dihydro-pyrido[2,3-d]pyrimidine-6-carboxylic acid amide (Cpd 28)

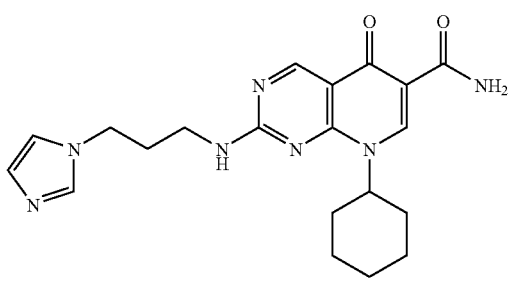

Step A. 3-Cyclohexylamino-propionic acid ethyl ester

Cyclohexylamine (0.86 g, 8.7 mmol) and 3-chloro-propionic acid ethyl ester (1.18 g, 8.67 mmol) were combined neat and K$_2$CO$_3$ (1.2 g, 8.7 mmol) and a catalytic amount of tetrabutylammonium iodide (ca. 5 mg) was added. The mixture was heated at 80° C. overnight. The resulting mixture was then partitioned between water and dichloromethane. The organic layer was dried (MgSO$_4$) and concentrated to afford 1.25 g (72%) of the title compound.

Step B. 4-[Cyclohexyl-(2-ethoxycarbonyl-ethyl)-amino]-2-methylsulfanyl-pyrimidine-5-carboxylic acid ethyl ester 3-Cyclohexylamino-propionic acid ethyl ester (1.0 g, 5.0 mmol) and 4-chloro-2-combined in dichloromethane (15 mL), and diisopropylethylamine (0.81 g, 6.3 mmol) was added. After 16 h, the solution was partitioned between water and dichloromethane, and the organic layer was dried (MgSO$_4$) and concentrated. Chromatography (0-20% EtOAc/the organic layer was dried (MgSO$_4$) and concentrated. Chromatography (0-20% EtOAc/hexanes gradient) provided 1.63 g (84%) of the title compound. $^1$H-NMR (400 MHz, CDCl$_3$) δ (ppm): 8.39 (s, 1H), 5.30 (s, 1H), 4.30 (q, J=7.1 Hz, 2H), 4.14 (q, J=7.1 Hz, 1H), 3.76-3.80 (m, 2H), 2.65-2.69 (m, 2H), 2.49 (s, 3H), 1.81-1.84 (m, 2H), 1.34-1.40 (m, 7H), 1.12-1.27 (m, 7H).

Step C. 8-Cyclohexyl-2-methylsulfanyl-5-oxo-5,6,7,8-tetrahydro-pyrido[2,3-d]pyrimidine-6-carboxylic acid ethyl ester Sodium (25 wt % dispersion in paraffin wax, 0.10 g, 3.8 mmol) was added to t-butanol (1.8 mL) at rt. After 10 minutes, a solution of 4-[cyclohexyl-(2-ethoxycarbonyl-ethyl)-amino]-2-methylsulfanyl-pyrimidine-5-carboxylic acid ethyl ester (1.0 g, 2.5 mmol) in 10 mL of toluene was added to the sodium t-butoxide solution and the resulting mixture was heated at 90° C. for 30 minutes. The reaction mixture was then cooled and the solution was adjusted to pH 7 using a 1N HCl solution. The solution was then extracted with EtOAc (2×20 mL) and the organic layer was dried (MgSO₄) and concentrated to provide 0.55 g (42%) of the title compound.

Step D. 8-Cyclohexyl-2-methylsulfanyl-5-oxo-5,8-dihydro-pyrido[2,3-d]pyrimidine-6-carboxylic acid ethyl ester Bromine (0.15 g, 0.94 mmol) was added to a solution of 8-cyclohexyl-2-methylsulfanyl-5-oxo-5,6,7,8-tetrahydro-pyrido[2,3-d]pyrimidine-6-carboxylic acid ethyl ester (0.28 g, 0.79 mmol) in dichloromethane (10 mL). After 5 min, the solution was concentrated and the crude residue was redissolved in dichloromethane (10 mL) and diisopropylethylamine (0.42 mL, 2.4 mmol) was added. After 15 h, the reaction mixture was partitioned between water and dichloromethane, the organic layer was separated, dried (MgSO₄) and concentrated to provide 0.28 g (87%) of the title compound. Mass Spectrum (LCMS, ESI pos.) Calcd. For $C_{17}H_{21}N_3O_3S$: 347.13. found: (M+H) 348.3.

Step E. 8-Cyclohexyl-2-methanesulfonyl-5-oxo-5,8-dihydro-pyrido[2,3-d]pyrimidine-6-carboxylic acid ethyl ester m-CPBA (0.33 g, 1.5 mmol of a 70% w/w mixture) was added to a solution of 8-cyclohexyl-2-methylsulfanyl-5-oxo-5,8-dihydro-pyrido[2,3-d]pyrimidine-6-carboxylic acid ethyl ester (0.206 g, 0.59 mmol) in dichloromethane (15 mL). After 2 hours, a 10% solution of Na₂SO₃ (1 mL) was added and the mixture was partitioned between sat. NaHCO₃ and dichloromethane. The organic layer was dried (MgSO₄) and concentrated to provide 0.22 g of the title compound. Mass Spectrum (LCMS, ESI pos.) Calcd. For $C_{17}H_{21}N_3O_5S$: 379.12. found: (M+H) 380.1.

Step F. 8-Cyclohexyl-2-(3-imidazol-1-yl-propylamino)-5-oxo-5,8-dihydro-pyrido[2,3-d]pyrimidine-6-carboxylic acid ethyl ester A solution of 3-imidazol-1-yl-propylamine (6 μL, 0.036 mmol) and 8-cyclohexyl-2-methanesulfonyl-5-oxo-5,8-dihydro-pyrido[2,3-d]pyrimidine-6-carboxylic acid ethyl ester (30 mg, 0.08 mmol) in 0.5 mL of acetic acid was heated to 110° C. for 0.5 hour. After cooling to room temperature, the mixture was dissolved in 2 mL of methanol and loaded to HPLC for purification (32 mL/min 5-100% MeCN/H₂O gradient over 10 min). 26 mg of 8-Cyclohexyl-2-(3-imidazol-1-yl-propylamino)-5-oxo-5,8-dihydro-pyrido[2,3-d]pyrimidine-6-carboxylic acid ethyl ester was obtained as a white solid. $^1$H NMR (300 MHz, CDCl₃) δ (ppm): 9.23 (s, 1H), 8.49 (s, 1H), 7.57 (br, 1H), 7.09 (br, 1H), 6.96 (br, 1H), 6.10 (br, 1H), 5.02 (m, 1H), 4.38 (q, J=7.2 Hz, 2H), 4.11 (t, J=6.6 Hz, 2H), 3.51 (br, 2H), 2.20-1.50 (m, 8H), 1.40 (t, J=7.2 Hz, 3H), 1.26 (m, 4H). Mass Spectrum (LCMS, ESI pos.) Calcd. For $C_{22}H_{28}N_6O_3$: 425.22 (M+H). Found: 425.2.

Step G. 8-Cyclohexyl-2-(3-imidazol-1-yl-propylamino)-5-oxo-5,8-dihydro-pyrido[2,3-d]pyrimidine-6-carboxylic acid amide 8-Cyclohexyl-2-(3-imidazol-1-yl-propylamino)-5-oxo-5,8-dihydro-pyrido[2,3-d]pyrimidine-6-carboxylic acid ethyl ester (4.5 mg, 0.011 mmol) was added to 1.0 mL of 7 N ammonia in methanol. The mixture was stirred in a sealed tube at room temperature overnight. The solvent was evaporated to leave a white solid of 8-cyclohexyl-2-(3-imidazol-1-yl-propylamino)-5-oxo-5,8-dihydro-pyrido[2,3-d]pyrimidine-6-carboxylic acid amide (4.0 mg, 95%). $^1$H NMR (400 MHz, CDCl₃/CD₃OD (20:1 v/v)) δ (ppm): 9.18 (s), 8.74 (s), 7.15 (br, 1H), 7.02 (br, 1H), 6.92 (br, 1H), 5.02 (m, 1H), 4.06 (t, J=6.6 Hz, 2H), 3.43 (br, 2H), 2.17 (m, 2H), 2.00-1.30 (br, 10H). Mass Spectrum (LCMS, ESI pos.) Calcd. For $C_{20}H_{25}N_7O_2$: 396.21 (M+H). Found: 396.2.

Example 29

8-Cyclohexyl-2-(3-dimethylamino-propylamino)-5-oxo-5,8-dihydro-pyrido[2,3-d]pyrimidine-6-carboxylic acid amide (Cpd 29)

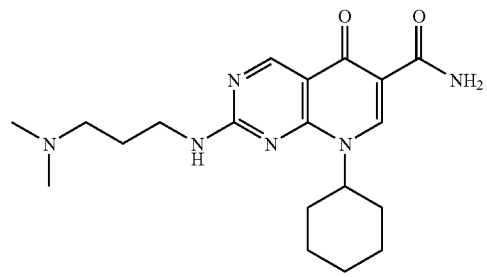

Step A. 8-Cyclohexyl-2-(3-dimethylamino-propylamino)-5-oxo-5,8-dihydro-pyrido[2,3-d]pyrimidine-6-carboxylic acid ethyl ester Using the procedure outlined in Example 28 Step F, the title compound was prepared from N',N'-dimethyl-propane-1,3-diamine and 8-cyclohexyl-2-methanesulfonyl-5-oxo-5,8-dihydro-pyrido[2,3-d]pyrimidine-6-carboxylic acid ethyl ester (Example 35 Step E, 20 mg, 0.05 mmol). 8-Cyclohexyl-2-(3-dimethylamino-propylamino)-5-oxo-5,8-dihydro-pyrido[2,3-d]pyrimidine-6-carboxylic acid ethyl ester was obtained as a white solid (17 mg, 85%). Mass Spectrum (LCMS, ESI pos.) Calcd. For $C_{21}H_{31}N_5O_3$: 402.24 (M+H). Found: 402.2.

Step B. 8-Cyclohexyl-2-(3-dimethylamino-propylamino)-5-oxo-5,8-dihydro-pyrido[2,3-d]pyrimidine-6-carboxylic acid amide Using the procedure outlined in Example 28 Step G, 8-cyclohexyl-2-(3-dimethylamino-propylamino)-5-oxo-5,8-dihydro-pyrido[2,3-d]pyrimidine-6-carboxylic acid amide was obtained as a white solid (4.4 mg, 85%) from 8-cyclohexyl-2-(3-dimethylamino-propylamino)-5-oxo-5,8-dihydro-pyrido[2,3-d]pyrimidine-6-carboxylic acid ethyl ester (5.0 mg, 0.012 mmol). $^1$H NMR (400 MHz, CDCl₃) δ (ppm): 9.58 (br, 1H), 9.25 (s, 1H), 8.78 (s, 1H), 7.09 (br, 1H), 5.71 (br, 1H), 5.16 (m, 1H), 3.58 (m, 2H), 2.50 (m, 2H), 2.37 (m, 2H), 2.30 (s, 6H), 2.05-1.40 (br, 10H). Mass Spectrum (LCMS, ESI pos.) Calcd. For $C_{19}H_{28}N_6O_2$: 373.23 (M+H). Found: 373.2.

Example 30

8-Cyclohexyl-2-(3-morpholin-4-yl-propylamino)-5-oxo-5,8-dihydro-pyrido[2,3-d]pyrimidine-6-carboxylic acid amide (Cpd 30)

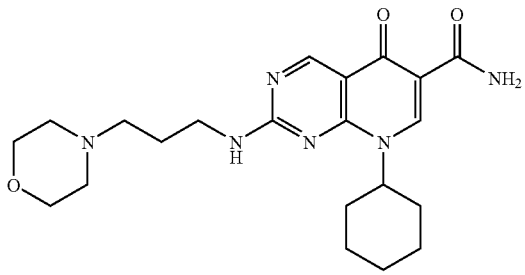

Step A. 8-Cyclohexyl-2-(3-morpholin-4-yl-propylamino)-5-oxo-5,8-dihydro-pyrido[2,3-d]pyrimidine-6-carboxylic acid ethyl ester Using the procedure outlined in Example 28 Step F, the title compound was prepared from 3-morpholin-4-yl-propylamine and 8-cyclohexyl-2-methanesulfonyl-5-oxo-5,8-dihydro-pyrido[2,3-d]pyrimidine-6-carboxylic acid ethyl ester (from Example 35 Step E, 20 mg, 0.045 mmol). 8-Cyclohexyl-2-(3-morpholin-4-yl-propylamino)-5-oxo-5,8-dihydro-pyrido[2,3-d]pyrimidine-6-carboxylic acid ethyl ester was obtained as a white solid (18 mg, 85%). Mass Spectrum (LCMS, ESI pos.) Calcd. For $C_{23}H_{33}N_5O_4$: 444.25 (M+H). Found: 4444.3.

Step B. 8-Cyclohexyl-2-(3-morpholin-4-yl-propylamino)-5-oxo-5,8-dihydro-pyrido[2,3-d]pyrimidine-6-carboxylic acid amide Using the procedure outlined in Example 28 Step G, 8-cyclohexyl-2-(3-morpholin-4-yl-propylamino)-5-oxo-5,8-dihydro-pyrido[2,3-d]pyrimidine-6-carboxylic acid amide was obtained as a white solid (3.0 mg, 80%) from 8-cyclohexyl-2-(3-morpholin-4-yl-propylamino)-5-oxo-5,8-dihydro-pyrido[2,3-d]pyrimidine-6-carboxylic acid ethyl ester (4 mg, 0.01 mmol). $^1$H NMR (400 MHz, CDCl$_3$) δ (ppm): 9.59 (br, 1H), 9.24 (s, 1H), 8.78 (s, 1H), 6.91 (br, 1H), 5.75 (br, 1H), 5.15 (m, 1H), 3.77 (m, 4H), 3.58 (m, 2H), 2.49 (m, 6H), 2.10-1.20 (br, 12H). Mass Spectrum (LCMS, ESI pos.) Calcd. For $C_{21}H_{30}N_6O_3$: 415.24 (M+H). Found: 415.2.

Example 31

8-Cyclohexyl-2-(3-methoxy-propylamino)-5-oxo-5,8-dihydro-pyrido[2,3-d]pyrimidine-6-carboxylic acid amide (Cpd 31)

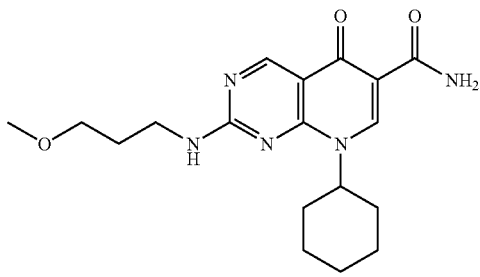

Step A. 8-Cyclohexyl-2-(3-methoxy-propylamino)-5-oxo-5,8-dihydro-pyrido[2,3-d]pyrimidine-6-carboxylic acid ethyl ester Using the procedure outlined in Example 28 Step F, the title compound was prepared from 3-methoxy-propylamine and 8-cyclohexyl-2-methanesulfonyl-5-oxo-5,8-dihydro-pyrido[2,3-d]pyrimidine-6-carboxylic acid ethyl ester (from Example 35 (Step E) above, 30 mg, 0.08 mmol). 8-Cyclohexyl-2-(3-methoxy-propylamino)-5-oxo-5,8-dihydro-pyrido[2,3-d]pyrimidine-6-carboxylic acid ethyl ester was obtained as a white solid (24 mg, 80%). $^1$H NMR (400 MHz, CDCl$_3$) δ (ppm): 9.29 (br, 1H), 8.48 (s, 1H), 6.21 (br, 1H), 5.11 (m, 1H), 4.38 (q, J=7.1 Hz, 2H), 3.70-3.46 (m, 4H), 3.37 (s, 3H), 2.06-1.24 (m, 15H). Mass Spectrum (LCMS, ESI pos.) Calcd. For $C_{20}H_{28}N_4O_4$: 389.21 (M+H). Found: 389.2.

Step B. 8-Cyclohexyl-2-(3-methoxy-propylamino)-5-oxo-5,8-dihydro-pyrido[2,3-d]pyrimidine-6-carboxylic acid amide Using the procedure outlined in Example 35 (Tep G), 8-cyclohexyl-2-(3-methoxy-propylamino)-5-oxo-5,8-dihydro-pyrido[2,3-d]pyrimidine-6-carboxylic acid amide was obtained as a white solid (5.8 mg, 100%) from 8-cyclohexyl-2-(3-methoxy-propylamino)-5-oxo-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.58 (br, 1H), 9.25 (s, 1H), 8.79 (s, 1H), 6.25 (br, 1H), 5.71 (br, 1H), 5.17 (m, 1H), 3.70-3.46 (m, 4H), 3.38 (s, 3H), (s, 3H), 2.06-1.24 (br, 12H). Mass Spectrum (LCMS, ESI pos.) Calcd. For $C_{18}H_{28}N_5O_3$: 360.20 (M+H). Found: 360.2.

Example 32

8-Cyclohexyl-5-oxo-2-[3-(2-oxo-pyrrolidin-1-yl)-propylamino]-5,8-dihydro-pyrido[2,3-d]pyrimidine-6-carboxylic acid amide (Cpd 32)

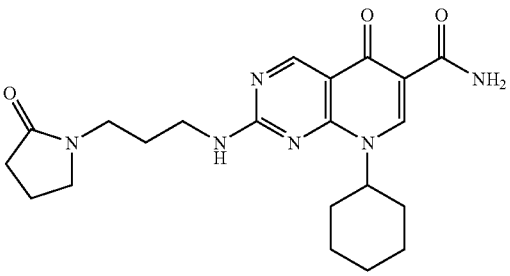

Step A. 8-Cyclohexyl-2-(2-oxo-pyrrolidin-1-yl)-propylamino)-5-oxo-5,8-dihydro-pyrido[2,3-d]pyrimidine-6-carboxylic acid ethyl ester Using the procedure outlined in Example 28 Step F, the title compound was prepared from 1-(3-amino-propyl)-pyrrolidin-2-one and 8-cyclohexyl-2-methanesulfonyl-5-oxo-5,8-dihydro-pyrido[2,3-d]pyrimidine-6-carboxylic acid ethyl ester (10 mg, 0.02 mmol). 8-Cyclohexyl-2-(2-oxo-pyrrolidin-1-yl)-propylamino)-5-oxo-5,8-dihydro-pyrido[2,3-d]pyrimidine-6-carboxylic acid ethyl ester was obtained as a white solid (3.0 mg, 30%). Mass Spectrum (LCMS, ESI pos.) Calcd. For $C_{23}H_{31}N_5O_4$: 442.24 (M+H). Found: 442.2.

Step B. 8-Cyclohexyl-5-oxo-2-[3-(2-oxo-pyrrolidin-1-yl)-propylamino]-5,8-dihydro-pyrido[2,3-d]pyrimidine-6-carboxylic acid amide Using the procedure outlined in Example 28 Step G, 8-cyclohexyl-5-oxo-2-[3-(2-oxo-pyrrolidin-1-yl)-propylamino]-5,8-dihydro-pyrido[2,3-d]pyrimidine-6-carboxylic acid amide was obtained as a white solid (3.0 mg, 100%) from 8-cyclohexyl-2-(2-oxo-pyrrolidin-1-yl)-propylamino)-5-oxo-5,8-dihydro-pyrido[2,3-d]pyrimidine-6-carboxylic acid ethyl ester (3.0 mg, 0.008 mmol). $^1$H NMR (400 MHz, CDCl$_3$) δ (ppm): 9.57 (br, 1H), 9.31 (s, 1H), 8.78 (s, 1H), 6.60 (br, 1H), 5.72 (br, 1H), 5.15 (m, 1H), 3.55-3.40 (m, 6H), 2.43 (m, 2H), 2.16-1.20 (br, 16H). Mass Spectrum (LCMS, ESI pos.) Calcd. For C$_{21}$H$_{25}$N$_6$O$_3$: 413.22 (M+H). Found: 413.2.

Example 33

8-Cyclohexyl-2-[3-(4-methyl-piperazin-1-yl)-propylamino]-5-oxo-5,8-dihydro-pyrido[2,3-d]pyrimidine-6-carboxylic acid amide (Cpd 33)

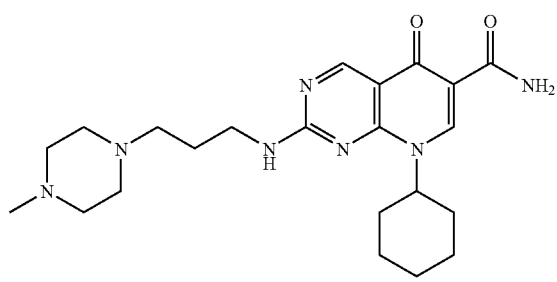

Step A. 8-Cyclohexyl-2-[3-(4-methyl-piperazin-1-yl)-propylamino]-5-oxo-5,8-dihydro-pyrido[2,3-d]pyrimidine-6-carboxylic acid ethyl ester Using the procedure outlined in Example 28 Step F, the title compound was prepared from 3-(4-methyl-piperazin-1-yl)-propylamine and 8-cyclohexyl-2-methanesulfonyl-5-oxo-5,8-dihydro-pyrido[2,3-d]pyrimidine-6-carboxylic acid ethyl ester (20 mg, 0.04 mmol). 8-Cyclohexyl-2-[3-(4-methyl-piperazin-1-yl)-propylamino]-5-oxo-5,8-dihydro-pyrido[2,3-d]pyrimidine-6-carboxylic acid ethyl ester was obtained as a white solid (17 mg, 80%). Mass Spectrum (LCMS, ESI pos.) Calcd. For C$_{24}$H$_{36}$N$_6$O$_3$: 457.28 (M+H). Found: 457.3.

Step B. 8-Cyclohexyl-2-[3-(4-methyl-piperazin-1-yl)-propylamino]-5-oxo-5,8-dihydro-pyrido[2,3-d]pyrimidine-6-carboxylic acid amide Using the procedure outlined in Example 28 Step G, 8-cyclohexyl-5-oxo-2-[3-(4-methyl-piperazin-1-yl)-propylamino]-5,8-dihydro-pyrido[2,3-d]pyrimidine-6-carboxylic acid amide was obtained as a white solid (5.2 mg, 85%) from 8-cyclohexyl-2-[3-(4-methyl-piperazin-1-yl)-propylamino]-5-oxo-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.58 (br, 1H), 9.24 (s, 1H), 8.77 (s, 1H), 6.98 (br, 1H), 5.72 (br, 1H), 5.15 (m, 2H), 3.55 (m, 2H), 2.70-2.40 (m, 10H), 2.33 (s, 3H), 2.05-1.20 (br, 12H). Mass Spectrum (LCMS, ESI pos.) Calcd. For C$_{22}$H$_{33}$N$_7$O$_2$: 428.27 (M+H). Found: 428.30.

Example 34

8-Cyclohexyl-5-oxo-2-(3-pyrrolidin-1-yl-propylamino)-5,8-dihydro-pyrido[2,3-d]pyrimidine-6-carboxylic acid amide (Cpd 34)

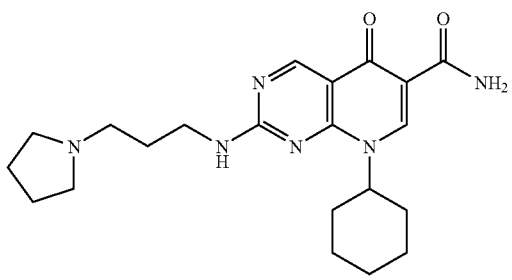

Step A. 8-Cyclohexyl-5-oxo-2-(3-pyrrolidin-1-yl-propylamino)-5,8-dihydro-pyrido[2,3-d]pyrimidine-6-carboxylic acid ethyl ester Using the procedure outlined in Example 28 Step F, the title compound was prepared from 3-pyrrolidin-1-yl-propylamine and 8-cyclohexyl-2-methanesulfonyl-5-oxo-5,8-dihydro-pyrido[2,3-d]pyrimidine-6-carboxylic acid ethyl ester (20 mg, 0.05 mmol). 8-Cyclohexyl-5-oxo-2-(3-pyrrolidin-1-yl-propylamino)-5,8-dihydro-pyrido[2,3-d]pyrimidine-6-carboxylic acid ethyl ester was obtained as a white solid (18 mg, 85%). Mass Spectrum (LCMS, ESI pos.) Calcd. For C$_{23}$H$_{33}$N$_5$O$_3$: 428.26 (M+H). Found: 428.3.

Step B. 8-Cyclohexyl-5-oxo-2-(3-pyrrolidin-1-yl-propylamino)-5,8-dihydro-pyrido[2,3-d]pyrimidine-6-carboxylic acid amide Using the procedure outlined in Example 28 Step F, 8-cyclohexyl-5-oxo-2-(3-pyrrolidin-1-yl-propylamino)-5,8-dihydro-pyrido[2,3-d]pyrimidine-6-carboxylic acid amide was obtained as a white solid (5.5 mg, 88%) from 8-cyclohexyl-5-oxo-2-(3-pyrrolidin-1-yl-propylamino)-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.57 (br, 1H), 9.24 (s, 1H), 8.77 (s, 1H), 6.94 (br, 1H), 5.72 (br, 1H), 5.15 (m, 1H), 3.61 (m, 2H), 3.00-2.70 (m, 6H), 2.05-1.20 (br, 16H). Mass Spectrum (LCMS, ESI pos.) Calcd. For C$_{21}$H$_{30}$N$_6$O$_2$: 399.24 (M+H). Found: 399.20.

Example 35

8-Cyclohexyl-2-(2-methoxy-ethylamino)-5-oxo-5,8-dihydro-pyrido[2,3-d]pyrimidine-6-carboxylic acid amide (Cpd 35)

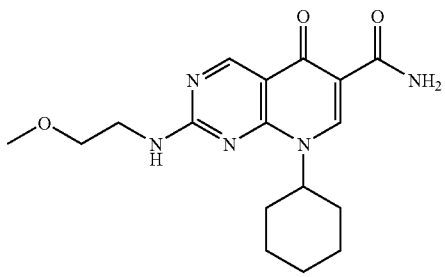

Step A. 8-Cyclohexyl-5-oxo-2-(2-methoxy-ethylamino)-5,8-dihydro-pyrido[2,3-d]pyrimidine-6-carboxylic acid ethyl ester Using the procedure outlined in Example 28 Step F, the title compound was prepared from 2-methoxy-ethylamine and 8-cyclohexyl-2-methanesulfonyl-5-oxo-5,8-dihydro-pyrido[2,3-d]pyrimidine-6-carboxylic acid ethyl ester (27 mg, 0.07 mmol). 8-Cyclohexyl-5-oxo-2-(2-methoxy-ethylamino)-5,8-dihydro-pyrido[2,3-d]pyrimidine-6-carboxylic acid ethyl ester was obtained as a white solid (20 mg, 80%). Mass Spectrum (LCMS, ESI pos.) Calcd. For $C_{19}H_{26}N_4O_4$: 375.2 (M+H). Found: 375.2.

Step B. 8-Cyclohexyl-2-(2-methoxy-ethylamino)-5-oxo-5,8-dihydro-pyrido[2,3-d]pyrimidine-6-carboxylic acid amide Using the procedure outlined in Example 28 Step G, 8-cyclohexyl-5-oxo-2-(2-methoxy-ethylamino)-5,8-dihydro-pyrido[2,3-d]pyrimidine-6-carboxylic acid amide was obtained as a white solid (6.0 mg, 100%) from 8-Cyclohexyl-5-oxo-2-(2-methoxy-ethylamino)-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.54 (br, 1H), 9.27 (s, 1H), 8.79 (s, 1H), 6.14 (br, 1H), 5.71 (br, 1H), 5.15 (m, 1H), 3.64 (m, 4H), 3.41 (s, 3H), 2.05-1.20 (m, 10H). Mass Spectrum (LCMS, ESI pos.) Calcd. For $C_{17}H_{23}N_5O_3$: 346.18 (M+H). Found: 346.2.

Example 36

8-Cyclohexyl-5-oxo-2-(2-pyrrolidin-1-yl-ethylamino)-5,8-dihydro-pyrido[2,3-d]pyrimidine-6-carboxylic acid amide (Cpd 36)

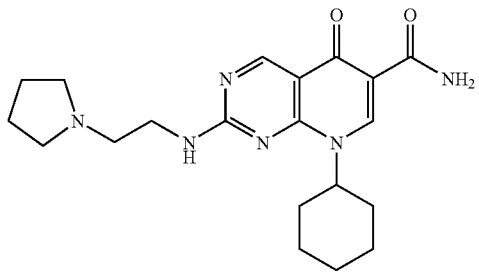

Step A. 8-Cyclohexyl-5-oxo-2-(2-pyrrolidin-1-yl-ethylamino)-5,8-dihydro-pyrido[2,3-d]pyrimidine-6-carboxylic acid ethyl ester Using the procedure outlined in Example 28 Step F, the title compound was prepared from 2-pyrrolidin-1-yl-ethylamine and 8-cyclohexyl-2-methanesulfonyl-5-oxo-5,8-dihydro-pyrido[2,3-d]pyrimidine-6-carboxylic acid ethyl ester (25 mg, 0.07 mmol). 8-Cyclohexyl-5-oxo-2-(2-pyrrolidin-1-yl-ethylamino)-5,8-dihydro-pyrido[2,3-d]pyrimidine-6-carboxylic acid ethyl ester was obtained as a white solid (18 mg, 80%). Mass Spectrum (LCMS, ESI pos.) Calcd. For $C_{22}H_{31}N_5O_3$: 414.24 (M+H). Found: 414.3.

Step B. 8-Cyclohexyl-5-oxo-2-(2-pyrrolidin-1-yl-ethylamino)-5,8-dihydro-pyrido[2,3-d]pyrimidine-6-carboxylic acid amide Using the procedure outlined in Example 28 Step G, 8-cyclohexyl-5-oxo-2-(2-pyrrolidin-1-yl-ethylamino)-5,8-dihydro-pyrido[2,3-d]pyrimidine-6-carboxylic acid amide was obtained as a white solid (1.3 mg, 80%) from 8-cyclohexyl-5-oxo-2-(2-pyrrolidin-1-yl-ethylamino)-5,8-dihydro-pyrido[2,3-d]pyrimidine-6-carboxylic acid ethyl ester (1.6 mg, 0.003 mmol). $^1$H NMR (400 MHz, CDCl$_3$) δ (ppm): 9.50 (br, 1H), 9.19 (s, 1H), 8.73 (s, 1H), 6.49 (br, 1H), 5.78 (br, 1H), 5.15 (m, 1H), 3.52 (m, 2H), 2.71 (m, 2H), 2.54 (m, 4H), 2.20-1.20 (m, 14H). Mass Spectrum (LCMS, ESI pos.) Calcd. For $C_{20}H_{28}N_6O_2$: 385.23 (M+H). Found: 385.2.

Example 37

8-Cyclohexyl-2-[2-(4-methoxy-phenyl)-ethylamino]-5-oxo-5,8-dihydro-pyrido[2,3-d]pyrimidine-6-carboxylic acid amide (Cpd 37)

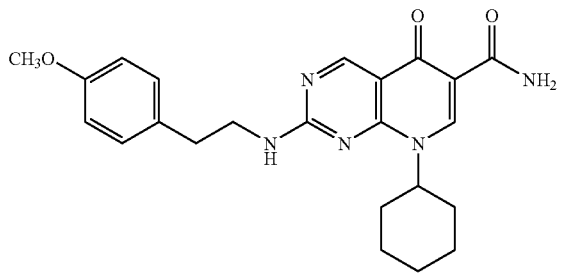

Step A. 8-Cyclohexyl-5-oxo-2-[2-(4-methoxy-phenyl)-ethylamino]-5,8-dihydro-pyrido[2,3-d]pyrimidine-6-carboxylic acid ethyl ester Using the procedure outlined in Example 28 Step F, the title compound was prepared from 2-(4-methoxy-phenyl)-ethylamine and 8-cyclohexyl-2-methanesulfonyl-5-oxo-5,8-dihydro-pyrido[2,3-d]pyrimidine-6-carboxylic acid ethyl ester (from Example 35 (Step E), 35 mg, 0.09 mmol). 8-Cyclohexyl-5-oxo-2-[2-(4-methoxy-phenyl)-ethylamino]-5,8-dihydro-pyrido[2,3-d]pyrimidine-6-carboxylic acid ethyl ester was obtained as a white solid (30 mg, 85%). Mass Spectrum (LCMS, ESI pos.) Calcd. For $C_{25}H_{30}N_4O_4$: 451.23 (M+H). Found: 451.2.

Step B. 8-Cyclohexyl-2-[2-(4-methoxy-phenyl)-ethylamino]-5-oxo-5,8-dihydro-pyrido[2,3-d]pyrimidine-6-carboxylic acid amide Using the procedure outlined in Example 28 Step G, 8-cyclohexyl-5-oxo-2-[2-(4-methoxy-phenyl)-ethylamino]-5,8-dihydro-pyrido[2,3-d]pyrimidine-6-carboxylic acid amide was obtained as a white solid (5.4 mg, 90%) from 8-cyclohexyl-5-oxo-2-[2-(4-methoxy-phenyl)-ethylamino]-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.54 (br, 1H), 9.19 (s, 1H), 8.76 (s, 1H), 7.12 (d, J=8.3 Hz, 2H), 6.83 (d, J=8.3 Hz, 2H), 5.96 (br, 1H), 5.16 (m, 1H), 3.77 (s, 3H), 3.69 (t, J=7.0 Hz, 2H), 2.89 (t, J=7.0 Hz, 2H), 2.10-1.20 (m, 10H). Mass Spectrum (LCMS, ESI pos.) Calcd. For $C_{23}H_{27}N_5O_3$: 422.21 (M+H). Found: 422.2.

Example 38

8-Cyclohexyl-5-oxo-2-(2-piperidin-1-yl-ethylamino)-5,8-dihydro-pyrido[2,3-d]pyrimidine-6-carboxylic acid amide (Cpd 38)

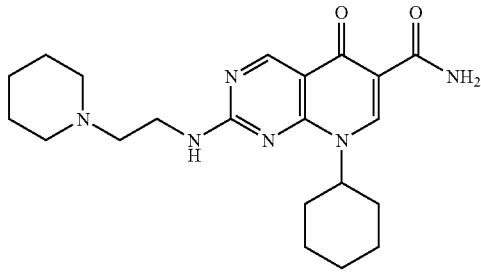

Step A. 8-Cyclohexyl-5-oxo-2-(2-piperidin-1-yl-ethylamino)-5,8-dihydro-pyrido[2,3-d]pyrimidine-6-carboxylic acid ethyl ester Using the procedure outlined in Example 28 Step F, the title compound was prepared from 2-piperidin-1-yl-ethylamine and 8-cyclohexyl-2-methanesulfonyl-5-oxo-5,8-dihydro-pyrido[2,3-d]pyrimidine-6-carboxylic acid ethyl ester (25 mg, 0.06 mmol). 8-Cyclohexyl-5-oxo-2-(2-piperidin-1-yl-ethylamino)-5,8-dihydro-pyrido[2,3-d]pyrimidine-6-carboxylic acid ethyl ester was obtained as a white solid (20 mg, 80%). Mass Spectrum (LCMS, ESI pos.) Calcd. For $C_{23}H_{33}N_5O_3$: 428.26 (M+H). Found: 428.3.

Step B. 8-Cyclohexyl-5-oxo-2-(2-piperidin-1-yl-ethylamino)-5,8-dihydro-pyrido[2,3-d]pyrimidine-6-carboxylic acid amide Using the procedure outlined in Example 28 Step G, 8-cyclohexyl-5-oxo-2-(2-piperidin-1-yl-ethylamino)-5,8-dihydro-pyrido[2,3-d]pyrimidine-6-carboxylic acid amide was obtained as a white solid (6.0 mg, 100%) from 8-cyclohexyl-5-oxo-2-(2-piperidin-1-yl-ethylamino)-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.57 (br, 1H), 9.26 (s, 1H), 8.79 (s, 1H), 6.42 (br, 1H), 5.70 (br, 1H), 5.18 (m, 1H), 3.53 (m, 2H), 2.59 (m, 2H), 2.44 (m, 4H), 2.05-1.20 (m, 16H). Mass Spectrum (LCMS, ESI pos.) Calcd. For $C_{21}H_{30}N_6O_2$: 399.24 (M+H). Found: 399.2.

Example 39

8-Cyclohexyl-2-(2-morpholin-4-yl-ethylamino)-5-oxo-5,8-dihydro-pyrido[2,3-d]pyrimidine-6-carboxylic acid amide (Cpd 39)

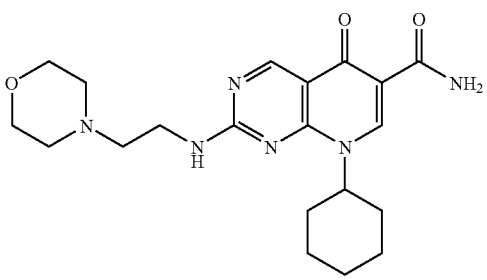

Step A. 8-Cyclohexyl-5-oxo-2-(2-morpholin-4-yl-ethylamino)-5,8-dihydro-pyrido[2,3-d]pyrimidine-6-carboxylic acid ethyl ester Using the procedure outlined in Example 28 Step F, the title compound was prepared from 2-morpholin-4-yl-ethylamine and 8-cyclohexyl-2-methanesulfonyl-5-oxo-5,8-dihydro-pyrido[2,3-d]pyrimidine-6-carboxylic acid ethyl ester (30 mg, 0.08 mmol). 8-Cyclohexyl-5-oxo-2-(2-morpholin-4-yl-ethylamino)-5,8-dihydro-pyrido[2,3-d]pyrimidine-6-carboxylic acid ethyl ester was obtained as a white solid (25 mg, 80%). Mass Spectrum (LCMS, ESI pos.) Calcd. For $C_{22}H_{31}N_5O_4$: 430.24 (M+H). Found: 430.2.

Step B. 8-Cyclohexyl-2-(2-morpholin-4-yl-ethylamino)-5-oxo-5,8-dihydro-pyrido[2,3-d]pyrimidine-6-carboxylic acid amide Using the procedure outlined in Example 28 Step G, 8-Cyclohexyl-5-oxo-2-(2-morpholin-4-yl-ethylamino)-5,8-dihydro-pyrido[2,3-d]pyrimidine-6-carboxylic acid amide was obtained as a white solid (4.4 mg, 90%) from 8-Cyclohexyl-5-oxo-2-(2-morpholin-4-yl-ethylamino)-5,8-dihydro-pyrido[2,3-d]pyrimidine-6-carboxylic acid ethyl ester (5.0 mg, 0.012 mmol). $^1$H NMR (400 MHz, CDCl$_3$) δ (ppm): 9.56 (br, 1H), 9.27 (s, 1H), 8.79 (s, 1H), 6.34 (br, 1H), 5.70 (br, 1H), 5.18 (m, 1H), 3.74 (m, 4H), 3.58 (m, 2H), 2.66 (m, 2H), 2.53 (m, 4H), 2.05-1.20 (m, 10H). Mass Spectrum (LCMS, ESI pos.) Calcd. For $C_{20}H_{28}N_6O_3$: 401.22 (M+H). Found: 401.2.

Example 40

8-Cyclohexyl-2-(3,5-dimethoxy-benzylamino)-5-oxo-5,8-dihydro-pyrido[2,3-d]pyrimidine-6-carboxylic acid amide (Cpd 40)

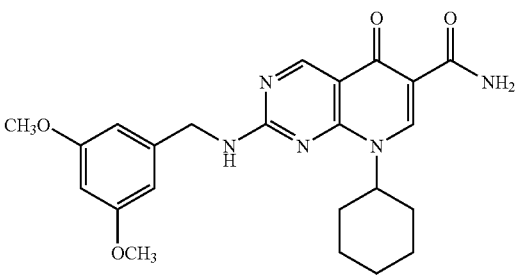

Step A. 8-Cyclohexyl-5-oxo-2-(3,5-dimethoxy-benzylamino)-5,8-dihydro-pyrido[2,3-d]pyrimidine-6-carboxylic acid ethyl ester Using the procedure outlined in Example 28 Step F, the title compound was prepared from 3,5-dimethoxy-benzylamine and 8-cyclohexyl-2-methanesulfonyl-5-oxo-5,8-dihydro-pyrido[2,3-d]pyrimidine-6-carboxylic acid ethyl ester (33 mg, 0.08 mmol). 8-Cyclohexyl-5-oxo-2-(3,5-dimethoxy-benzylamino)-5,8-dihydro-pyrido[2,3-d]pyrimidine-6-carboxylic acid ethyl ester was obtained as a white solid (29 mg, 90%). Mass Spectrum (LCMS, ESI pos.) Calcd. For $C_{25}H_{30}N_4O_5$: 467.22 (M+H). Found: 467.2.

Step B. 8-Cyclohexyl-2-(3,5-dimethoxy-benzy-lamino)-5-oxo-5,8-dihydro-pyrido[2,3-d]pyrimidine-6-carboxylic acid amide Using the procedure outlined in Example 28 Step G, 8-Cyclohexyl-5-oxo-2-(3,5-dimethoxy-benzylamino)-5,8-dihydro-pyrido[2,3-d]pyrimidine-6-carboxylic acid amide was obtained as a white solid (5.7 mg, 95%) from 8-Cyclohexyl-5-oxo-2-(3,5-dimethoxy-benzylamino)-5,8-dihydro-pyrido[2,3-d]pyrimidine-6-carboxylic acid ethyl ester (6.0 mg, 0.015 mmol). $^1$H NMR (400 MHz, CDCl$_3$) δ (ppm): 9.53 (br, 1H), 9.26 (s, 1H), 8.77 (s, 1H), 6.50 (s, 1H), 6.49 (br, 1H), 6.37 (s, 1H), 5.73 (br, 1H), 5.06 (m, 1H), 4.61 (d, J=5.7 Hz, 2H), 3.77 (s, 6H), 2.00-1.20 (m, 10H). Mass Spectrum (LCMS, ESI pos.) Calcd. For $C_{23}H_{27}N_5O_4$: 438.21 (M+H). Found: 438.2.

Example 41

8-Cyclohexyl-2-(3-imidazol-1-yl-propylamino)-5-oxo-5,8-dihydro-pyrido[2,3-d]pyrimidine-6-carboxylic acid methoxy-amide (Cpd 41)

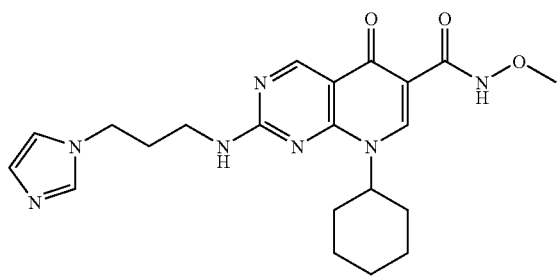

Triethylamine (0.5 mL) was added to a mixture of O-methylhydroxylamine hydrochloride (220 mg) and 2-(3-Imidazol-1-yl-propylamino)-8-indan-5-yl-5-oxo-5,8-dihydro-pyrido[2,3-d]pyrimidine-6-carboxylic acid ethyl ester (from Example 28 Step F, 6.0 mg, 0.013 mmol) in 0.5 mL of methanol. The reaction mixture was kept in a sealed tube at 110° C. for 2 days with stirring. After cooling to room temperature, the solution was diluted with water and extracted with dichloromethane. The crude product, after concentration, was loaded to HPLC for purification (32 mL/min 5-100% MeCN/H$_2$O gradient over 10 min). 2-(3-Imidazol-1-yl-propylamino)-8-cyclohexyl-5-oxo-5,8-dihydro-pyrido[2,3-d]pyrimidine-6-carboxylic acid methoxy-amide was obtained as a white solid (4.3 mg, 70%). $^1$H NMR (400 MHz, CDCl$_3$) δ (ppm): 12.02 (br, 1H), 9.26 (s, 1H), 8.75 (s, 1H), 7.32 (br, 1H), 7.10 (s, 1H), 6.95 (br, 1H), 5.82 (br, 1H), 5.06 (m, 1H), 4.10 (t, J=6.7 Hz, 2H), 3.88 (s, 3H), 3.51 (m, 2H), 2.20-1.20 (m, 12H). Mass Spectrum (LCMS, ESI pos.) Calcd. For $C_{21}H_{27}N_7O_3$: 426.22 (M+H). Found: 426.2.

Example 42

8-Cyclohexyl-2-(3-dimethylamino-propylamino)-5-oxo-5,8-dihydro-pyrido[2,3-d]pyrimidine-6-carboxylic acid methoxy-amide (Cpd 42)

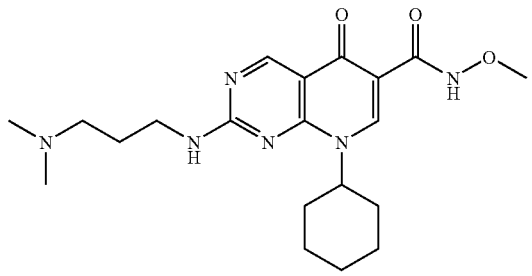

Using the procedure outlined in Example 41, 8-Cyclohexyl-5-oxo-2-(3-dimethylamino-propylamino)-5,8-dihydro-pyrido[2,3-d]pyrimidine-6-carboxylic acid methoxy-amide was obtained as a white solid (2.4 mg, 80%) from 8-Cyclohexyl-5-oxo-2-(3-dimethylamino-propylamino)-5,8-dihydro-pyrido[2,3-d]pyrimidine-6-carboxylic acid ethyl ester (Example 29, 3.0 mg, 0.007 mmol). $^1$H NMR (400 MHz, CDCl$_3$) δ (ppm): 12.09 (br, 1H), 9.23 (s, 1H), 8.73 (s, 1H), 7.16 (br, 1H), 5.16 (m, 1H), 3.87 (s, 3H), 3.56 (m, 2H), 2.47 (t, J=6.4 Hz, 2H), 2.28 (s, 6H), 2.05-1.20 (m, 12H). Mass Spectrum (LCMS, ESI pos.) Calcd. For $C_{20}H_{30}N_6O_3$: 403.24 (M+H). Found: 403.2.

Example 43

8-Cyclohexyl-2-(3-morpholin-4-yl-propylamino)-5-oxo-5,8-dihydro-pyrido[2,3-d]pyrimidine-6-carboxylic acid methoxy-amide (Cpd 43)

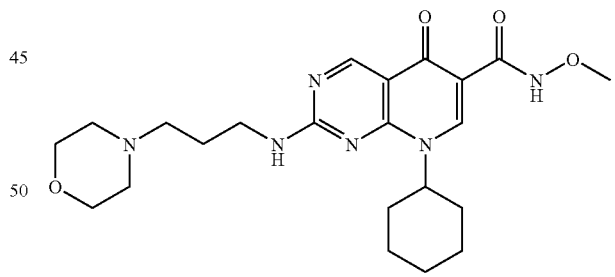

Using the procedure outlined in Example 41, 8-Cyclohexyl-5-oxo-2-(3-morpholin-4-yl-propylamino)-5,8-dihydro-pyrido[2,3-d]pyrimidine-6-carboxylic acid methoxy-amide was obtained as a white solid (2.0 mg, 70%) from 8-Cyclohexyl-5-oxo-2-(3-morpholin-4-yl-propylamino)-5,8-dihydro-pyrido[2,3-d]pyrimidine-6-carboxylic acid ethyl ester (Example 30, 3.0 mg, 0.007 mmol). $^1$H NMR (400 MHz, CDCl$_3$) δ (ppm): 12.09 (br, 1H), 9.23 (s, 1H), 8.73 (s, 1H), 6.97 (br, 1H), 5.15 (m, 1H), 3.88 (s, 3H), 3.77 (m, 4H), 4.59 (m, 2H), 2.51 (m, 2H), 2.00-1.20 (m, 12H). Mass Spectrum (LCMS, ESI pos.) Calcd. For $C_{22}H_{32}N_6O_4$: 445.25 (M+H). Found: 445.3.

Example 44

8-Cyclohexyl-2-(3-methoxy-propylamino)-5-oxo-5,8-dihydro-pyrido[2,3-d]pyrimidine-6-carboxylic acid methoxy-amide (Cpd 44)

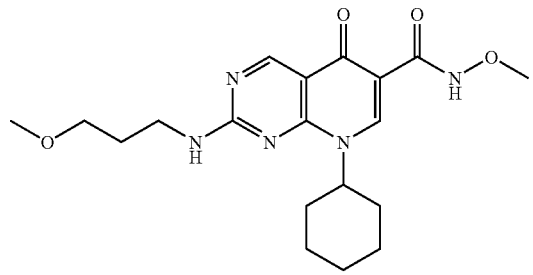

Using the procedure outlined in Example 41, 8-cyclohexyl-5-oxo-2-(3-methoxy-propylamino)-5,8-dihydro-pyrido[2,3-d]pyrimidine-6-carboxylic acid methoxy-amide was obtained as a white solid (2.6 mg, 80%) from 8-Cyclohexyl-5-oxo-2-(3-methoxy-propylamino)-5,8-dihydro-pyrido[2,3-d]pyrimidine-6-carboxylic acid ethyl ester (Example 31, 3.0 mg, 0.007 mmol). $^1$H NMR (400 MHz, CDCl$_3$) δ (ppm): 12.08 (br, 1H), 9.23 (s, 1H), 8.74 (s, 1H), 6.24 (br, 1H), 5.17 (m, 1H), 3.88 (s, 3H), 3.65-3.50 (m, 4H), 3.37 (s, 3H), 2.51 (m, 2H), 2.00-1.20 (m, 12H). Mass Spectrum (LCMS, ESI pos.) Calcd. For $C_{19}H_{27}N_5O_4$: 390.21 (M+H). Found: 390.2.

Example 45

8-Cyclohexyl-2-[3-(4-methyl-piperazin-1-yl)-propylamino]-5-oxo-5,8-dihydro-pyrido[2,3-d]pyrimidine-6-carboxylic acid methoxy-amide (Cpd 45)

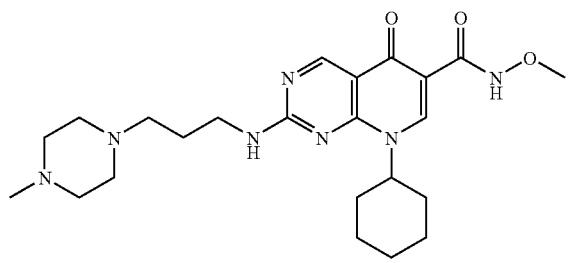

Using the procedure outlined in Example 41, 8-cyclohexyl-5-oxo-2-[3-(4-methyl-piperazin-1-yl)-propylamino]-5,8-dihydro-pyrido[2,3-d]pyrimidine-6-carboxylic acid methoxy-amide was obtained as a white solid (3.2 mg, 80%) from 8-Cyclohexyl-5-oxo-2-[3-(4-methyl-piperazin-1-yl)-propylamino]-5,8-dihydro-pyrido[2,3-d]pyrimidine-6-carboxylic acid ethyl ester (Example 33, 4.0 mg, 0.01 mmol). $^1$H NMR (400 MHz, CDCl$_3$) δ (ppm): 12.09 (br, 1H), 9.22 (s, 1H), 8.73 (s, 1H), 7.05 (br, 1H), 5.15 (m, 1H), 3.87 (s, 3H), 3.56 (m, 2H), 2.54 (m, 10H), 2.34 (s, 3H), 1.95-1.20 (m, 12H). Mass Spectrum (LCMS, ESI pos.) Calcd. For $C_{23}H_{35}N_7O_3$: 458.28 (M+H). Found: 458.3.

Example 46

8-Cyclohexyl-5-oxo-2-(3-pyrrolidin-1-yl-propylamino)-5,8-dihydro-pyrido[2,3-d]pyrimidine-6-carboxylic acid methoxy-amide (Cpd 46)

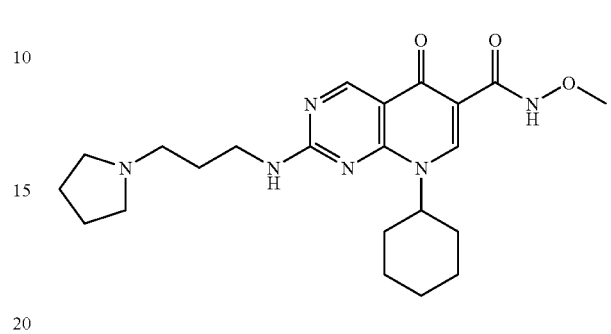

Using the procedure outlined in Example 41, 8-cyclohexyl-5-oxo-2-(3-pyrrolidin-1-yl-propylamino)-5,8-dihydro-pyrido[2,3-d]pyrimidine-6-carboxylic acid methoxy-amide was obtained as a white solid (1.5 mg, 75%) from 8-cyclohexyl-5-oxo-2-(3-pyrrolidin-1-yl-propylamino)-5,8-dihydro-pyrido[2,3-d]pyrimidine-6-carboxylic acid ethyl ester (Example 34, 2.0 mg, 0.005 mmol). $^1$H NMR (400 MHz, CDCl$_3$) δ (ppm): 12.09 (br, 1H), 9.22 (s, 1H), 8.73 (s, 1H), 7.02 (br, 1H), 5.15 (m, 1H), 3.87 (s, 3H), 3.59 (m, 2H), 2.70-2.50 (m, 6H), 2.00-1.20 (m, 12H). Mass Spectrum (LCMS, ESI pos.) Calcd. For $C_{22}H_{32}N_6O_3$: 429.25 (M+H). Found: 429.3.

Example 47

8-Cyclohexyl-2-(2-methoxy-ethylamino)-5-oxo-5,8-dihydro-pyrido[2,3-d]pyrimidine-6-carboxylic acid methoxy-amide (Cpd 47)

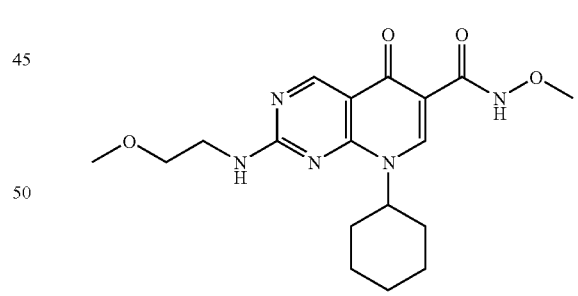

Using the procedure outlined in Example 41, 8-cyclohexyl-5-oxo-2-(2-methoxy-ethylamino)-5,8-dihydro-pyrido[2,3-d]pyrimidine-6-carboxylic acid methoxy-amide was obtained as a white solid (2.0 mg, 70%) from 8-cyclohexyl-5-oxo-2-(2-methoxy-ethylamino)-5,8-dihydro-pyrido[2,3-d]pyrimidine-6-carboxylic acid ethyl ester (Example 35, 3.0 mg, 0.007 mmol). $^1$H NMR (400 MHz, CDCl$_3$) δ (ppm): 12.06 (br, 1H), 9.25 (s, 1H), 8.74 (s, 1H), 6.07 (br, 1H), 5.14 (m, 1H), 3.88 (s, 3H), 3.70-3.60 (m, 4H), 3.41 (s, 3H), 2.04-1.20 (m, 10H). Mass Spectrum (LCMS, ESI pos.) Calcd. For $C_{18}H_{25}N_5O_4$: 376.19 (M+H). Found: 376.2.

Example 48

8-Cyclohexyl-5-oxo-2-(2-pyrrolidin-1-yl-ethylamino)-5,8-dihydro-pyrido[2,3-d]pyrimidine-6-carboxylic acid methoxy-amide (Cpd 48)

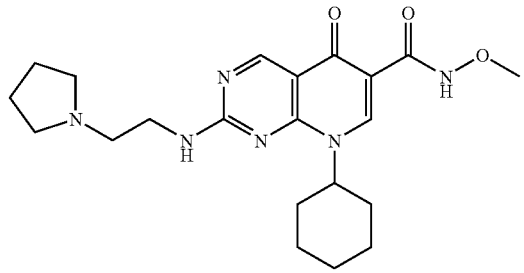

Using the procedure outlined in Example 41, 8-cyclohexyl-5-oxo-2-(2-pyrrolidin-1-yl-ethylamino)-5,8-dihydro-pyrido[2,3-d]pyrimidine-6-carboxylic acid methoxy-amide was obtained as a white solid (1.2 mg, 60%) from 8-cyclohexyl-5-oxo-2-(2-pyrrolidin-1-yl-ethylamino)-5,8-dihydro-pyrido[2,3-d]pyrimidine-6-carboxylic acid ethyl ester (Example 36, 2.0 mg, 0.005 mmol). $^1$H NMR (400 MHz, CDCl$_3$) δ (ppm): 12.08 (br, 1H), 9.24 (s, 1H), 8.74 (s, 1H), 6.40 (br, 1H), 5.19 (m, 1H), 3.88 (s, 3H), 3.56 (q, J=5.6 Hz, 2H), 2.76 (t, J=6.5 Hz, 2H), 2.58 (m, 4H), 2.04-1.20 (m, 14H). Mass Spectrum (LCMS, ESI pos.) Calcd. For C$_{21}$H$_{30}$N$_6$O$_3$: 415.24 (M+H). Found: 415.3.

Example 49

8-Cyclohexyl-2-[2-(4-methoxy-phenyl)-ethylamino]-5-oxo-5,8-dihydro-pyrido[2,3-d]pyrimidine-6-carboxylic acid methoxy-amide (Cpd 49)

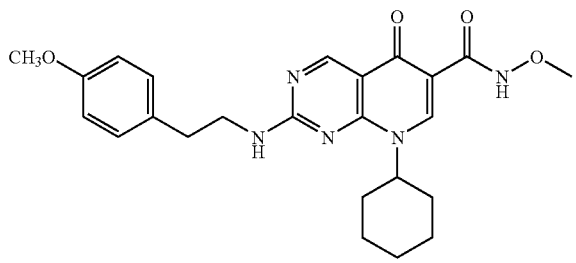

Using the procedure outlined in Example 41, 8-cyclohexyl-5-oxo-2-[2-(4-methoxy-phenyl)-ethylamino]-5,8-dihydro-pyrido[2,3-d]pyrimidine-6-carboxylic acid methoxy-amide was obtained as a white solid (3.3 mg, 80%) from 8-cyclohexyl-5-oxo-2-[2-(4-methoxy-phenyl)-ethylamino]-5,8-dihydro-pyrido[2,3-d]pyrimidine-6-carboxylic acid ethyl ester (Example 37, 4.0 mg, 0.01 mmol). $^1$H NMR (400 MHz, CDCl$_3$) δ (ppm): 12.06 (br, 1H), 9.21 (s, 1H), 8.75 (s, 1H), 7.14 (d, J=8.5 Hz, 2H), 6.85 (d, J=8.5 Hz, 2H), 5.84 (br, 1H), 5.18 (m, 1H), 3.88 (s, 3H), 3.79 (s, 3H), 3.72 (q, J=6.6 Hz, 2H), 2.91 (t, J=7.0 Hz, 2H), 2.10-1.20 (m, 10H). Mass Spectrum (LCMS, ESI pos.) Calcd. For C$_{24}$H$_{29}$N$_5$O$_4$: 452.22 (M+H). Found: 452.2.

Example 50

8-Cyclohexyl-5-oxo-2-(2-piperidin-1-yl-ethylamino)-5,8-dihydro-pyrido[2,3-d]pyrimidine-6-carboxylic acid methoxy-amide (Cpd 50)

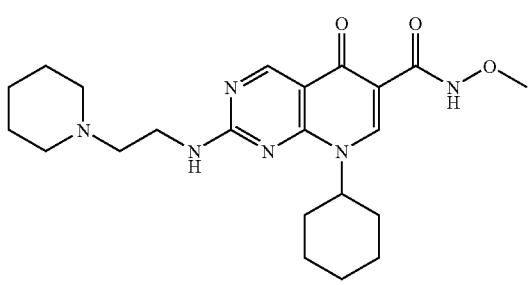

Using the procedure outlined in Example 41, 8-cyclohexyl-5-oxo-2-(2-piperidin-1-yl-ethylamino)-5,8-dihydro-pyrido[2,3-d]pyrimidine-6-carboxylic acid methoxy-amide was obtained as a white solid (1.0 mg, 50%) from 8-cyclohexyl-5-oxo-2-(2-piperidin-1-yl-ethylamino)-5,8-dihydro-pyrido[2,3-d]pyrimidine-6-carboxylic acid ethyl ester (Example 38, 2.0 mg, 0.005 mmol). $^1$H NMR (400 MHz, CDCl$_3$) δ (ppm): 12.08 (br, 1H), 9.24 (s, 1H), 8.73 (s, 1H), 6.43 (br, 1H), 5.18 (m, 1H), 3.88 (s, 3H), 3.53 (m, 2H), 2.60-2.40 (m, 6H) 2.00-1.20 (m, 16H). Mass Spectrum (LCMS, ESI pos.) Calcd. For C$_{22}$H$_{32}$N$_6$O$_3$: 429.25 (M+H). Found: 429.2.

Example 51

8-Cyclohexyl-2-(2-morpholin-4-yl-ethylamino)-5-oxo-5,8-dihydro-pyrido[2,3-d]pyrimidine-6-carboxylic acid methoxy-amide (Cpd 51)

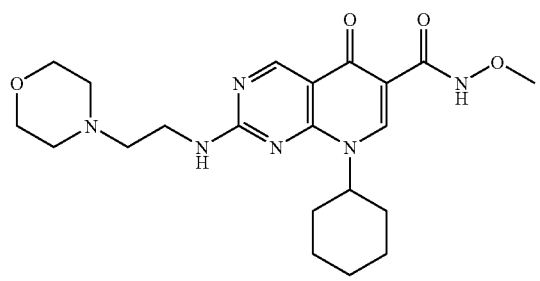

Using the procedure outlined in Example 41, 8-cyclohexyl-5-oxo-2-(2-morpholin-4-yl-ethylamino)-5,8-dihydro-pyrido[2,3-d]pyrimidine-6-carboxylic acid methoxy-amide was obtained as a white solid (2.2 mg, 70%) from 8-cyclohexyl-5-oxo-2-(2-morpholin-4-yl-ethylamino)-5,8-dihydro-pyrido[2,3-d]pyrimidine-6-carboxylic acid ethyl ester (Example 39, 3.0 mg, 0.007 mmol). $^1$H NMR (400 MHz, CDCl$_3$) δ (ppm): 12.06 (br, 1H), 9.25 (s, 1H), 8.74 (s, 1H), 6.37 (br, 1H), 5.17 (m, 1H), 3.88 (s, 3H), 3.74 (m, 4H), 3.57 (m, 2H), 2.67 (m, 2H), 2.53 (m, 4H), 2.00-1.20 (m, 10H). Mass Spectrum (LCMS, ESI pos.) Calcd. For C$_{21}$H$_{30}$N$_6$O$_4$: 431.23 (M+H). Found: 431.2.

Example 52

8-Cyclohexyl-2-(3,5-dimethoxy-benzylamino)-5-oxo-5,8-dihydro-pyrido[2,3-d]pyrimidine-6-carboxylic acid methoxy-amide (Cpd 52)

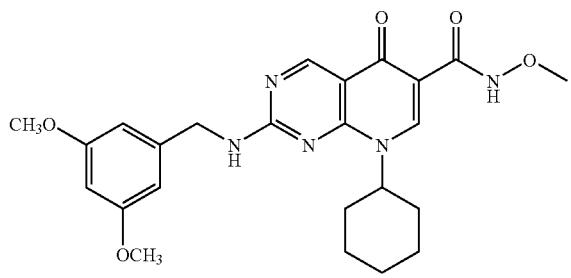

Using the procedure outlined in Example 41, 8-cyclohexyl-5-oxo-2-(3,5-dimethoxy-benzylamino)-5,8-dihydro-pyrido[2,3-d]pyrimidine-6-carboxylic acid methoxy-amide was obtained as a white solid (3.3 mg, 80%) from 8-cyclohexyl-5-oxo-2-(3,5-dimethoxy-benzylamino)-5,8-dihydro-pyrido[2,3-d]pyrimidine-6-carboxylic acid ethyl ester (Example 40, 4.0 mg, 0.01 mmol). $^1$H NMR (400 MHz, CDCl$_3$) δ (ppm): 12.04 (br, 1H), 9.25 (s, 1H), 8.72 (s, 1H), 6.49 (s, 2H), 6.37 (s, 1H), 6.23 (t, J=5.5 Hz, 1H), 5.05 (m, 1H), 4.06 (d, J=5.5 Hz, 2H), 3.87 (s, 3H), 3.77 (s, 6H), 2.00-1.20 (m, 10H). Mass Spectrum (LCMS, ESI pos.) Calcd. For C$_{24}$H$_{29}$N$_5$O$_5$: 468.22 (M+H). Found: 468.2.

Example 53

8-Cyclohexyl-2-(3-imidazol-1-yl-propylamino)-5-oxo-5,8-dihydro-pyrido[2,3-d]pyrimidine-6-carboxylic acid methylamide (Cpd 53)

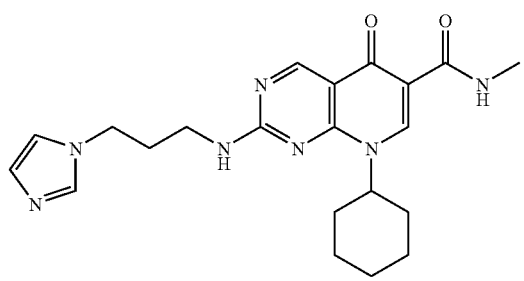

A solution of methylamine (1N, 1 ml in methanol) was added to 2-(3-imidazol-1-yl-propylamino)-8-cyclohexyl-5-oxo-5,8-dihydro-pyrido[2,3-d]pyrimidine-6-carboxylic acid ethyl ester (Example 28, Step F, 7.0 mg, 0.015 mmol). The mixture was kept in a sealed tube at 110° C. with stirring for 2 days. The solution, after cooling down to room temperature, was loaded to hplc for purification. 8-Cyclohexyl-2-(3-imidazol-1-yl-propylamino)-5-oxo-5,8-dihydro-pyrido[2,3-d]pyrimidine-6-carboxylic acid methylamide was obtained as a white solid (5.5 mg, 80%). $^1$H NMR (400 MHz, CDCl$_3$) δ (ppm): 9.67 (br, 1H), 9.26 (s, 1H), 8.79 (s, 1H), 7.51 (br, 1H), 7.10 (s, 1H), 6.93 (br, 1H), 5.95 (br, 1H), 5.06 (m, 1H), 4.10 (t, J=6.8 Hz, 2H), 3.50 (m, 2H), 2.98 (d, J=4.9 Hz, 3), 2.20-1.20 (m, 12H). Mass Spectrum (LCMS, ESI pos.) Calcd. For C$_{21}$H$_{27}$N$_7$O$_2$: 410.22 (M+H). Found: 410.2.

Example 54

8-Cyclohexyl-2-(3-dimethylamino-propylamino)-5-oxo-5,8-dihydro-pyrido[2,3-d]pyrimidine-6-carboxylic acid methylamide (Cpd 54)

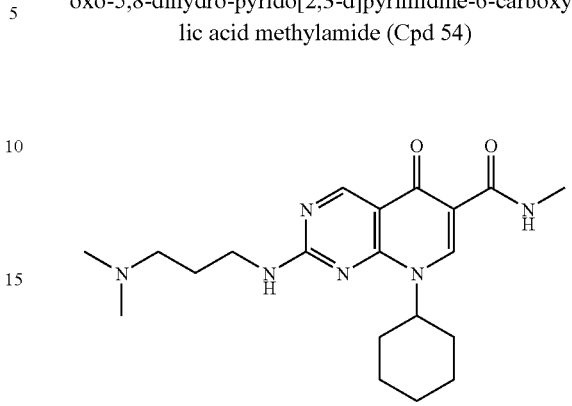

Using the procedure outlined in Example 53, 8-cyclohexyl-5-oxo-2-(3-dimethylamino-propylamino)-5,8-dihydro-pyrido[2,3-d]pyrimidine-6-carboxylic acid methoxy-amide was obtained as a white solid (5.4 mg, 80%) from 8-cyclohexyl-5-oxo-2-(3-dimethylamino-propylamino)-5,8-dihydro-pyrido[2,3-d]pyrimidine-6-carboxylic acid ethyl ester (Example 29, 7 mg, 0.016 mmol). $^1$H NMR (400 MHz, CDCl$_3$) δ (ppm): 9.73 (br, 1H), 9.23 (s, 1H), 8.77 (s, 1H), 7.06 (br, 1H), 5.15 (m, 1H), 3.66 (m, 2H), 2.98 (d, J=4.9 Hz, 3H), 2.46 (t, J=6.5 Hz, 2H), 2.27 (s, 6H), 2.05-1.20 (m, 12H). Mass Spectrum (LCMS, ESI pos.) Calcd. For C$_{20}$H$_{30}$N$_6$O$_2$: 387.24 (M+H). Found: 387.2.

Example 55

8-Cyclohexyl-2-(3-morpholin-4-yl-propylamino)-5-oxo-5,8-dihydro-pyrido[2,3-d]pyrimidine-6-carboxylic acid methylamide (Cpd 55)

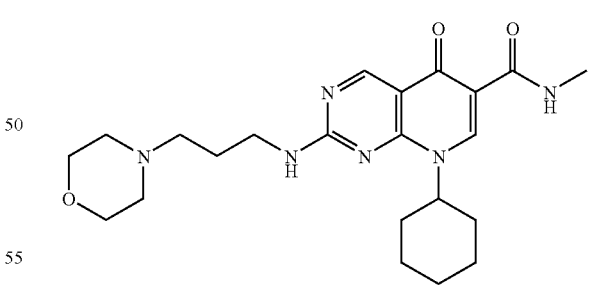

Using the procedure outlined in Example 53, 8-cyclohexyl-5-oxo-2-(3-morpholin-4-yl-propylamino)-5,8-dihydro-pyrido[2,3-d]pyrimidine-6-carboxylic acid methoxy-amide was obtained as a white solid (6.0 mg, 85%) from 8-cyclohexyl-5-oxo-2-(3-morpholin-4-yl-propylamino)-5,8-dihydro-pyrido[2,3-d]pyrimidine-6-carboxylic acid ethyl ester (Example 30, 7.0 mg, 0.016 mmol). $^1$H NMR (400 MHz, CDCl$_3$) δ (ppm): 9.73 (br, 1H), 9.23 (s, 1H), 8.77 (s, 1H), 6.91 (br, 1H), 5.13 (m, 1H), 3.75 (m, 4H), 3.58 (m, 2H), 2.98 (d, J=4.8 Hz, 3H), 2.55-2.40 (m, 6H), 2.00-1.20 (m, 12H). Mass Spectrum (LCMS, ESI pos.) Calcd. For $C_{22}H_{32}N_6O_2$: 429.25 (M+H). Found: 429.2.

Example 56

8-Cyclohexyl-2-(3-methoxy-propylamino)-5-oxo-5,8-dihydro-pyrido[2,3-d]pyrimidine-6-carboxylic acid methylamide (Cpd 56)

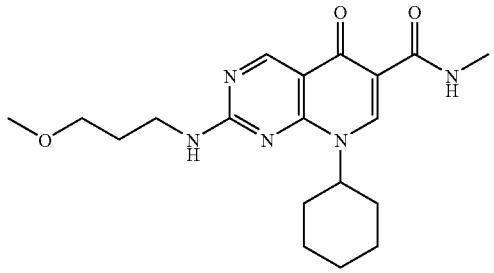

Using the procedure outlined in Example 53, 8-cyclohexyl-5-oxo-2-(3-methoxy-propylamino)-5,8-dihydro-pyrido[2,3-d]pyrimidine-6-carboxylic acid methoxy-amide was obtained as a white solid (4.9 mg, 80%) from 8-cyclohexyl-5-oxo-2-(3-methoxy-propylamino)-5,8-dihydro-pyrido[2,3-d]pyrimidine-6-carboxylic acid ethyl ester (Example 31, 6.0 mg, 0.015 mmol). $^1$H NMR (400 MHz, CDCl$_3$) δ (ppm): 9.72 (br, 1H), 9.23 (s, 1H), 8.78 (s, 1H), 6.22 (br, 1H), 5.15 (m, 1H), 3.65-3.50 (m, 4H), 3.37 (s, 3H), 2.98 (d, J=4.9 Hz, 3H), 2.05-1.20 (m, 12H). Mass Spectrum (LCMS, ESI pos.) Calcd. For $C_{19}H_{27}N_5O_3$: 374.21 (M+H). Found: 374.2.

Example 57

8-Cyclohexyl-2-(2-methoxy-ethylamino)-5-oxo-5,8-dihydro-pyrido[2,3-d]pyrimidine-6-carboxylic acid methylamide (Cpd 57)

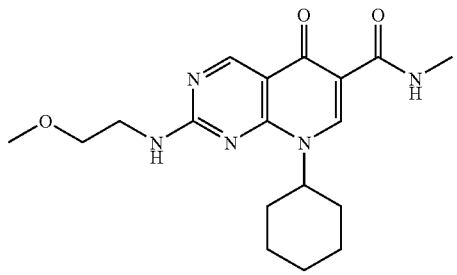

Using the procedure outlined in Example 53, 8-cyclohexyl-5-oxo-2-(2-methoxy-ethylamino)-5,8-dihydro-pyrido[2,3-d]pyrimidine-6-carboxylic acid methoxy-amide was obtained as a white solid (5.6 mg, 80%) from 8-cyclohexyl-5-oxo-2-(2-methoxy-ethylamino)-5,8-dihydro-pyrido[2,3-d]pyrimidine-6-carboxylic acid ethyl ester (Example 35, 7.0 mg, 0.017 mmol). $^1$H NMR (400 MHz, CDCl$_3$) δ (ppm): 9.70 (br, 1H), 9.25 (s, 1H), 8.78 (s, 1H), 6.14 (br, 1H), 5.13 (m, 1H), 3.70-3.60 (m, 4H), 3.41 (s, 3H), 2.99 (d, J=4.9 Hz, 3H), 2.04-1.2 (m, 10H). Mass Spectrum (LCMS, ESI pos.) Calcd. For $C_{18}H_{25}N_5O_3$: 360.20 (M+H). Found: 360.2.

Example 58

8-Cyclohexyl-2-[2-(4-methoxy-phenyl)-ethylamino]-5-oxo-5,8-dihydro-pyrido[2,3-d]pyrimidine-6-carboxylic acid methylamide (Cpd 58)

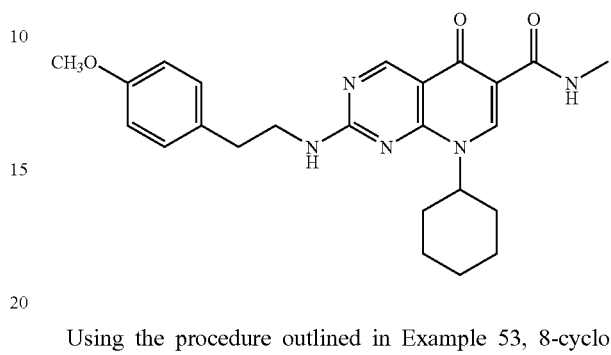

Using the procedure outlined in Example 53, 8-cyclohexyl-5-oxo-2-[2-(4-methoxy-phenyl)-ethylamino]-5,8-dihydro-pyrido[2,3-d]pyrimidine-6-carboxylic acid methoxy-amide was obtained as a white solid (5.9 mg, 85%) from 8-cyclohexyl-5-oxo-2-[2-(4-methoxy-phenyl)-ethylamino]-5,8-dihydro-pyrido[2,3-d]pyrimidine-6-carboxylic acid ethyl ester (Example 37, 7.0 mg, 0.017 mmol). $^1$H NMR (400 MHz, CDCl$_3$) δ (ppm): 9.71 (br, 1H), 9.21 (s, 1H), 8.79 (s, 1H), 7.14 (d, J=8.5 Hz, 2H), 6.85 (d, J=8.5 Hz, 2H), 5.87 (br, 1H), 5.18 (m, 1H), 3.78 (s, 3H), 3.72 (q, J=6.4 Hz, 2H), 2.98 (d, J=4.9 Hz, 3H), 2.91 (t, J=7.0 Hz, 2H), 2.10-0.80 (m, 10H). Mass Spectrum (LCMS, ESI pos.) Calcd. For $C_{24}H_{29}N_5O_3$: 436.23 (M+H). Found: 436.2.

Example 59

8-Cyclohexyl-5-oxo-2-(2-piperidin-1-yl-ethylamino)-5,8-dihydro-pyrido[2,3-d]pyrimidine-6-carboxylic acid methylamide (Cpd 59)

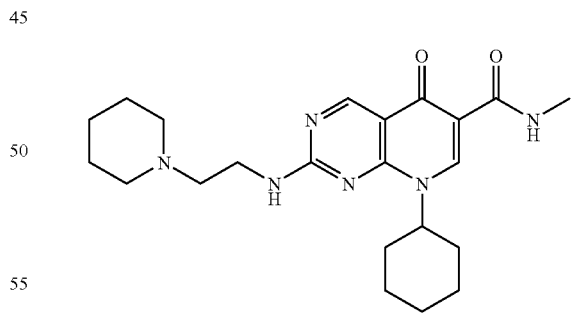

Using the procedure outlined in Example 53, 8-cyclohexyl-5-oxo-2-(2-piperidin-1-yl-ethylamino)-5,8-dihydro-pyrido[2,3-d]pyrimidine-6-carboxylic acid methoxy-amide was obtained as a white solid (6.0 mg, 85%) from 8-cyclohexyl-5-oxo-2-(2-piperidin-1-yl-ethylamino)-5,8-dihydro-pyrido[2,3-d]pyrimidine-6-carboxylic acid ethyl ester (Example 38, 7.0 mg, 0.017 mmol). $^1$H NMR (400 MHz, CDCl$_3$) δ (ppm): 9.72 (br, 1H), 9.24 (s, 1H), 8.78 (s, 1H), 6.40 (br, 1H), 5.17 (m, 1H), 3.52 (m, 2H), 2.98 (d, J=4.9 Hz, 3H), 2.58

(t, J=6.2 Hz, 2H), 2.43 (m, 4H), 2.00-1.2 (m, 16H). Mass Spectrum (LCMS, ESI pos.) Calcd. For $C_{22}H_{32}N_6O_2$: 413.26 (M+H). Found: 413.3.

Example 60

8-Cyclohexyl-2-(2-morpholin-4-yl-ethylamino)-5-oxo-5,8-dihydro-pyrido[2,3-d]pyrimidine-6-carboxylic acid methylamide (Cpd 60)

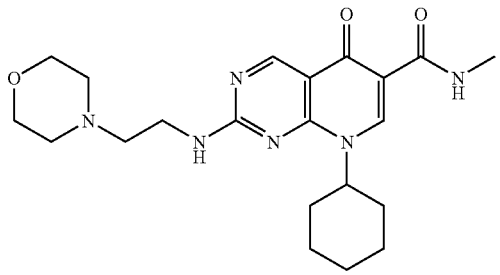

Using the procedure outlined in Example 53, 8-cyclohexyl-5-oxo-2-(2-morpholin-4-yl-ethylamino)-5,8-dihydro-pyrido[2,3-d]pyrimidine-6-carboxylic acid methoxy-amide was obtained as a white solid (5.8 mg, 85%) from 8-cyclohexyl-5-oxo-2-(2-morpholin-4-yl-ethylamino)-5,8-dihydro-pyrido[2,3-d]pyrimidine-6-carboxylic acid ethyl ester (Example 39, 7.0 mg, 0.017 mmol). $^1$H NMR (400 MHz, CDCl$_3$) δ (ppm): 9.70 (br, 1H), 9.25 (s, 1H), 8.78 (s, 1H), 6.34 (br, 1H), 5.16 (m, 1H), 3.73 (m, 4H), 3.55 (m, 2H), 2.98 (d, J=4.9 Hz, 3H), 2.65 (t, J=6.0 Hz, 2H), 2.51 (m, 4H), 2.00-1.20 (m, 10H). Mass Spectrum (LCMS, ESI pos.) Calcd. For $C_{21}H_{30}N_6O_3$: 415.24 (M+H). Found: 415.3.

Example 61

8-Cyclohexyl-2-(3,5-dimethoxy-benzylamino)-5-oxo-5,8-dihydro-pyrido[2,3-d]pyrimidine-6-carboxylic acid methylamide (Cpd 61)

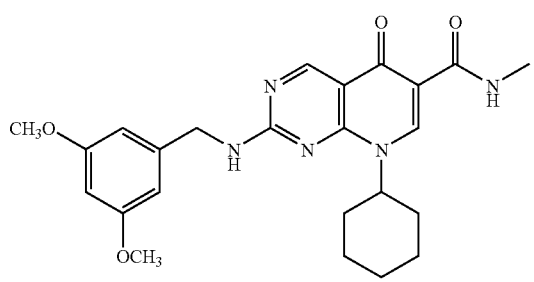

Using the procedure outlined in Example 53, 8-cyclohexyl-5-oxo-2-(3,5-dimethoxy-benzylamino)-5,8-dihydro-pyrido[2,3-d]pyrimidine-6-carboxylic acid methoxy-amide was obtained as a white solid (6.7 mg, 85%) from 8-cyclohexyl-5-oxo-2-(3,5-dimethoxy-benzylamino)-5,8-dihydro-pyrido[2,3-d]pyrimidine-6-carboxylic acid ethyl ester (Example 40, 8.0 mg, 0.016 mmol). $^1$H NMR (400 MHz, CDCl$_3$) δ (ppm): 9.68 (br, 1H), 9.26 (s, 1H), 8.77 (s, 1H), 6.49 (s, 2H), 6.37 (s, 1H), 6.20 (br, 1H), 5.05 (m, 1H), 4.61 (d, J=6.4 Hz, 2H), 3.76 (s, 6H), 2.97 (d, J=4.6 Hz, 3H), 2.00-1.20 (m, 10H). Mass Spectrum (LCMS, ESI pos.) Calcd. For $C_{24}H_{29}N_5O_4$: 452.22 (M+H). Found: 452.2.

BIOLOGICAL EXAMPLES

Example 1

Autophosphorylation, Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms and 16.7 mM MgCl$_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM MgCl$_2$, 2% DMSO. Control reactions were ran in each plate: in positive and negative control wells, assay buffer (made 4% in DMSO) was substituted for the compound; in addition, positive control wells received 1.2 µL of 50 mM ethylenediaminetetraaceticacid (EDTA).

The plates were incubated at room temperature for 45 min. At the end of the incubation, the reaction was quenched with 1.2 µL of 50 mM EDTA (EDTA was not added to the positive control wells at this point; see above). Following a 5-min incubation, each well received 10 µL of a 1:1:3 mixture of anti-phosphotyrosine antibody, 10X, PTK green tracer, 10X (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction.

The percent inhibition is shown in Table 1 at the indicated test concentration. The IC$_{50}$ shown in Table 2 are averages of three independent measurements.

TABLE 1

| c-fms Autophosphorylation Percent InhibitionIC$_{50}$ Values | | |
|---|---|---|
| Cpd | % @ 1 µM | % @ 0.1 µM |
| 1 | 69.1 | 24 |
| 2 | 20 | 15 |
| 7 | 43 | 17 |
| 8 | 46 | 15 |
| 9 | 45 | 16 |
| 10 | 41 | 16 |
| 11 | 50 | 0 |

TABLE 1-continued c-fms Autophosphorylation Percent InhibitionIC$_{50}$ Values

| Cpd | % @ 1 µM | % @ 0.1 µM |
|---|---|---|
| 12 | 13 | 2 |
| 13 | 27 | 7 |
| 14 | 24 | 5 |
| 15 | 29 | 8 |
| 16 | 39 | 12 |
| 17 | 36 | 15 |
| 18 | 35 | 12 |
| 19 | 70 | 36 |
| 20 | 52 | 20 |
| 21 | 82 | 50 |
| 22 | 72 | 40 |
| 23 | 65 | 51 |
| 24 | 59 | 52 |
| 25 | 30 | 6 |
| 26 | 54 | 25 |
| 27 | 41 | 15 |
| 28 | 69 | 31 |
| 29 | 65 | 22 |
| 30 | 68 | 24 |
| 31 | 62 | 25 |
| 32 | 52 | 17 |
| 33 | 70 | 31 |
| 34 | 64 | 31 |
| 35 | 67 | 29 |
| 36 | 49 | 5 |
| 37 | 41 | 29 |
| 38 | 56 | 19 |
| 39 | 59 | 21 |
| 40 | 47 | 10 |
| 41 | 45 | 22 |
| 42 | 40 | 17 |
| 43 | 60 | 32 |
| 44 | 62 | 26 |
| 45 | 67 | 43 |
| 46 | 51 | 28 |
| 47 | 57 | 31 |
| 48 | 18 | 0 |
| 49 | 68 | 38 |
| 50 | 20 | 3 |
| 51 | 44 | 17 |
| 52 | 53 | 23 |
| 53 | 21 | 10 |
| 54 | 26 | 6 |
| 55 | 23 | 13 |
| 56 | 23 | 6 |
| 57 | 20 | 16 |
| 58 | 26 | 13 |
| 59 | 11 | 5 |
| 60 | 18 | 12 |
| 61 | 21 | 3 |

TABLE 1 c-fms Autophosphorylation IC$_{50}$ (µM)

| Cpd | IC$_{50}$ (µM) |
|---|---|
| 3 | 2.3 |
| 4 | 3.3 |
| 5 | 2.6 |
| 6 | 7.1 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

We claim:
1. A compound of Formula I:

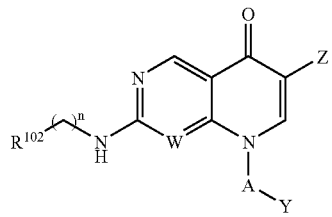

or a salt, stereoisomer, tautomer or ester thereof, wherein:
W is N;
A is absent or alkyl;
Y is a ring selected from cyclohexyl, cyclopentyl, bicyclo [2.2.1]heptyl, phenyl, adamantanyl, indanyl, or 1,2,3,4-tetrahydro-naphthalenyl;
n is selected from 1, 2, or 3;
$R^{102}$ is $NR^{103}R^{104}$ heteroaryl or phenyl optionally substituted with $R^{101}$;
$R^{101}$ is one, two or three substituents selected from hydroxyl, methyl, halogen, —$CF_3$, or methoxy;
$R^{103}$ and $R^{104}$ are taken together to form a ring selected from the following:

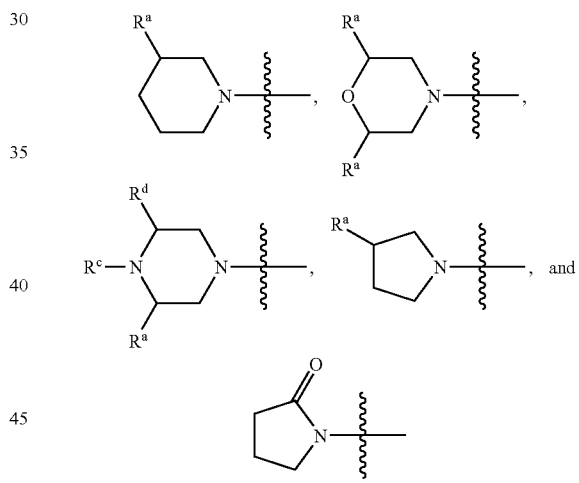

wherein $R^a$ is hydrogen or $C_{(1-4)}$ alkyl, $R^c$ is hydrogen, $C_{(1-4)}$ alkyl or —$CH_2C(O)C_{(1-4)}$ alkyl and $R^d$ is hydrogen, $C_{(1-4)}$ alkyl, or Cl; and Z is $CO_2R^1$, or $CONR^1R^2$; wherein $R^1$ is hydrogen or $C_{(1-4)}$ alkyl; and $R^2$ is hydrogen, $C_{(1-4)}$ alkyl, cycloalkyl, or $C_{(1-4)}$ alkoxy.

2. A compound selected from the group consisting of:
8-Indan-5-yl-2-[4-(4-methyl-piperazin-1-yl)-propylamino]-5-oxo-5,8-dihydro-pyrido[2,3-d]pyrimidine-6-carboxylic acid amide,
8-Indan-5-yl-5-oxo-2-(2-piperidin-1-yl-ethylamino)-5,8-dihydro-pyrido[2,3-d]pyrimidine-6-carboxylic acid amide,
2-(3-Imidazol-1-yl-propylamino)-8-indan-5-yl-5-oxo-5,8-dihydro-pyrido[2,3-d]pyrimidine-6-carboxylic acid amide,
8-Indan-5-yl-2-(2-morpholin-4-yl-ethylamino)-5-oxo-5,8-dihydro-pyrido[2,3-d]pyrimidine-6-carboxylic acid amide, 8-Indan-5-yl-2-(2-morpholin-4-yl-propylamino)-5-oxo-5,8-dihydro-pyrido[2,3-d]pyrimidine-6-carboxylic acid amide, 2-(3-Dimethylamino-propylamino)-8-indan-5-yl-5-oxo-5,8-dihydro-pyrido[2,3-d]pyrimidine-6-carboxylic acid amide, 8-Indan-5-yl-5-oxo-2-[3-(2-oxo-pyrrolidin-1-yl)-propylamino]-5,8-dihydro-pyrido[2,3-d]pyrimidine-6-carboxylic acid amide, 8-Indan-5-yl-5-oxo-2-(3-pyrrolidin-1-yl-propylamino)-5,8-dihydro-pyrido[2,3-d]pyrimidine-6-carboxylic acid amide, 2-(3,5-Dimethoxy-benzylamino)-8-indan-5-yl-5-oxo-5,8-dihydro-pyrido[2,3-d]pyrimidine-6-carboxylic acid amide, 2-(3-Dimethylamino-propylamino)-8-indan-5-yl-5-oxo-5,8-dihydro-pyrido[2,3-d]pyrimidine-6-carboxylic acid methylamide, 8-Indan-5-yl-2-(3-morpholin-4-yl-propylamino)-5-oxo-5,8-dihydro-pyrido[2,3-d]pyrimidine-6-carboxylic acid methylamide, 8-Indan-5-yl-5-oxo-2-[3-(2-oxo-pyrrolidin-1-yl)-propylamino]-5,8-dihydro-pyrido[2,3-d]pyrimidine-6-carboxylic acid methylamide, 8-Indan-5-yl-2-[3-(4-methyl-piperazin-1-yl)-propylamino]-5-oxo-5,8-dihydro-pyrido[2,3-d]pyrimidine-6-carboxylic acid methylamide, 8-Indan-5-yl-2-[2-(4-methoxy-phenyl)-ethylamino]-5-oxo-5,8-dihydro-pyrido[2,3-d]pyrimidine-6-carboxylic acid methylamide, 8-Indan-5-yl-2-(2-morpholin-4-yl-ethylamino)-5-oxo-5,8-dihydro-pyrido[2,3-d]pyrimidine-6-carboxylic acid methylamide, 2-(3-Imidazol-1-yl-propylamino)-8-indan-5-yl-5-oxo-5,8-dihydro-pyrido[2,3-d]pyrimidine-6-carboxylic acid methoxy-amide, 2-(3-Dimethylamino-propylamino)-8-indan-5-yl-5-oxo-5,8-dihydro-pyrido[2,3-d]pyrimidine-6-carboxylic acid methoxy-amide, 8-Indan-5-yl-5-oxo-2-[3-(2-oxo-pyrrolidin-1-yl)-propylamino]-5,8-dihydro-pyrido[2,3-d]pyrimidine-6-carboxylic acid methoxy-amide, 8-Indan-5-yl-2-[2-(4-methoxy-phenyl)-ethylamino]-5-oxo-5,8-dihydro-pyrido[2,3-d]pyrimidine-6-carboxylic acid methoxy-amide, 8-Indan-5-yl-5-oxo-2-(2-piperidin-1-yl-ethylamino)-5,8-dihydro-pyrido[2,3-d]pyrimidine-6-carboxylic acid methoxy-amide, 8-Indan-5-yl-2-(2-morpholin-4-yl-ethylamino)-5-oxo-5,8-dihydro-pyrido[2,3-d]pyrimidine-6-carboxylic acid methoxy-amide, 2-(3,5-Dimethoxy-benzylamino)-8-indan-5-yl-5-oxo-5,8-dihydro-pyrido[2,3-d]pyrimidine-6-carboxylic acid methoxy-amide, 8-Cyclohexyl-2-(3-imidazol-1-yl-propylamino)-5-oxo-5,8-dihydro-pyrido[2,3-d]pyrimidine-6-carboxylic acid amide, 8-Cyclohexyl-2-(3-dimethylamino-propylamino)-5-oxo-5,8-dihydro-pyrido[2,3-d]pyrimidine-6-carboxylic acid amide, 8-Cyclohexyl-2-(3-morpholin-4-yl-propylamino)-5-oxo-5,8-dihydro-pyrido[2,3-d]pyrimidine-6-carboxylic acid amide, 8-Cyclohexyl-5-oxo-2-[3-(2-oxo-pyrrolidin-1-yl)-propylamino]-5,8-dihydro-pyrido[2,3-d]pyrimidine-6-carboxylic acid amide, 8-Cyclohexyl-2-[3-(4-methyl-piperazin-1-yl)-propylamino]-5-oxo-5,8-dihydro-pyrido[2,3-d]pyrimidine-6-carboxylic acid amide, 8-Cyclohexyl-5-oxo-2-(3-pyrrolidin-1-yl-propylamino)-5,8-dihydro-pyrido[2,3-d]pyrimidine-6-carboxylic acid amide, 8-Cyclohexyl-5-oxo-2-(2-pyrrolidin-1-yl-ethylamino)-5,8-dihydro-pyrido[2,3-d]pyrimidine-6-carboxylic acid amide, 8-Cyclohexyl-2-[2-(4-methoxy-phenyl)-ethylamino]-5-oxo-5,8-dihydro-pyrido[2,3-d]pyrimidine-6-carboxylic acid amide, 8-Cyclohexyl-5-oxo-2-(2-piperidin-1-yl-ethylamino)-5,8-dihydro-pyrido[2,3-d]pyrimidine-6-carboxylic acid amide, 8-Cyclohexyl-2-(2-morpholin-4-yl-ethylamino)-5-oxo-5,8-dihydro-pyrido[2,3-d]pyrimidine-6-carboxylic acid amide, 8-Cyclohexyl-2-(3,5-dimethoxy-benzylamino)-5-oxo-5,8-dihydro-pyrido[2,3-d]pyrimidine-6-carboxylic acid amide, 8-Cyclohexyl-2-(3-imidazol-1-yl-propylamino)-5-oxo-5,8-dihydro-pyrido[2,3-d]pyrimidine-6-carboxylic acid methoxy-amide, 8-Cyclohexyl-2-(3-dimethylamino-propylamino)-5-oxo-5,8-dihydro-pyrido[2,3-d]pyrimidine-6-carboxylic acid methoxy-amide, 8-Cyclohexyl-2-(3-morpholin-4-yl-propylamino)-5-oxo-5,8-dihydro-pyrido[2,3-d]pyrimidine-6-carboxylic acid methoxy-amide, 8-Cyclohexyl-2-[3-(4-methyl-piperazin-1-yl)-propylamino]-5-oxo-5,8-dihydro-pyrido[2,3-d]pyrimidine-6-carboxylic acid methoxy-amide, 8-Cyclohexyl-5-oxo-2-(3-pyrrolidin-1-yl-propylamino)-5,8-dihydro-pyrido[2,3-d]pyrimidine-6-carboxylic acid methoxy-amide, 8-Cyclohexyl-5-oxo-2-(2-pyrrolidin-1-yl-ethylamino)-5,8-dihydro-pyrido[2,3-d]pyrimidine-6-carboxylic acid methoxy-amide, 8-Cyclohexyl-2-[2-(4-methoxy-phenyl)-ethylamino]-5-oxo-5,8-dihydro-pyrido[2,3-d]pyrimidine-6-carboxylic acid methoxy-amide, 8-Cyclohexyl-5-oxo-2-(2-piperidin-1-yl-ethylamino)-5,8-dihydro-pyrido[2,3-d]pyrimidine-6-carboxylic acid methoxy-amide, 8-Cyclohexyl-2-(2-morpholin-4-yl-ethylamino)-5-oxo-5,8-dihydro-pyrido[2,3-d]pyrimidine-6-carboxylic acid methoxy-amide, 8-Cyclohexyl-2-(3,5-dimethoxy-benzylamino)-5-oxo-5,8-dihydro-pyrido[2,3-d]pyrimidine-6-carboxylic acid methoxy-amide, 8-Cyclohexyl-2-(3-imidazol-1-yl-propylamino)-5-oxo-5,8-dihydro-pyrido[2,3-d]pyrimidine-6-carboxylic acid methylamide, 8-Cyclohexyl-2-(3-dimethylamino-propylamino)-5-oxo-5,8-dihydro-pyrido[2,3-d]pyrimidine-6-carboxylic acid methylamide, 8-Cyclohexyl-2-(3-morpholin-4-yl-propylamino)-5-oxo-5,8-dihydro-pyrido[2,3-d]pyrimidine-6-carboxylic acid methylamide, 8-Cyclohexyl-2-(2-methoxy-ethylamino)-5-oxo-5,8-dihydro-pyrido[2,3-d]pyrimidine-6-carboxylic acid methylamide, 8-Cyclohexyl-2-[2-(4-methoxy-phenyl)-ethylamino]-5-oxo-5,8-dihydro-pyrido[2,3-d]pyrimidine-6-carboxylic acid methylamide, 8-Cyclohexyl-5-oxo-2-(2-piperidin-1-yl-ethylamino)-5,8-dihydro-pyrido[2,3-d]pyrimidine-6-carboxylic acid methylamide, 8-Cyclohexyl-2-(2-morpholin-4-yl-ethylamino)-5-oxo-5,8-dihydro-pyrido[2,3-d]pyrimidine-6-carboxylic acid methylamide, and 8-Cyclohexyl-2-(3,5-dimethoxy-benzylamino)-5-oxo-5,8-dihydro-pyrido[2,3-d]pyrimidine-6-carboxylic acid methylamide.

3. A pharmaceutical composition, comprising a compound of claim 1 and a pharmaceutically acceptable carrier.

4. A method for inhibiting protein tyrosine kinase activity, comprising contacting the kinase with an effective inhibitory amount of at least one compound of claim 1.

5. A method for inhibiting protein tyrosine kinase activity, comprising contacting the kinase with an effective inhibitory amount of at least one compound of claim 1, wherein the protein tyrosine kinase is c-fms.

6. A pharmaceutical dosage form comprising a pharmaceutically acceptable carrier and from about 0.5 mg to about 10 g of at least one compound of claim 1.

7. A dosage form according to claim 6 adapted for parenteral or oral administration.

8. A compound of Formula I:

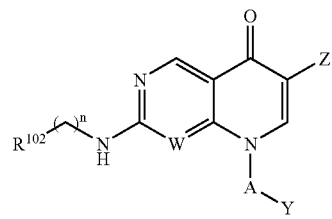

Wherein

W is N or CH;

A is absent or alkyl;

Y is a ring selected from indan-5-yl, phenyl, cyclohexyl, cyclopentyl, or adamantan-2-yl;

n is selected from 1, 2 or 3;

$R^{102}$ is 4-methyl-piperazin-1-yl, morpholinyl, piperidinyl, 2-oxo-pyrrolidin-1-yl, pyrrolidinyl, dimethylamino, imidazolyl, or phenyl optionally substituted with one or two methoxy substituents; and Z is $CONR^1R^2$; wherein $R^1$ is hydrogen or alkyl; and $R^2$ is hydrogen, alkyl, cycloalkyl, or alkoxy.

* * * * *